(12) United States Patent
Burns et al.

(10) Patent No.: US 6,599,918 B2
(45) Date of Patent: Jul. 29, 2003

(54) SUBSTITUTED (AMINOIMINOMETHYL OR AMINOMETHYL) DIHYDROBENZOFURANS AND BENZOPYRANS

(75) Inventors: Christopher J. Burns, Malvern, PA (US); William P. Dankulich, Collegeville, PA (US); Daniel G. McGarry, Bedminister, NJ (US); Francis A. Volz, Neshanic Station, NJ (US)

(73) Assignee: Aventis Pharmaceuticals Inc., Bridgewater, NJ (US)

(*) Notice: Subject to any disclaimer, the term of this patent is extended or adjusted under 35 U.S.C. 154(b) by 0 days.

(21) Appl. No.: 10/081,113

(22) Filed: Feb. 22, 2002

(65) Prior Publication Data

US 2002/0193410 A1 Dec. 19, 2002

Related U.S. Application Data

(63) Continuation of application No. PCT/IB00/01562, filed on Aug. 12, 2000.
(60) Provisional application No. 60/150,767, filed on Aug. 26, 1999.

(30) Foreign Application Priority Data

Oct. 12, 1999 (GB) .............................. 9924155

(51) Int. Cl.$^7$ .................. A61K 31/443; A61K 31/4025; C07D 333/50; C07D 405/02; C07D 409/02
(52) U.S. Cl. ...................... 514/314; 514/337; 514/407; 514/414; 548/364.4; 548/454; 546/122; 546/284.1; 549/58; 549/467
(58) Field of Search .................. 514/314, 337, 514/407, 414, 444, 469; 548/364.4, 454; 546/284.1, 122; 549/58, 467

(56) References Cited

U.S. PATENT DOCUMENTS 5,620,991 A * 4/1997 Nagahara et al.
5,886,191 A * 3/1999 Dominguez et al.

FOREIGN PATENT DOCUMENTS

| EP | 0 350 163 | * | 1/1990 |
| WO | 97/45424 | * | 12/1997 |
| WO | 98/01428 | * | 1/1998 |

* cited by examiner

Primary Examiner—Taofiq Solola
(74) Attorney, Agent, or Firm—Raymond S. Parker, III

(57) ABSTRACT

This invention is directed to substituted (aminoiminomethyl or aminomethyl) dihydrobenzofurans and benzopyrans that inhibit Factor Xa, pharmaceutical compositions comprising these compounds and their use for inhibiting Factor Xa or treating pathological conditions in a patient that may be ameliorated by administration of such compounds. This invention is also is also directed to substituted (aminoiminomethyl or aminomethyl) dihydrobenzofurans and benzopyrans which directly inhibit both Factor Xa and Factor IIa (thrombin), to pharmaceutical compositions comprising these compounds, to intermediates useful for preparing these compounds and to a method of simultaneously directly inhibiting both Factor Xa and Factor IIa (thrombin).

30 Claims, No Drawings

SUBSTITUTED (AMINOIMINOMETHYL OR AMINOMETHYL) DIHYDROBENZOFURANS AND BENZOPYRANS

CROSS-REFERENCE TO RELATED APPLICATIONS

This application is a continuation of PCT/IB00/01562, filed Aug. 12, 2000, which claims priority from U.S. Provisional Application No. 60/150,767, filed Aug. 26, 1999, all incorporated herein by reference.

FIELD OF THE INVENTION

This invention relates to substituted (aminoiminomethyl or aminomethyl) dihydrobenzofurans and benzopyrans that inhibit Factor Xa, pharmaceutical compositions comprising these compounds and their use for inhibiting Factor Xa or treating pathological conditions in a patient that may be ameliorated by administration of such compounds. This invention also relates to substituted (aminoiminomethyl or aminomethyl) dihydrobenzo-furans and benzopyrans which directly inhibit both Factor Xa and Factor IIa (thrombin), to pharmaceutical compositions comprising these compounds, to intermediates useful for preparing these compounds and to a method of simultaneously directly inhibiting both Factor Xa and Factor IIa (thrombin).

BACKGROUND OF THE INVENTION

Factor Xa is the penultimate enzyme in the coagulation cascade. Both free Factor Xa and Factor Xa assembled in the prothrombinase complex (Factor Xa, Factor Va, calcium and phospholipid) are inhibited by compounds of formula I. Moreover, Factor Xa inhibition is effected by direct complex formation between the inhibitor and the enzyme and is therefore independent of the plasma co-factor antithrombin III. Effective Factor Xa inhibition is achieved by administering the compounds either orally, by continuous intravenous infusion, by bolus intravenous administration or by any other parenteral route such that it achieves the desired effect of inhibiting physiological events mediated by the catalytic activity of Factor Xa.

Anticoagulant therapy is indicated for the treatment and prophylaxis of a variety of thrombotic conditions of both the venous and arterial vasculature. In the arterial system, abnormal thrombus formation is primarily associated with arteries of the coronary, cerebral and peripheral vasculature. The diseases associated with thrombotic occlusion of these vessels principally include acute myocardial infarction (AMI), unstable angina, thromboembolism, acute vessel closure associated with thrombolytic therapy and percutaneous transluminal coronary angioplasty (PTCA), transient ischemic attacks, stroke, intermittent claudication and bypass grafting (CABG) of the coronary or peripheral arteries. Chronic anticoagulant therapy may also be beneficial in preventing the vessel luminal narrowing (restenosis) that often occurs following PTCA and CABG, and in the maintenance of vascular access patency in long-term hemodialysis patients. With respect to the venous vasculature, pathologic thrombus formation frequently occurs in the veins of the lower extremities following abdominal, knee and hip surgery (deep vein thrombosis, DVT). DVT further predisposes the patient to a higher risk of pulmonary thromboembolism. A systemic, disseminated intravascular coagulopathy (DIC) commonly occurs in both vascular systems during septic shock, certain viral infections and cancer. This condition is characterized by a rapid consumption of coagulation factors and their plasma inhibitors, resulting in the formation of life-threatening clots throughout the microvasculature of several organ systems.

Accumulated experimental evidence has also indicated that prothrombin activation is only one of the biological activities of Factor Xa. For example, Factor Xa is believed to influence several vascular wall phenomena by interaction with EPR-1 (effector cell protease receptor-1, which recognizes Factor Xa). EPR-1 has been shown to be expressed on human umbilical vein endothelial cells, rat smooth muscle cells and platelets (C R McKenzie, et al., Arterioscler Thromb Vasc Biol 16 1285–91 (1996); F Bono, et al., J Cell Physiol 172 36–43 (1997); A C Nicholson, et al., J Biol Chem 271 28407–13 (1996); and J. M. Herbert, et al., J Clin Invest 101 993–1000 (1998)). This protease-receptor interaction could mediate not only prothrombinase-catalyzed thrombin generation, but also diverse cellular functions such as cell proliferation, release of PDGF and DNA syntheses. The mitogenic effect of Factor Xa has been reported to be dependent on Factor Xa enzymatic activity (F Bono, et al., J Cell Physiol 172 36–43 (1997); and J. M. Herbert, et al., J Clin Invest 101 993–1000 (1998)). TAP, for example, inhibited the mitogenesis of human and rat cultured vascular smooth muscle cells (F Bono, et al., J Cell Physiol 172 36–43 (1997)). In a study of the rabbit carotid artery air-drying injury model, increased EPR-1 expression was detected after vascular injury. Animals treated with the specific Factor Xa inhibitor, DX-9065a, exhibited less neointimal proliferation. The important regulatory role of Factor Xa in the coagulation process coupled with its mitogenic effects points to Factor Xa's involvement in the formation of thrombin at the luminal surface of the vessel wall and contribution to the atherothrombotic process and abnormal proliferation of vascular cells resulting in restenosis or angiogenesis.

Vascular injury caused by biochemical or physical perturbations, results in the activation of the coagulation system, culminating in the generation of thrombin. Thrombin promotes thrombus formation by catalyzing the transformation of fibrinogen to fibrin, by activating Coagulation Factor XIII that stabilizes the thrombus, and by activating platelets. Thrombin promotes further thrombus growth by positive feedback to the coagulation cascade (activation of Coagulation Factors V and VIII), resulting in the explosive production of thrombin. Thrombin is present, and active, in the thrombi of patients with thrombotic vascular disease. Thrombin inhibition prevents the action of thrombin after thrombin has been activated from prothrombin. An inhibitor of thrombin inhibits cleavage of fibrinogen to fibrin, activation of Factor XIIIa, activation of platelets, and feedback of thrombin to the coagulation cascade to generate more thrombin. Consequently, inhibition of thrombin activity with a direct thrombin inhibitor would be useful for preventing or treating disorders related to blood coagulation in mammals.

The combined Xa/IIa inhibitors described here inhibit thrombin activity (via IIa inhibition) and thrombin production (via Factor Xa inhibition). Therefore, these agents inhibit any thrombin that may be present and also inhibit the further production of thrombin. Other agents that have this dual activity include heparin and low molecular weight heparins (LMWHs), which have demonstrated efficacy in thrombotic diseases. However, heparin and LMWHs act indirectly through a cofactor, antithrombin-III (ATIII), to inhibit Xa and IIa. The heparin/ATIII complex is too large, however, to inhibit thrombus-bound Xa and IIa, thus limiting their efficacy. Direct inhibitors of Xa and IIa, as described here, are capable of inhibiting soluble and thrombus-bound Xa and IIa, thus providing an important therapeutic advantage over currently available Xa/IIa inhibitors.

In view of the physiological conditions discussed above related to Factor Xa, inhibitors of Factor Xa would be useful in treating those and other conditions that would be ameliorated by a Factor Xa inhibitor.

SUMMARY OF THE INVENTION

This invention is directed to a compound of formula I:

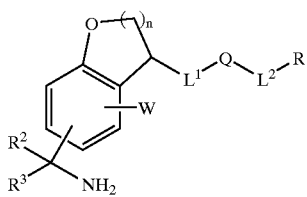

(I)

n=1 or 2

W is H or a ring system substituent.

R is hydrogen, cyano, cycloalkyl, cycloalkenyl, heterocyclyl, heterocyclenyl, fused arylcycloalkyl, fused heteroarylcycloalkyl, fused arylcycloalkenyl, fused heteroaryleycloalkenyl, fused arylheterocyclyl, fused heteroarylheterocyclyl, fused arylheterocyclenyl, fused heteroarylheterocyclenyl, aryl, fused cycloalkenylaryl, fused cycloalkylaryl, fused heterocyclylaryl, fused heterocyclenylaryl, heteroaryl, fused cycloalkylheteroaryl, fused cycloalkenylheteroaryl, fused heterocyclenylheteroaryl, or fused heterocyclyiheteroaryl, $R^1$ is hydrogen, alkyl, aralkyl, heteroaralkyl, acyl, aroyl, heteroaroyl, alkoxycarbonyl, aryloxycarbonyl or heteroaryloxycarbonyl;

$R^2$ and $R^3$ are each hydrogen, or, taken together are $=NR^4$;

$R^4$ is hydrogen, $R^5O_2C-$, $R^5O-$, HO—, cyano, $R^5CO-$, HCO—, lower alkyl, nitro, or $R^6R^7N$;

$R^5$ is alkyl, aryl, heteroaryl, aralkyl, or heteroaralkyl;

$R^6$ and $R^7$ are independently hydrogen or alkyl;

$L^1$ is alkylene, alkenylene or alkynylene;

$L^2$ is absent (i.e. a chemical bond), alkylene, alkenylene, alkynylene, alkylene-O—, alkenylene-O—, alkynylene-O—, alkylene-S—, alkenylene-S—, alkynylene-S—, alkylene-S-alkylene, alkenylene-S-alkylene, alkynylene-S-alkylene, alkylene-O-alkylene, alkenylene-O-alkylene, alkynylene-O-alkylene, alkylene-C(O)—, alkenylene-C(O)—, alkynylene-C(O)—, provided that when $L^2$ is absent, then R is not hydrogen, and Q is attached to R through a carbon atom thereof;

Q is $-NR^{8'}-$, $-O-$, $-C(O)-$, $-C(O)-O-$, $-O-C(O)-$, $-NR^{8'}C(X^1)-$, $-C(X^1)NR^{8'}-$, $NR^8C(X^1)O-$, $-OC(X^1)NR^8-$, $-NR^8C(X^1)NR^8-$, $-NR^8C(X^1)NR^8-$, $-S(O)_m-$, $-NR^8SO_2-$ or $-SO_2NR^8-$, provided that a nitrogen atom or oxygen atom of Q is not directly bonded to a carbon atom of $L^1$ or $L^2$ having a double bond or triple bond, or $Q-L^2-R$ is cycloalkyl, cycloalkenyl, heterocyclyl, heterocyclenyl, fused arylcycloalkyl, fused heteroarylcycloalkyl, fused arylcycloalkenyl, fused heteroarylcycloalkenyl, fused arylheterocyclyl, fused heteroarylheterocyclyl, fused arylheterocyclenyl, fused heteroarylheterocyclenyl, aryl, fused cycloalkenylaryl, fused cycloalkylaryl, fused heterocyclylaryl, fused heterocyclenylaryl, heteroaryl, fused cycloalkylheteroaryl, fused cycloalkenylheteroaryl, fused heterocyclenylheteroaryl or fused heterocyclylheteroaryl, provided that a nitrogen atom or oxygen atom of Q is not directly bonded to a carbon atom of $L^1$ having a double bond or triple bond;

$X^1$ is O or S;

$R^{8'}$ is hydrogen, alkyl, aralkyl, heteroaralkyl, acyl, aroyl, heteroaroyl or alkoxycarbonyl;

$R^8$ is hydrogen, alkyl, aralkyl, heteroaralkyl, acyl, aroyl or heteroaroyl; and m is 0, 1 or 2, or an oxide thereof, a pharmaceutically acceptable salt thereof, a solvate thereof, or prodrug thereof.

DETAILED DESCRIPTION OF THE INVENTION

As used above, and throughout the description of the invention, the following terms, unless otherwise indicated, shall be understood to have the following meanings:

Definitions

"Patient" includes both human and other mammals.

"Alkyl" means an aliphatic hydrocarbon group that may be straight or branched-chain having about 1 to about 15 carbon atoms in the chain. Preferred alkyl groups have 1 to about 10 carbon atoms in the chain. Branched means that one or more lower alkyl groups such as methyl, ethyl or propyl are attached to a linear alkyl chain. "Lower alkyl" means 1 to about 4 carbon atoms in the chain, which may be straight or branched. The alkyl may be substituted with one or more "alkyl group substituents" that may be the same or different, and include halo, cycloalkyl, cycloalkenyl, heterocyclyl, heterocyclenyl, hydroxy, alkoxy, aryloxy, heteroaryloxy, amino, acylamino, aroylamino, carboxy, alkoxycarbonyl, aralkoxycarbonyl, heteroaralkoxycarbonyl $Y^1Y^2N-$ $Y^1Y^2NCO-$, $Y^1Y^2NCONH-$, $Y^1Y^2NCO_2-$ $Y^1Y^2NSO_2-$, wherein $Y^1$ and $Y^2$ are independently hydrogen, alkyl, aryl, heteroaryl, alkoxyalkyl, hydroxyalkyl. Representative alkyl groups include methyl, fluoromethyl, difluoromethyl, trifluoromethyl, cyclopropylmethyl, cyclopentylmethyl, ethyl, n-propyl, i-propyl, n-butyl, t-butyl, n-pentyl, 3-pentyl, heptyl, octyl, nonyl, decyl and dodecyl.

"Alkylene" means a straight or branched bivalent hydrocarbon chain having from 1 to about 10 carbon atoms. The preferred alkylene groups are the lower alkylene groups having from 1 to about 4 carbon atoms. The alkylene group may be substituted by one or more halo, hydroxy, acyl, alkoxycarbonyl aryl, heteroaryl or carboxy substitutent(s). Exemplary alkylene groups include methylene, ethylene, propylene and butylene; preferred is ethylene.

"Alkenyl" means an aliphatic hydrocarbon group containing a carbon-carbon double bond and which may be straight or branched-chain having 2 to about 15 carbon atoms in the chain. Preferred alkenyl groups have 2 to about 10 carbon atoms in the chain; and more preferably 2 to about 4 carbon atoms in the chain. Branched means that one or more lower alkyl groups, such as methyl, ethyl or propyl, are attached to a linear alkenyl chain. "Lower alkenyl" means 2 to about 4 carbon atoms in the chain, which may be straight or branched. The alkenyl group may be substituted by one or more halo. Representative alkenyl groups include ethenyl, propenyl, n-butenyl, i-butenyl, 3-methylbut-2-enyl, n-pentenyl, heptenyl, octenyl and decenyl.

"Alkenylene" means a straight or branched bivalent hydrocarbon chain having a double bond and from 2 to about 10 carbon atoms. Preferred alkenylene groups are the lower alkenylene groups having from 2 to about 4 carbon atoms. The alkenylene group may be substituted by one or more halo, hydroxy, acyl, alkoxycarbonyl alkoxycarbonyl, aryl, heteroaryl or carboxy substituents, provided that the hydroxy is not substituted at a carbon thereof having a double bond. Exemplary alkenylene groups include ethenylene, propenylene and butenylene.

"Alkynyl" means an aliphatic hydrocarbon group containing a carbon-carbon triple bond, which may be straight or branched-chain having 2 to about 15 carbon atoms in the chain. Preferred alkynyl groups have 2 to about 10 carbon atoms in the chain, more preferably 2 to about 4 carbon atoms in the chain. Branched means that one or more lower alkyl groups, such as methyl, ethyl or propyl, are attached to a linear alkynyl chain. "Lower alkynyl" means 2 to about 4 carbon atoms in the chain that may be straight or branched. Representative alkynyl groups include ethynyl, propynyl, n-butynyl, 2-butynyl, 3-methylbutynyl, n-pentynyl, heptynyl, octynyl and decynyl.

"Alkynylene" means a straight or branched bivalent hydrocarbon chain having a carbon-carbon triple bond and from 2 to about 10 carbon atoms. Preferred alkynylene groups are the lower alkynylene groups having from 2 to about 4 carbon atoms. The alkynylene group may be substituted by one or more halo, hydroxy, acyl, alkoxycarbonyl aryl, heteroaryl or carboxy substituent(s), provided that the hydroxy is not substituted at a carbon thereof having a triple bond. Exemplary alkynylene groups include ethynylene, propynylene and butynylene.

"Chemical bond" means a direct bond.

"Cycloalkyl" means a non-aromatic mono- or multicyclic ring system of about 3 to about 10 carbon atoms, preferably of about 5 to about 10 carbon atoms. Preferred cycloalkyl rings contain about 5 to about 6 ring atoms. The cycloalkyl ring system is optionally substituted with one or more "ring system substituents" which may be the same or different, and are as defined herein. Representative monocyclic cycloalkyl groups include cyclopentyl, cyclohexyl, cycloheptyl, and the like. Representative multicyclic cycloalkyl groups include 1-decalin, norbornyl, adamantyl, and the like.

"Cycloalkenyl" means a non-aromatic mono- or multicyclic ring system of 3 to about 10 carbon atoms, preferably of about 5 to about 10 carbon atoms which contains at least one carbon-carbon double bond. Preferred cycloalkylene rings contain about 5 to 6 ring atoms. The cycloalkenyl ring system is optionally substituted with one or more "ring system substituents" which may be the same or different, and are as defined herein. Representative monocyclic cycloalkenyl rings include cyclopentenyl, cyclohexenyl, cycloheptenyl, and the like. A representative multicyclic cycloalkenyl is norbornylenyl.

"Heterocyclenyl" means a non-aromatic monocyclic or multicyclic ring system of 3 to about 10 ring atoms, preferably about 5 to about 10 ring atoms, in which one or more of the atoms in the ring system is/are element(s) other than carbon, for example nitrogen, oxygen or sulfur atoms, and which system contains at least one carbon-carbon double bond or carbon-nitrogen double bond. Preferred heterocyclenyl rings contain about 5 to 6 ring atoms. The prefix aza, oxa or thia before heterocyclenyl means that at least a nitrogen, oxygen or sulfur atom, respectively, is present as a ring atom. The heterocyclenyl ring system is optionally substituted by one or more ring system substituents, wherein "ring system substituent" is as defined herein. The nitrogen or sulphur atom of the heterocyclenyl ring system is optionally oxidized to the corresponding N-oxide, S-oxide or S,S-dioxide. Representative monocyclic azaheterocyclenyl groups include 1,2,3,4-tetrahydropyridine, 1,2-dihydropyridyl, 1,4-dihydropyridyl, 1,2,3,6-tetrahydropyridine, 1,4,5,6-tetrahydropyrimidine, 2-pyrrolinyl, 3-pyrrolinyl, 2-imidazolinyl, 2-pyrazolinyl, and the like. Representative oxaheterocyclenyl groups include 3,4-dihydro-2H-pyran, dihydrofuranyl, fluorodihydrofuranyl, and the like. Representative multicyclic oxaheterocyclenyl groups are 7-oxabicyclo[2.2.1] heptenyl and 4,5,6,7-tetrahydro-benzofuranyl. Representative monocyclic thiaheterocyclenyl rings include dihydrothiophenyl, dihydrothiopyranyl, and the like. A heterocyclenyl may also be a "lactam" where the heterocyclenyl is an appropriately dioxo substituted azaheterocyclenyl, for example maleimide.

"Heterocyclyl" means a non-aromatic saturated monocyclic or multicyclic ring system of 3 to about 10 ring atoms, preferably about 5 to about 10 ring atoms, in which one or more of the atoms in the ring system is/are element(s) other than carbon, for example nitrogen, oxygen or sulfur. Preferred heterocyclyls contain about 5 to 6 ring atoms. The prefix aza, oxa or thia before heterocyclyl means that at least a nitrogen, oxygen or sulfur atom, respectively, is present as a ring atom. The heterocyclyl ring system is optionally substituted by one or more "ring system substituents", which may be the same or different, and are as defined herein. The nitrogen or sulphur atom of the heterocyclyl is optionally oxidized to the corresponding N-oxide, S-oxide or S,S-dioxide. Representative monocyclic heterocyclyl rings include piperidyl; pyrrolidinyl; piperazinyl; morpholinyl; thiomorpholinyl; thiazolidinyl; 1,3-dioxolanyl; 1,4-dioxanyl; tetrahydrofuranyl; tetrahydrothiophenyl; tetrahydrothiopyranyl, [1,2]dithiolan, and the like. A heterocyclyl may also be a "lactam" where the heterocyclyl is an appropriately dioxo substituted azaheterocyclyl, for example succinimide.

"Aryl" means an aromatic monocyclic or multicyclic ring system of 6 to about 14 carbon atoms, preferably of 6 to about 10 carbon atoms. The aryl is optionally substituted with one or more "ring system substituents" which may be the same or different, and are as defined herein. Representative aryl groups include phenyl, naphthyl, substituted phenyl and substituted naphthyl.

"Heteroaryl" means an aromatic monocyclic or multicyclic ring system of about 5 to about 14 ring atoms, preferably about 5 to about 10 ring atoms, in which one or more of the atoms in the ring system is/are element(s) other than carbon, for example, nitrogen, oxygen or sulfur. Preferred heteroaryls contain about 5 to 6 ring atoms. The "heteroaryl" is optionally substituted by one or more "ring system substituents", which may be the same or different, and are as defined herein. The prefix aza, oxa or thia before heteroaryl means that at least a nitrogen, oxygen or sulfur atom, respectively, is present as a ring atom. A nitrogen atom of a heteroaryl is optionally oxidized to the corresponding N-oxide. Representative heteroaryls include pyrazinyl; furanyl; thienyl; pyridyl; pyrimidinyl; isoxazolyl; isothiazolyl; oxazolyl; thiazolyl; pyrazolyl; furazanyl; pyrrolyl; pyrazolyl; triazolyl; 1,2,4-thiadiazolyl; pyrazinyl; pyridazinyl; quinoxalinyl; phthalazinyl; 1(2H)-phthalazinonyl; imidazo[1,2-a]pyridine; imidazo[2,1-b]thiazolyl; benzofurazanyl; indolyl; azaindolyl; benzimidazolyl; benzothienyl; quinolinyl; imidazolyl; thienopyridyl; quinazolinyl; thienopyrimidyl; pyrrolopyridyl; imidazopyridyl; isoquinolinyl; benzoazaindolyl; azabenzimidazolyl, 1,2,4-triazinyl; benzothiazolyl and the like.

"Fused arylcycloalkenyl" means a radical derived from a fused aryl and cycloalkenyl as defined herein by removal of hydrogen atom from the cycloalkenyl portion. Preferred fused arylcycloalkenyls are those wherein aryl is phenyl and the cycloalkenyl contains about 5 to 6 ring atoms. The fused arylcycloalkenyl is optionally substituted by one or more ring system substituents, wherein "ring system substituent" is as defined herein. Representative fused arylcycloalkenyl include 1,2-dihydronaphthylene, indene, and the like, in which the bond to the parent moiety is through a non-aromatic carbon atom.

"Fused cycloalkenylaryl" means a radical derived from a fused arylcycloalkenyl as defined herein by removal of hydrogen atom from the aryl portion. Representative fused cycloalkenylaryl are as described herein for a fused arylcycloalkenyl, except that the bond to the parent moiety is through an aromatic carbon atom.

"Fused arylcycloalkyl" means a radical derived from a fused aryl and cycloalkyl as defined herein by removal of a hydrogen atom from the cycloalkyl portion. Preferred fused arylcycloalkyls are those wherein aryl is phenyl and the cycloalkyl contains about 5 to 6 ring atoms. The fused arylcycloalkyl is optionally substituted by one or more ring system substituents, wherein "ring system substituent" is as defined herein. Representative fused arylcycloalkyl include 1,2,3,4-tetrahydronaphthyl, and the like, in which the bond to the parent moiety is through a non-aromatic carbon atom.

"Fused cycloalkylaryl" means a radical derived from a fused arylcycloalkyl as defined herein by removal of a hydrogen atom from the aryl portion. Representative fused cycloalkylaryl are as described herein for a fused arylcycloalkyl radical, except that the bond to the parent moiety is through an aromatic carbon atom.

"Fused arylheterocyclenyl" means a radical derived from a fused aryl and heterocyclenyl as defined herein by removal of a hydrogen atom from the heterocyclenyl portion. Preferred fused arylheterocyclenyls are those wherein aryl is phenyl and the heterocyclenyl contains about 5 to 6 ring atoms. The prefix aza, oxa or thia before the heterocyclenyl portion of the fused arylheterocyclenyl means that at least a nitrogen, oxygen or sulfur atom, respectively, is present as a ring atom. The fused arylheterocyclenyl is optionally substituted by one or more ring system substituents, wherein "ring system substituent" is as defined herein. The nitrogen or sulphur atom of the heterocyclenyl portion of the fused arylheterocyclenyl is optionally oxidized to the corresponding N-oxide, S-oxide or S,S-dioxide. Representative fused arylheterocyclenyl include 3H-indolinyl; 1H-2-oxoquinolyl; 2H-1-oxoisoquinolyl; 1,2-dihydroquinolinyl; 3,4-dihydroquinolinyl; 1,2-dihydroisoquinolinyl; 3,4-dihydroisoquinolinyl, and the like, in which the bond to the parent moiety is through a non-aromatic carbon atom.

"Fused heterocyclenylaryl" means a radical derived from a fused arylheterocyclenyl as defined herein by removal of a hydrogen atom from the aryl portion. Representative fused heterocyclenylaryl are as defined herein for a fused arylheterocyclenyl radical, except that the bond to the parent moiety is through an aromatic carbon atom.

"Fused arylheterocyclyl" means a radical derived from a fused aryl and heterocyclyl as defined herein by removal of a hydrogen atom from the heterocyclyl portion. Preferred fused arylheterocyclyls are those wherein aryl is phenyl and the heterocyclyl containing about 5 to 6 ring atoms. The prefix aza, oxa or thia before heterocyclyl means that at least a nitrogen, oxygen or sulfur atom, respectively, is present as a ring atom. The fused arylheterocyclyl is optionally substituted by one or more ring system substituents, wherein "ring system substituent" is as defined herein. The nitrogen or sulphur atom of the heterocyclyl portion of the fused arylheterocyclyl is optionally oxidized to the corresponding N-oxide, S-oxide or S,S-dioxide. Representative preferred fused arylheterocyclyl ring systems include phthalimide; 1,4-benzodioxane; indolinyl; 1,2,3,4-tetrahydroisoquinoline; 1,2,3,4-tetrahydroquinoline; 1H-2,3-dihydroisoindolyl; 2,3-dihydrobenz[f]isoindolyl; 1,2,3,4-tetrahydrobenz[g]isoquinolinyl, 1,3-benzodioxole, xanthene and the like, in which the bond to the parent moiety is through a non-aromatic carbon atom.

"Fused heterocyclylaryl" means a radical derived from a fused arylheterocyclyl as defined herein by removal of a hydrogen atom from the heterocyclyl portion. Representative preferred fused heterocyclylaryl ring systems are as described for fused arylheterocyclyl, except that the bond to the parent moiety is through an aromatic carbon atom. A fused heterocyclylaryl may also be a "lactam" where the heterocyclyl is an appropriately dioxo substituted azaheterocyclenyl, for example phthalimide.

"Fused heteroarylcycloalkenyl" means a radical derived from a fused heteroaryl and cycloalkenyl as defined herein by removal of a hydrogen atom from the cycloalkenyl portion. Preferred fused heteroarylcycloalkenyls are those wherein the heteroaryl and the cycloalkenyl each contain about 5 to 6 ring atoms. The prefix aza, oxa or thia before heteroaryl means that at least a nitrogen, oxygen or sulfur atom, respectively, is present as a ring atom. The fused heteroarylcycloalkenyl is optionally substituted by one or more ring system substituents, wherein "ring system substituent" is as defined herein. The nitrogen atom of the heteroaryl portion of the fused heteroarylcycloalkenyl is optionally oxidized to the corresponding N-oxide. Representative fused heteroarylcycloalkenyl include 5,6-dihydroquinolyl; 5,6-dihydroisoquinolyl; 5,6-dihydroquinoxalinyl; 5,6-dihydroquinazolinyl; 4,5-dihydro-1H-benzimidazolyl; 4,5-dihydrobenzoxazolyl, and the like, in which the bond to the parent moiety is through a non-aromatic carbon atom.

"Fused cycloalkenylheteroaryl" means a radical derived from a fused heteroarylcycloalkenyl as defined herein by removal of a hydrogen atom from the heteroaryl portion. Representative fused cycloalkenylheteroaryl are as described herein for fused heteroaylcycloalkenyl, except that the bond to the parent moiety is through an aromatic carbon atom.

"Fused heteroarylcycloalkyl" means a radical derived from a fused heteroaryl and cycloalkyl as defined herein by removal of a hydrogen atom from the cycloalkyl portion. Preferred fused heteroarylcycloalkyls are those wherein the heteroaryl thereof contains about 5 to 6 ring atoms and the cycloalkyl contains about 5 to 6 ring atoms. The prefix aza, oxa or thia before heteroaryl means that at least a nitrogen, oxygen or sulfur atom is present, respectively, as a ring atom. The fused heteroarylcycloalkyl is optionally substituted by one or more ring system substituents, wherein "ring system substituent" is as defined herein. The nitrogen atom of the heteroaryl portion of the fused heteroarylcycloalkyl is optionally oxidized to the corresponding N-oxide. Representative fused heteroarylcycloalkyls include 5,6,7,8-tetrahydroquinolinyl; 5,6,7,8-tetrahydroisoquinolyl; 5,6,7,8-tetrahydroquinoxalinyl; 5,6,7,8-tetrahydroquinazolyl; 4,5,6,7-tetrahydro-1H-benzimidazolyl; 4,5,6,7-tetrahydrobenzoxazolyl; 1H-4-oxa-1,5-diazanaphthalen-2-only; 1,3-dihydroimidizole-[4,51-pyridin-2-onyl, 4,5,6,7- tetrahydro-benzo[c]thienyl, and the like, in which the bond to the parent moiety is through a non-aromatic carbon atom.

"Fused cycloalkylheteroaryl" means a radical derived from a fused heteroarylcycloalkyl as defined herein by removal of a hydrogen atom from the heteroaryl portion. Representative fused cycloalkylheteroaryl are as described herein for fused heteroarylcycloalkyl, except that the bond to the parent moiety is through an aromatic carbon atom.

"Fused heteroarylheterocyclenyl" means a radical derived from a fused heteroaryl and heterocyclenyl as defined herein by the removal of a hydrogen atom from the heterocyclenyl portion. Preferred fused heteroarylheterocyclenyls are those wherein the heteroaryl thereof contains about 5 to 6 ring atoms and the heterocyclenyl contains about 5 to 6 ring atoms. The prefix aza, oxa or thia before heteroaryl or heterocyclenyl means that at least a nitrogen, oxygen or sulfur atom is present respectively as a ring atom. The fused heteroarylheterocyclenyl is optionally substituted by one or more ring system substituents, wherein "ring system substituent" is as defined herein. The nitrogen atom of the heteroaryl portion of the fused heteroarylheterocyclenyl is optionally oxidized to the corresponding N-oxide. The nitrogen or sulphur atom of the heterocyclenyl portion of the fused heteroarylheterocyclenyl is optionally oxidized to the corresponding N-oxide, S-oxide or S,S-dioxide. Representative fused heteroarylheterocyclenyl groups include 7,8-dihydro[1,7]naphthyridinyl; 1,2-dihydro[2,7]naphthyridinyl; 6,7-dihydro-3H-imidazo[4,5-c]pyridyl; 1,2-dihydro-1,5-naphthyridinyl; 1,2-dihydro-1,6-naphthyridinyl; 1,2-dihydro-1,7-naphthyridinyl; 1,2-dihydro-1,8-naphthyridinyl; 1,2-dihydro-2,6-naphthyridinyl, and the like, in which the bond to the parent moiety is through a non-aromatic carbon atom.

"Fused heterocyclenylheteroaryl" means a radical derived from a fused heteroarylheterocyclenyl as defined herein by the removal of a hydrogen atom from the heteroaryl portion. Representative fused heterocyclenylheteroaryl are as described herein for fused heteroarylheterocyclenyl, except that the bond to the parent moiety is through an aromatic carbon atom.

"Fused heteroarylheterocyclyl" means a radical derived from a fused heteroaryl and heterocyclyl as defined herein, by removal of a hydrogen atom from the heterocyclyl portion. Preferred fused heteroarylheterocyclyls are those wherein the heteroaryl thereof consists of about 5 to 6 ring atoms and the heterocyclyl consists of about 5 to 6 ring atoms. The prefix aza, oxa or thia before the heteroaryl or heterocyclyl portion of the fused heteroarylheterocyclyl means that at least a nitrogen, oxygen or sulfur atom respectively is present as a ring atom. The fused heteroaryl-heterocyclyl is optionally substituted by one or more ring system substituents, wherein "ring system substituent" is as defined herein. The nitrogen atom of the heteroaryl portion of the fused heteroarylheterocyclyl is optionally oxidized to the corresponding N-oxide. The nitrogen or sulphur atom of the heterocyclyl portion of the fused heteroarylheterocyclyl is optionally oxidized to the corresponding N-oxide, S-oxide or S,S-dioxide. Representative fused heteroarylheterocyclyl include 2,3-dihydro-1H pyrrol[3,4-b]quinolin-2-yl; 1,2,3,4-tetrahydrobenz [b][1,7]naphthyridin-2-yl; 1,2,3,4-tetrahydrobenz [b][1,6]naphthyridin-2-yl; 1,2,3,4-tetrahydro-9H-pyrido[3,4-b]indol-2yl; 1,2,3,4-tetrahydro-9H-pyrido[4,3-b]indol-2yl; 2,3,-dihydro-1H-pyrrolo[3,4-b]indol-2-yl; 1H-2,3,4,5-tetrahydroazepino[3,4-b]indol-2-yl; 1H-2,3,4,5-tetrahydroazepino[4,3-b]indol-3-yl; 1H-2,3,4,5-tetrahydroazepino[4,5-b]indol-2 yl; 5,6,7,8-tetrahydro[1,7]naphthyridinyl; 1,2,3,4-tetrhydro[2,7]naphthyridyl; 2,3-dihydro[1,4]dioxino[2,3-b]pyridyl; 2,3-dihydro-[1,4]dioxino[2,3-b]pyridyl; 3,4-dihydro-2H-1-oxa[4,6]diazanaphthalenyl; 4,5,6,7-tetrahydro-3H-imidazo[4,5-c]pyridyl; 6,7-dihydro[5,8]diazanaphthalenyl; 1,2,3,4-tetrahydro[1,5] naphthyridinyl; 1,2,3,4-tetrahydro[1,6] naphthyridinyl; 1,2,3,4-tetrahydro[1,7]naphthyridinyl; 1,2,3,4-tetrahydro[1,8]naphthyridinyl; 1,2,3,4-tetrahydro[2,6] naphthyridinyl, xanthine and the like, in which the bond to the parent moiety is through a non-aromatic carbon atom.

"Fused heterocyclylheteroaryl" means a radical derived from a fused heteroarylheterocyclyl as defined herein, by removal of a hydrogen atom from the heteroaryl portion. Representative fused heterocyclylheteroaryl are as described herein for fused heteroarylheterocyclyl, except that the bond to the parent moiety is through an aromatic carbon atom.

"Aralkyl" means an aryl-alkyl-group in which the aryl and alkyl are as defined herein. Preferred aralkyls contain a lower alkyl moiety. Representative aralkyl groups include benzyl, 2-phenethyl and naphthlenemethyl.

"Aralkenyl" means an aryl-alkenyl-group in which the aryl and alkenyl are as defined herein. Preferred aralkenyls contain a lower alkenyl moiety. Representative aralkenyl groups include 2-phenethenyl and 2-naphthylethenyl.

"Aralkynyl" means an aryl-alkynyl-group in which the aryl and alkynyl are as defined herein. Preferred aralkynyls contain a lower alkynyl moiety. Representative aralkynyl groups include phenacetylenyl and naphthylacetylenyl.

"Heteroaralkyl" means an heteroaryl-alkyl-group in which the heteroaryl and alkyl are as defined herein. Preferred heteroaralkyls contain a lower alkyl moiety. Representative aralkyl groups include pyridylmethyl, 2-(furan-3-yl)ethyl and quinolin-3-ylmethyl.

"Heteroaralkenyl" means an heteroaryl-alkenyl-group in which the heteroaryl and alkenyl are as defined herein. Preferred heteroaralkenyls contain a lower alkenyl moiety. Representative heteroaralkenyl groups include 2-(pyrid-3-yl)ethenyl and 2-(quinolin-3-yl)ethenyl.

"Heteroaralkynyl" means an heteroaryl-alkynyl-group in which the heteroaryl and alkynyl are as defined herein. Preferred heteroaralkynyls contain a lower alkynyl moiety. Representative heteroaralkynyl groups include pyrid-3-ylacetylenyl and quinolin-3-ylacetylenyl.

"Hydroxyalkyl" means a HO-alkyl-group in which alkyl is as defined herein. Preferred hydroxyalkyls contain lower alkyl. Representative hydroxyalkyl groups include hydroxymethyl and 2-hydroxyethyl.

"Acyl" means an H—CO— or an alkyl-CO— group in which the alkyl group is as defined herein. Preferred acyls contain a lower alkyl. Representative acyl groups include formyl, acetyl, propanoyl, 2-methylpropanoyl, butanoyl and palmitoyl.

"Aroyl" means an aryl-CO— group in which the aryl group is as defined herein. Representative groups include benzoyl and 1- and 2-naphthoyl.

"Heteroaroyl" means a heteroaryl-CO— group in which the heteroaryl group is as defined herein. Representative heteroaroyl groups include nicotinoyl, pyrrol-2-ylcarbonyl and 3-quinolincarbonyl.

"Alkoxy" means an alkyl-O— group in which the alkyl group is as defined herein. Representative alkoxy groups include methoxy, ethoxy, n-propoxy, i-propoxy, n-butoxy and heptoxy.

"Aryloxy" means an aryl-O— group in which the aryl group is as defined herein. Representative aryloxy groups include phenoxy and naphthoxy.

"Heteroaryloxy" means an heteroaryl-O— group in which the heteroaryl group is as defined herein. Representative heteroaryloxy groups include pyridyloxy and thienyloxy.

"Aralkyloxy" means an aralkyl-O— group in which the aralkyl group is as defined herein. Representative aralkyloxy groups include benzyloxy and 1- or 2-naphthalenemethoxy.

"Alkylthio" means an alkyl-S— group in which the alkyl group is as defined herein. Representative alkylthio groups include methylthio, ethylthio, i-propylthio and heptylthio.

"Arylthio" means an aryl-S— group in which the aryl group is as defined herein. Representative arylthio groups include phenylthio and naphthylthio.

"Aralkylthio" means an aralkyl-S— group in which the aralkyl group is as defined herein. A representative aralkylthio group is benzylthio.

"$Y^1Y^2N$—" means a substituted or unsubstituted amino group, wherein $Y^1$ and $Y^2$ are as defined herein. Representative amino groups include amino ($H_2N$—), methylamino, ethylmethylamino, dimethylamino and diethylamino.

"Alkoxycarbonyl" means an alkyl-O—CO— group. Representative alkoxycarbonyl groups include methoxy- and ethoxycarbonyl.

"Aryloxycarbonyl" means an aryl-O—CO— group. Representative aryloxycarbonyl groups include phenoxy- and naphthoxycarbonyl.

"Aralkoxycarbonyl" means an aralkyl-O—CO— group. A representative aralkoxycarbonyl group is benzyloxycarbonyl.

"$Y^1Y^2NCO$—" means a substituted or unsubstituted carbamoyl group, wherein $Y^1$ and $Y^2$ are as defined herein. Representative carbamoyl groups are carbamoyl ($H_2NCO$—) and dimethylcarbamoyl ($Me_2NCO$—).

"$Y^1Y^2NSO_2$—" means a substituted or unsubstituted sulfamoyl group, wherein $Y^1$ and $Y^2$ are as defined herein. Representative sulfamoyl groups are sulfamoyl ($H_2NSO_2$—) and dimethylsulfamoyl ($Me_2NSO_2$—).

"Alkylsulfonyl" means an alkyl-$SO_2$— group. Preferred alkylsulfonyl groups are those in which the alkyl group is lower alkyl.

"Alkylsulfinyl" means an alkyl-SO— group. Preferred alkylsulfinyl groups are those in which the alkyl group is lower alkyl.

"Arylsulfonyl" means an aryl-$SO_2$— group.

"Arylsulfinyl" means an aryl-SO— group.

"Halo" means fluoro, chloro, bromo, or iodo. Preferred are fluoro, chloro or bromo, and more preferred are fluoro or chloro.

"Ring system substituent" means a substituent that optionally replaces hydrogen on an aromatic or non-aromatic ring system. Ring system substituents are selected from the group consisting of alkyl, aryl, heteroaryl, aralkyl, aralkenyl, aralkynyl, heteroaralkyl, heteroaralkenyl, heteroaralkynyl, hydroxy, hydroxyalkyl, alkoxy, aryloxy, aralkoxy, acyl, aroyl, halo, nitro, cyano, carboxy, alkoxycarbonyl, aryloxycarbonyl, heteroaryloxycarbonyl, aralkoxycarbonyl, heteroaralkoxycarbonyl, alkylsulfonyl, arylsulfonyl, heteroarylsulfonyl, alkylsultinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, aryldiazo, heteroaryldiazo, amidino, 1-azaheterocyclylcarbonyl, $Y^1Y^2N$—, $Y^1Y^2N$-alkenyl-, $Y^1Y^2N$-alkynyl-, $Y^1Y^2NCO$—, $Y^1Y^2NCONH$—, $Y^1Y^2NCO_2$—$Y^1Y^2NSO_2$—, wherein $Y^1$ and $Y^2$ are independently hydrogen, alkyl, alkoxyalkyl, hydroxyalkyl, provided that, when the substituent is $Y^1Y^2N$— or $Y^1Y^2N$-alkyl-, then one of $Y^1$ and $Y^2$ is acyl or aroyl and the other of $Y^1$ and $Y^2$ is hydrogen, alkyl, aryl, or aralkyl. When a ring system is saturated or partially saturated, the "ring system substituent" is further selected from methylene ($H_2C$=), oxo (O=) and thioxo (S=).

"Solvate" means a physical association of a compound of this invention with one or more solvent molecules. This physical association involves varying degrees of ionic and covalent bonding, including hydrogen bonding. In certain instances, the solvate will be capable of isolation, for example, when one or more solvent molecules are incorporated in the crystal lattice of the crystalline solid. "Solvate" encompasses both solution-phase and isolable solvates. Representative solvates include ethanolates, methanolates, and the like. "Hydrate" is a solvate wherein the solvent molecules are $H_2O$.

"Prodrug" means a form of the compound of formula I suitable for administration to a patient without undue toxicity, irritation, allergic response, and the like, and effective for their intended use, including ketal, ester and zwitterionic forms. A prodrug is transformed in vivo to yield the parent compound of the above formula, for example by hydrolysis in blood. A thorough discussion is provided in T. Higuchi and V. Stella, Pro-drugs as Novel Delivery Systems, Vol. 14 of the A. C. S. Symposium Series, and in Edward B. Roche, ed., Bioreversible Carriers in Drug Design, American Pharmaceutical Association and Pergamon Press, 1987, the contents of which are hereby incorporated herein by reference.

"Acid protecting group" means an easily removable group which is known in the art to protect an acid group against undesirable reaction during synthetic procedures and preferably to be selectively removable. The use of acid protecting groups is well known in the art for protecting carboxylic acid groups against undesirable reactions during a synthetic procedure, and many such protecting groups are known to those skilled in the art, having been extensively used in the protection of carboxyl groups in the penicillin and cephalosporin fields, as described in U.S. Pat. Nos. 3,840,556 and 3,719,667, the disclosures of which are hereby incorporated herein by reference. For suitable protecting groups, see T. W. Green and P. G. M. Wuts in "Protective Groups in Organic Chemistry" John Wiley and Sons, 1991. Examples of carboxylic acid protecting groups include esters, such as methoxymethyl, methylthiomethyl, tetrahydropyranyl, substituted and unsubstituted phenacyl, 2,2,2-trichloroethyl, tert-butyl, cinnamyl, dialkylaminoalkyl (e.g., dimethylaminoethyl and the like), trimethylsilyl, and the like; $C_1$ to $C_8$ lower-alkyl (e.g., methyl, ethyl or tertiary butyl and the like); and amides and hydrazides, including N,N-dimethyl amide, 7-nitroindolyl hydrazide, N-phenylhydrazide; and benzyl and benzyl substituted derivatives thereof such as alkoxybenzyl or nitrobenzyl groups and the like; alkanoyloxyalkyl groups such as pivaloyloxymethyl or propionyloxymethyl and the like; aroyloxyalkyl, such as benzoyloxyethyl and the like; alkoxycarbonylalkyl, such as methoxycarbonylmethyl, cyclohexyloxy-carbonylmethyl and the like; alkoxycarbonyloxyalkyl, such as t-butyloxycarbonyloxymethyl and the like; alkoxycarbonylaminoalkyl, such as t-butyloxycarbonylaminomethyl and the like; alkylaminocarbonylaminoalkyl, such as methylaminocarbonylaminomethyl and the like; alkanoylaminoalkyl, such as acetylaminomethyl and the like; heterocyclylcarbonyloxyalkyl, such as 4-methylpiperazinylcarbonyloxymethyl and the like; dialkylaminocarbonylalkyl, such as dimethylaminocarbonylmethyl and the like; (5-(loweralkyl)-2-oxo-1,3-dioxolen-4-yl)alkyl, such as (5-t-butyl-2-oxo-1,3-dioxolen-4-yl) methyl and the like; and (5-phenyl-2-oxo-1,3-dioxolen-4-yl)alkyl, such as (5-phenyl-2-oxo-1,3-dioxolen-4-yl)methyl and the like.

"Amine protecting group" means an easily removable group that is known in the art to protect an amino group against undesirable reaction during synthetic procedures and preferably to be selectively removable. The use of amine protecting groups is well known in the art for protecting amine groups against undesirable reactions during a synthetic procedure and many such protecting groups are known; see, for example, T. H. Greene and P. G. M. Wuts, Protective Groups in Organic Synthesis, 2nd edition, John Wiley & Sons, New York (1991), the contents of which are hereby incorporated herein by reference. Preferred amine protecting groups are acyl, including formyl, acetyl, chloroacetyl, trichloroacetyl, o-nitrophenylacetyl, o-nitrophenoxyacetyl, trifluoroacetyl, acetoacetyl, 4-chlorobutyryl, isobutyryl, o-nitrocinnamoyl, picolinoyl, acylisothiocyanate, aminocaproyl, benzoyl and the like, and acyloxy, including methoxycarbonyl; 9-fluorenylmethoxycarbonyl; 2,2,2-trifluoroethoxycarbonyl; 2-trimethylsilylethxoycarbonyl; vinyloxycarbonyl; allyloxycarbonyl; tert-butoxycarbonyl (BOC); 1,1-dimethylpropynyloxycarbonyl; benzyloxycarbonyl (CBZ); p-nitrobenzyloxycarbony; 2,4-dichlorobenzyloxycarbonyl, and the like.

"Acid labile amine protecting group" means an amine protecting group as defined above which is readily removed by treatment with acid while remaining relatively stable to other reagents. A preferred acid labile amine protecting group is tert-butoxycarbonyl (BOC).

"Hydrogenation labile amine protecting group" means an amine protecting group as defined above which is readily removed by hydrogenation while remaining relatively stable to other reagents. A preferred hydrogenation labile amine protecting group is benzyloxycarbonyl (CBZ).

"Hydrogenation labile acid protecting group" means an acid protecting group as defined above which is readily removed by hydrogenation while remaining relatively stable to other reagents. A preferred hydrogenation labile acid protecting group is benzyl.

"Thiol protecting group" means a thiol protecting group that is readily removed by some reagents while being relatively stable to other reagents. The use of thiol protecting groups is well known in the art for protecting thiol groups against undesirable reactions during a synthetic procedure, and many such protecting groups are known; see, for example, T. H. Greene and P. G. M. Wuts, Protective Groups in Organic Synthesis, 2nd edition, John Wiley & Sons, New York (1991), the contents of which are hereby incorporated herein by reference. Exemplary thiol protecting groups are trityl (Trt), acetamidomethyl (Acm), and the like.

"Hydroxy protecting group" means a hydroxy protecting group that is readily removed by some reagents while being relatively stable to other reagents. The use of hydroxy protecting groups is well known in the art for protecting hydroxy groups against undesirable reactions during a synthetic procedure, and many such protecting groups are known; see, for example, T. H. Greene and P. G. M. Wuts, Protective Groups in Organic Synthesis, 2nd edition, John Wiley & Sons, New York (1991), the contents of which are hereby incorporated herein by reference. Exemplary hydroxy protecting groups are t-butyl, benzyl, tetrahydropyranyl, and the like.

Preferred Embodiments

A preferred embodiment of the invention is a method for treating a physiological condition capable of being modulated by inhibiting activity of Factor Xa by administering to a patient suffering from said physiological condition an effective amount of the compound of formula I.

A preferred embodiment of the invention is a method for treating a physiological condition capable of being modulated by directly inhibiting both Factor Xa and Factor IIa (thrombin), by administering to a patient suffering from said physiological condition an effective amount of the compound of formula I.

A preferred compound of the invention is a compound of formula I wherein n is 1.

A preferred compound aspect of the invention is a compound of formula I wherein W is H, lower alkyl, alkoxy, F or Cl.

A preferred compound aspect of the invention is a compound of formula I wherein R is aryl, heteroaryl or heterocyclyl; more preferably, R is substituted phenyl.

A preferred compound aspect of the invention is a compound of formula I wherein R is optionally substituted (phenyl substituted phenyl), optionally substituted (heteroaryl substituted phenyl), optionally substituted (phenyl substituted heteroaryl) or optionally substituted (heteroaryl substituted heteroaryl), (wherein the term "optionally substituted" before the term in the parenthesis, denote that the phenyl or heteroaryl portions thereof could be further substituted as noted per their definitions).

A preferred compound of the invention is a compound of formula I wherein W=H.

Another preferred compound aspect of the invention is the compound of formula I wherein $R^8$ is hydrogen.

Another preferred compound aspect of the invention is a compound of formula I wherein $R^2$ and $R^3$ taken together are $=NR^4$.

Another preferred compound aspect of the invention is a compound of formula I wherein $R^4$ is hydrogen or hydroxy; more preferably, $R^4$ is hydrogen.

Another preferred compound aspect of the invention is a compound of formula I wherein $R^5$ is alkyl; more preferably, $R^5$ is methyl.

Another preferred compound aspect of the invention is a compound of formula I wherein both $R^6$ and $R^7$ are hydrogen.

Another preferred compound of the invention is a compound of formula I wherein $L^1$ is alkylene; more preferably, $L^1$ is ethylene.

Another preferred compound aspect of the invention is the compound of formula I wherein $L^2$ is alkylene-C(O)— or alkylene-O—.

Another preferred compound aspect of the invention is the compound of formula I wherein $L^2$ is absent or alkylene.

Another preferred compound of the invention is a compound of formula I wherein $L^2$ is absent.

Another preferred compound of the invention is a compound of formula I wherein $X^1$ is O.

Another preferred compound aspect of the invention is a compound of formula I wherein Q is —$NR^8CO$—, —$CONR^8$—, —$NR^8SO_2$— or —$SO_2NR^8$—; more preferably, Q is —$NR^8CO$—

Another preferred compound aspect of the invention is a compound of formula I wherein both $R^8$ and $R^{8'}$ are hydrogen.

Another preferred compound of the invention is a compound of formula I wherein m is 2.

Included within the scope of formula I are compounds wherein $R^2$ and $R^3$ taken together are $=NR^4$, wherein $R^4$ is $R^5O_2C$—, $R^5O$—, cyano, $R^5CO$—, optionally substituted lower alkyl, nitro, or $R^6R^7N$—. Such derivatives may themselves comprise the biologically active compound useful for treating a physiological condition capable of being modulated by inhibiting activity of Factor Xa by its administration to a patient suffering from said physiological condition, or may act as pro-drugs to such biologically active compounds which are formed therefrom under physiological conditions.

Individual compounds according to the invention include the following:

5-(Pyridin-2-yl)-thiophene-2-carboxylic acid (2-[5-carbamimidoyl-2,3-dihydrobenzofuran-3-yl]ethyl)amide;
4-tert-Butyl-N-(2-[5-carbamimidoyl-2,3-dihydrobenzofuran-3-yl]ethyl)benzamide;
4-(2-Amino-1,1-dimethylethyl)-N-(2-[5-carbamimidoyl-2,3-dihydrobenzofuran-3-yl]ethyl)benzamide;
N-[2-(5-carbamimidoyl-2,3-dihydro-benzofuran-3-yl)-ethyl]-4-(3-amino-propyl)-benzamide;
N-[2-(5-carbamimidoyl-2,3-dihydro-benzofuran-3-yl)-ethyl]-2-(N-phenyl-amino)-benzamide;
N-[2-(5-carbamimidoyl-2,3-dihydro-benzofuran-3-yl)-ethyl]-2-(phenoxy)-benzamide;
N-[2-(5-carbamimidoyl-2,3-dihydro-benzofuran-3-yl)-ethyl]-4-(N,N-diethylamino)-benzamide;
N-[2-(5-carbamimidoyl-2,3-dihydro-benzofuran-3-yl)-ethyl]-4-(phenoxy)-benzamide;
N-[2-(5-carbamimidoyl-2,3-dihydro-benzofuran-3-yl)-ethyl]-2-methyl-3-phenyl-prop-2-enoic acid amide;
N-[2-(5-carbamimidoyl-2,3-dihydro-benzofuran-3-yl)-ethyl]-10-cyano-decanoic acid amide;
N-[2-(5-carbamimidoyl-2,3-dihydro-benzofuran-3-yl)-ethyl]-4-oxo-(4-methoxy-phenyl)-butyramide;
N-[2-(5-carbamimidoyl-2,3-dihydro-benzofuran-3-yl)-ethyl]-(1-methyl-pyrrole-2)-carboxamide;
N-[2-(5-carbamimidoyl-2,3-dihydro-benzofuran-3-yl)-ethyl]-(2,2-diphenyl)-propionamide;
N-[2-(5-carbamimidoyl-2,3-dihydro-benzofuran-3-yl)-ethyl]-(2-(4-chloro-phenoxy)-2-methyl-propionamide;
N-[2-(5-carbamimidoyl-2,3-dihydro-benzofuran-3-yl)-ethyl]-(2-[4-phenyl]-phenyl)-acetamide;
N-[2-(5-carbamimidoyl-2,3-dihydro-benzofuran-3-yl)-ethyl]-3-[3,4-dimethoxy-phenyl]-prop-2-enoic acid amide;
N-[2-(5-carbamimidoyl-2,3-dihydro-benzofuran-3-yl)-ethyl]-(5-oxo-5-phenyl-pentanoic acid) amide;
N-[2-(5-carbamimidoyl-2,3-dihydro-benzofuran-3-yl)-ethyl]-xanthine-9-carboxamide;
5-[1,2] dithiolan-3-yl-pentanoic acid-N-[2-(5-carbamimidoyl-2,3-dihydro-benzofuran-3ethyl]-amide;
N-[2-(5-carbamimidoyl-2,3-dihydro-benzofuran-3-yl)-ethyl]-5-methoxy-indole-2 carboxamide;
N-[2-(5-carbamimidoyl-2,3-dihydro-benzofuran-3-yl)-ethyl]-3,4-methylenedioxy cinnamic acid amide
N-[2-(5-carbamimidoyl-2,3-dihydro-benzofuran-3-yl)-ethyl]-3-quinoline carboxamide;
2,3-Dihydro-benzo[1,4]-dioxine-2-carboxylic acid-N-[2-(5-carbamimidoyl-2,3-dihydro-benzofuran-3-yl)-ethyl]-amide;
N-[2-(5-carbamimidoyl-2,3-dihydro-benzofuran-3-yl)-ethyl]-(2-[4-cyano-phenoxy]-2-methyl-propionamide;
N-[2-(5-carbamimidoyl-2,3-dihydro-benzofuran-3-yl)-ethyl]-2-(4-oxo-3,4-dihydro-pthalazin-1-yl)-acetamide;
3-Methyl-sulfanyl-4-oxo-4,5,6,7-tetrahydro-benzo[c]-thiophene-1-carboxylic acid N-[2-(5-carbamimidoyl-2,3-dihydro-benzofuran-3-yl)-ethyl]-amide;
4,5-Dimethyl-1-phenyl-pyrrole-3-carboxylic acid N-[2-(5-carbamimidoyl-2,3-dihydro-benzofuran-3-yl)-ethyl]-amide;
4-Oxo-4H-9-thia-1,4a-diaza-fluorene-3-carboxylic acid N-[2-(5-carbamimidoyl-2,3-dihydro-benzofuran-3-yl)-ethyl]-amide;
6-(1-pyrazole)-nicotinic acid N-[2-(5-carbamimidoyl-2,3-dihydro-benzofuran-3-yl)-ethyl]-amide;
3-Nitro-4-(1-pyrazolyl)benzoic acid N-[2-(5-carbamimidoyl-2,3-dihydro-benzofuran-3-yl)-ethyl]-amide;
N-Tosyl-3-pyrrole-carboxylic acid N-[2-(5-carbamimidoyl-2,3-dihydro-benzofuran-3-yl)-ethyl]-amide;
4-oxo-4,5,6,7-tetrahydro-benzofuran-3-carboxylic acid [2-(5-carbamimidoyl-2,3-dihydro-benzofuran-3-yl)-ethyl]-amide;
4-tert-butyl-2,6-dimethyl-cyclohexanecarboxylic acid [2-(5-carbamimidoyl-2,3-dihydro-benzofuran-3-yl)-ethyl]-amide;
5-methyl-1-(3-trifluoromethyl-phenyl)-4,5-dihydro-1H-1,2,3-triazole-4-carboxylic acid [2-(5-carbamimidoyl-2,3-dihydro-benzofuran-3-yl)-ethyl]-amide;
2-benzylsulfanyl-N-[2-(5-carbamimidoyl-2,3-dihydro-benzofuran-3-yl)-ethyl]-propionamide;
5-pyridin-2-yl-thiophene-2-carboxylic acid [2-(5-carbamimidoyl-2,3-dihydro-benzofuran-3-yl)-ethyl]-amide;
4-butyl-cyclohexanecarboxylic acid [2-(5-carbamimidoyl-2,3-dihydro-benzofuran-3-yl)-ethyl]-amide;
5-methyl-1-phenyl-1H-pyrazole-4-carboxylic acid [2-(5-carbamimidoyl-2,3-dihydro-benzofuran-3-yl)-ethyl]-amide;
N-[2-(5-carbamimidoyl-2,3-dihydro-benzofuran-3-yl)-ethyl]-6-pyrrol-1-yl-nicotinamide;
4-chloro-1,3-dimethyl-1H-pyrazolo[3,4-b]pyridine-5-carboxylic acid [2-(5-carbamimidoyl-2,3-dihydro-benzofuran-3-yl)-ethyl]-amide;
4-methyl-2-(4-trifluoromethyl-phenyl)-thiazole-5-carboxylic acid [2-(5-carbamimidoyl-2,3-dihydro-benzofuran-3-yl)-ethyl]-amide;
(S)-2-(6-Methoxynaphthyl)-N-(2-[5-carbamimidoyl-2,3-dihydrobenzofuran-3-yl]ethyl)propionamide;
N-(2-[5-Carbamimidoyl-2,3-dihydrobenzofuran-3-yl]ethyl)-3-chlorobenzothiophene-2-carboxamide;
4-Benzyloxy-N-(2-[5-carbamimidoyl-2,3-dihydrobenzofuran-3-yl]ethyl)benzamide;
4-(4-n-Propylphenyl)-N-(2-[5-carbamimidoyl-2,3-dihydrobenzofuran-3-yl]ethyl)benzamide;
2-Methylthio-N-(2-[5-carbamimidoyl-2,3-dihydrobenzofuran-3-yl]ethyl)benzamide;
3-(4-Pyridyl)-N-(2-[5-carbamimidoyl-2,3-dihydrobenzofuran-3-yl]ethyl)acrylamide;
N-(2-[5-Carbamimidoyl-2,3-dihydrobenzofuran-3-yl]ethyl)-4-tert-butylcyclohexanecarboxamide;
N-(2-[5-Carbamimidoyl-2,3-dihydrobenzofuran-3-yl]ethyl)-5-methylindole-2-carboxamide;
N-(2-[5-Carbamimidoyl-2,3-dihydrobenzofuran-3-yl]ethyl)quinoline-6-carboxamide;
N-(2-[5-Carbamimidoyl-2,3-dihydrobenzofuran-3-yl]ethyl)benzothiophene-2-carboxamide;
2-Pyrrolyl-N-(2-[5-carbamimidoyl-2,3-dihydrobenzofuran-3-yl]ethyl)benzamide;
4-Methyl-2-phenyl-N-(2-[5-carbamimidoyl-2,3-dihydrobenzofuran-3-yl]ethyl)-1,2,3-triazole-5-carboxamide;
N-(2-[5-Carbamimidoyl-2,3-dihydrobenzofuran-3-yl]ethyl)-phthalide-3-acetamide;
N-[2-(5-Carbamimidoyl-2,3-dihydro-Benzofuran-3-yl)-ethyl]-4-(phenyl)-benzamide;
N-[2-(5-Carbamimidoyl-2,3-dihydro-Benzofuran-3-yl)-ethyl]-4-(pyridin-3-yl)-benzamide;
4-(1-Aminomethyl-cyclopentyl)-N-[2-(5-carbamimidoyl-2,3-dihydro-benzofuran-3-yl)-ethyl]-benzamide;
N-[2-(5-carbamimidoyl-2,3-dihydro-Benzofuran-3-yl)-ethyl]-4-(pyridine-N-oxid-3-yl)-benzamide;

N-[2-(5-carbamimidoyl-2,3-dihydro-Benzofuran-3-yl)-ethyl]-4-(pyridin-4-yl)-benzamide;
N-[2-(5-carbamimidoyl-2,3-dihydro-Benzofuran-3-yl)-ethyl]-4-(6-oxo-1,6-dihydro-pyridin-3-yl)-benzamide;
N-[2-(5-carbamimidoyl-2,3-dihydro-Benzofuran-3-yl)-ethyl]-4-[(3-(aminomethyl)-phenyl]-benzamide;
N-[2-(5-carbamimidoyl-2,3-dihydro-Benzofuran-3-yl)-ethyl]-4-(pyridazin-3-yl)-benzamide;
N-[2-(5-carbamimidoyl-2,3-dihydro-Benzofuran-3-yl)-ethyl]-4-(pyridazin-4-yl)-benzamide;
N-[2-(5-carbamimidoyl-2,3-dihydro-Benzofuran-3-yl)-ethyl]-4-(pyrimidin-5-yl)-benzamide;
N-[Biphenyl-4-yl-methyl]-2-(5-carbamimidoyl-2,3-dihydro-benzofuranyl) acetamide;
N-[Biphenyl-4-yl]-2-(5-carbamimidoyl-2,3-dihydro-benzoturanyl) acetamide;
3-(3-Biphenyl-4-ylmethyl-ureido-methyl)-2,3-dihydrobenzofuran-5-carboxamidine;
3-[2-(4-Benzyl-piperidin-1-yl-2-oxo-ethyl]-2,3-dihydro-benzofuran-5-carboxamidine;
3-{2-[4-(1,1-Dimethylpropyl)benzenesulfonylamino] ethyl}-5-carbamimidoyl-2,3-dihydrobenzofuran; and
3-[2-(7-Chlorobenzo[1,2,5]oxadiazole-5-sulfonylamino) ethyl]-5-carbamididoyl-2,3-dihydrobenzofuran.

More preferred species according to the invention are compounds:
5-(Pyridin-2-yl)-thiophene-2-carboxylic acid (2-[5-carbamimidoyl-2,3-dihydrobenzofuran-3-yl]ethyl)amide;
4-tert-Butyl-N-(2-[5-carbamimidoyl-2,3-dihydrobenzofuran-3-yl]ethyl)benzamide;
4-(2-Amino-1,1-dimethylethyl)-N-(2-[5-carbamimidoyl-2,3-dihydrobenzofuran-3-yl]ethyl)benzamide;
N-[2-(5-carbamimidoyl-2,3-dihydro-benzofuran-3-yl)-ethyl]-4-(3-amino-propyl)-benzamide;
N-[2-(5-Carbamimidoyl-2,3-dihydro-Benzofuran-3-yl)-ethyl]-4-(phenyl)-benzamide;
N-[2-(5-Carbamimidoyl-2,3-dihydro-Benzofuran-3-yl)-ethyl]-4-(pyridin-3-yl)-benzamide;
(1-Aminomethyl-cyclopentyl)-N-[2-(5-carbamimidoyl-2,3-dihydro-Benzofuran-3-yl)-ethyl]-benzamide;
N-[2-(5-carbamimidoyl-2,3-dihydro-Benzofuran-3-yl)-ethyl]-4-(pyridine-N-oxid-3-yl)-benzamide;
N-[2-(5-carbamimidoyl-2,3-dihydro-Benzofuran-3-yl)-ethyl]-4-(pyridin-4-yl)-benzamide;
N-[2-(5-carbamimidoyl-2,3-dihydro-Benzofuran-3-yl)-ethyl]-4-(6-oxo-1,6-dihydro-pyridin-3-yl)-benzamide;
N-[2-(5-carbamimidoyl-2,3-dihydro-Benzofuran-3-yl)-ethyl]-4-[(3-(aminomethyl)-phenyl]-benzamide;
N-[2-(5-carbamimidoyl-2,3-dihydro-Benzofuran-3-yl)-ethyl]-4-(pyridazin-3-yl)-benzamide;
N-[2-(5-carbamimidoyl-2,3-dihydro-Benzofuran-3-yl)-ethyl]-4-(pyridazin-4-yl)-benzamide; and
N-[2-(5-carbamimidoyl-2,3-dihydro-Benzofuran-3-yl)-ethyl]-4-(pyrimidin-5-yl)-benzamide.

It is to be understood that this invention covers all appropriate combinations of the particular and preferred groupings referred to herein.

Compounds of formula I may be prepared by the application or adaptation of known methods, by which is meant methods used heretofore or described in the literature, or by methods according to this invention as described herein.

As used herein the following reagents, solvents and terms are identified by the abbreviations indicated:
Acetic acid (ACOH or HOAc); acetic anhydride ($Ac_2O$); acetamidomethyl (Acm); benzyl (Bn); t-Butoxycarbonyl (Boc); 2-(4-Biphenylyl)-prop-2-yl 4'-methoxycarbonylphenyl carbonate (Bpoc); benzyl carbamate (CBZ); n-butyl lithium (n-BuLi), cerium ammonium nitrate (CAN); cyclopropyl (Cp); 1,5-diazabicyclo[4.3.0]nona-5-ene (DBN); 1,8-diazabicyclo[5.4.0]undec-7-ene (DBU); dichloromethane (DCM); diethylazodicarboxylate (DEAD); dicyclohexicarbodiimide (DCC); diisobutylaluminum hydride (DIBAL); N,N-Diisopropyl-carbodiimide (DIC), diisopropylethylamine (DIEA); N,N-dimethylaniline (DMA);
1,2-Dimethoxyethane (DME); N,N-dimethylformamide (DMF); diethyl azodicarboxylate (DEAD); 4-dimethylaminopyridine (DMAP); 1,3-dimethyl-3,4,5,6-tetrahydro-2(1H)-pyrimidinone (DMPU); dimethylsulfoxide (DMSO); N-ethyloxycarbony-2-ethyloxy-1,2-dihydroquinone (EEDQ), equivalent (eq.); ethyl (Et); ethanol (EtOH); diethyl ether ($Et_2O$); triethylamine ($Et_3N$); ethyl acetate (EtOAc); 1-(3-dimethylaminopropyl)-3-ethyl-carbodiimide-hydrochloride (EDC); hexamethylphosphoramide (HMPA); fast atom bombardment (FAB); 2-furanmethyloxycarbonyl (Foc), acetic acid (HOAc); high-performance liquid chromatography (HPLC); di-isopropylethylamine (Hunigs base); O-(7-azabenzotriazol-1-yl-1,1,3,3-tetramethylur onium hexafluorophosphate (HATU); O-(7-azabenzotriazol-1-yl-1,1,3,3-bis (tetramethylene uronium hexafluorphosphate (HApyU), O-(7-azabenzotriazol-1-yl)-1,1,3,3-bis (pentamethylene) uronium hexafluorophosphate (HApipU), O-(7-azabenzo-trizol-1-yl)-1,3-dimethyl-1,3-trimethylene uronium hexafluorophosphate (HAMTU); iso-propylacetate (iPrOAc); O-benzotriazolyl-1-yl-1,1,3,3-tetramethyluronium hexafluoro-phosphate(HBTU); 1-Hydroxybenzotriazole hydrate (HOBT); iso-propanol (iPrOH); potassium bis(trimethylsilyl)amide (KHMDS); lithium bis(trimethylsilyl)amide (LHMDS); methyl (Me); methanol (MeOH); m-chloroperoxybenzoic acid (MCPBA); methanesulfonyl chloride (mesyl chloride or MsCl); p-ethoxybenzyloxycarbonyl (Moz); sodium bis (trimethylsilyl)amide (NaHMDS); N-methylpyrrolidine (NMP); phenyl (Ph); Pyridine (Py); room temperature (r.t.); t-butyl methyl ether (TBME); benzotriazolyl-yl-1,1,3,3-bis (tetramethylene uronium tetrafluoroborate) (TBTU); 2-(trimethylsilyl)ethyl carbonate(TEOC); tetrahydrofuran (THF); trifluoroacetic acid (TFA); tetramethylethylene diamine (TMEDA); trimethylsilane (TMS); p-toluenesulfonyl chloride (tosyl chloride or TsCl); ); p-toluenesulfonic acid (TsOH); trityl (Trt), and p-toluenesulfonic acid (p-TSA).

The practice of this invention involves the synthesis of variously substituted dihydrobenzofurans and benzopyrans. In principle, this can be achieved by functionalization of specific precursors followed by ring synthesis or by derivatization of a preformed ring system. There are numerous approaches to the synthesis and functionalization of the aforementioned heterocycles in the chemical literature. For examples, see Katritzky, A. R.; Rees, C. W.; Scriven, E. F. V. Eds. *Comprehensive Heterocyclic Chemstry II,* Vol 2 and Vol 5. Elsevier Science 1996 and references cited therein. A particularly useful synthetic protocol with regard to the current invention is outlined in Scheme 1.

Scheme 1

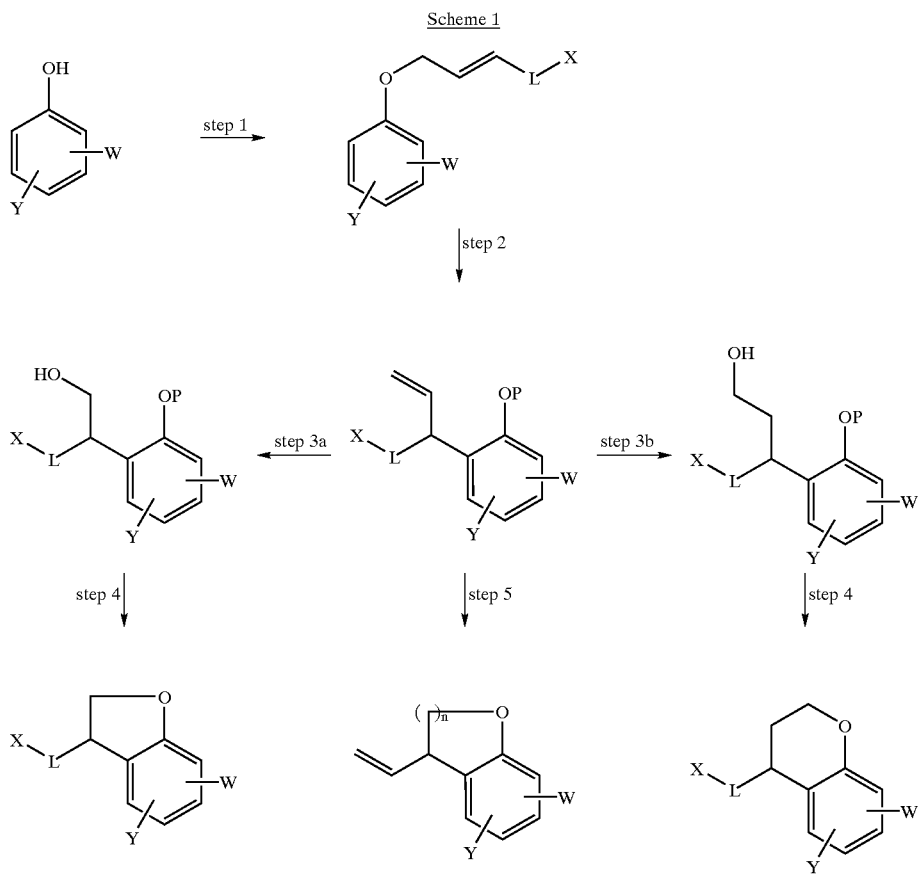

X = Hydroxyl, protected hydroxyl, amine or protected amine.
Y = H, Br, CN or CHO In this approach, the requisite heterocyclic ring is constructed from a substituted phenol by (1) formation of an allylic-aryl ether. (2) Claisen rearrangement of this allylic ether to provide the corresponding olefin substituted phenol. (Lutz, R. P. *Chem. Rev.* 1984, 84, 205. In certain instances, it may be convenient to protect the phenolic hydroxyl with a temporary protecting group at this stage.) (3) Conversion of the olefin into an alcohol, alkyl halide or sulphonate. (4) Ring closure of the resulting product (after deprotection of the phenol where applicable).

Formation of an aryl allyl ether from a phenol can be effected using standard phenol alkylation conditions employing a base, such as sodium hydride THF, DME, DMPU, DMF, DMSO, HMPA or potassium carbonate, in a solvent such as THF, DME, DMPU, DMF, DMSO, HMPA, or a mixture thereof and an appropriate allylic halide or sulphonate. Alternatively, this transformation can be carried out by Mitsunobu etherification (Mitsunobu. O., *Synthesis*, 1981, 1) of a phenol with an appropriate allylic alcohol.

Synthesis of the requisite allylic alcohols/halides/sulphonates can be carried out using standard functional group transformations (see Larock, C. L. *Comprehensive Organic Transformations*, VCH Publishers 1989) such as outlined in Scheme 2.

Scheme 2

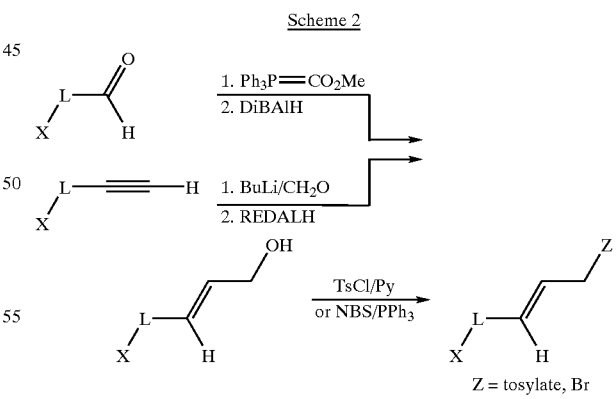

Z = tosylate, Br

Conversion of an olefin into an alcohol can be carried out either by a standard hydroboration oxidation sequence (step 3a, Scheme 1). For examples, see (a) Beletskaya, I; Pelter, A. *Tetrahedron*, 1997, 53, 4957 and references cited therein; (b) Brown, H. C.; Kramer, G. W.; Levy, M. B.; Midland, M. M., *Organic Synthesis via Boranes*, Wiley Interscience, N.Y. 1973] or by oxidative cleavage of the olefin with a reagent such as ozone in dichloromethane followed by reduction of the resulting ozonide with sodium borohydride in methanol (step 3b, Scheme 1). In situations where the use of ozone is inconvenient, oxidative cleavage of the olefin linkage can also be effected with a reagent such as catalytic osmium tetroxide/sodium periodate in a solvent such as t-butanol/water or THF/water, at about room temperature. Conversion of an alcohol into the corresponding sulphonate can be carried out by treatment with, for example, toluenesulphonyl chloride/DMAP and a base such as triethylamine or diisopropylethylamine in a solvent such as dichloromethane, DMF or pyridine at or around room temperature. The corresponding halide can be installed by treatment of the alcohol with a reagent system such as $NBS/Ph_3P$, $NCS/Ph_3P$, $I_2/Ph_3P$/imidazole, $CBr_4/Ph_3P$. For a review, see Castro, B. R. *Org. React.,* 1983, 29, 1). Ring closure can be effected on a phenol by Mitsunobu etherification or on a phenolic sulphonate or halide using the standard phenolic alkylation conditions described above.

Clearly, in situations where —L—X is, or can be converted to, $(CH_2)_nOH$, this residue can also be used to effect ring closure (Scheme 1, step 5) and generate a heterocycle with an olefin side chain.

An alternative approach to benzopyrans and dihydrobenzofurans entails the use of an ortho-iodo-phenyl ether as a heterocyclic precursor (Scheme 3). Ring closure is initiated by metal halogen exchange using a reagent such as BuLi in THF or ether, generally at a low temperature, such as −78° C. to −100° C. The requisite aryl ethers for this approach can be prepared by alkylation of the ortho-iodo-phenol with a g-bromo but-2-enoate, such as methyl 4-bromo-crotonate, or by Mitsunobu etherification with a 5-hydroxy-pen-2-enoate (Gabriele, B.; Salerno, G.; Costa, M.; Chiusoli, Gian P. *J. Mol. Catal. A: Chem.,* 1996, 111, 43).

Scheme 3

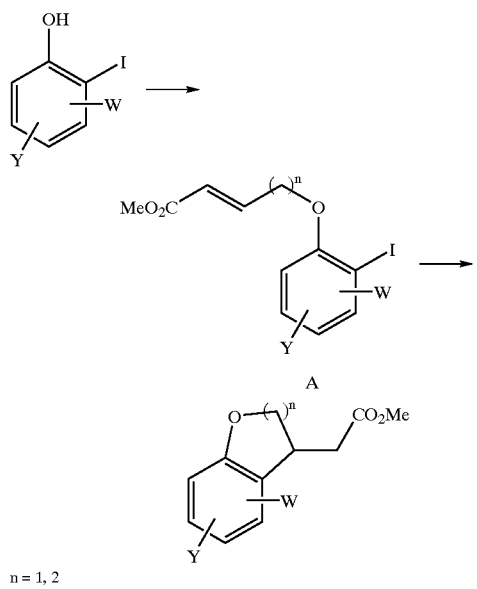

n = 1, 2

Ring closure of an iodo-alkene such as A (scheme 3) can also be effected under free radical conditions using a reagent such as tributyl tin hydride in a solvent such as benzene at a temperature above about 55° C. in the presence of an initiator such as AIBN (2,2'-Azobixixobutyronitrile) or benzoyl peroxide.

The heterocyclic side chains incorporated as described above can contain, or be converted to, a variety of functional groups (using one or more steps) including amines, alcohols, aldehydes, ketones, carboxylic acids, esters, olefins, amides, imides, urethanes, carbamates, sulphonamides, sulphones, sulphoxides and sulfides. These interconversions employ standard synthetic methods described in the chemical literature. (For example, see Larock, C. L. *Comprehensive Organic Transformations,* VCH Publishers 1989 and Greene, T. W.; Wuts, P. G. M. *Protective Groups in Organic Synthesis,* John Wiley Publications 1991). In particular, an alcohol in the side chain can be converted to the corresponding amine by a sequence (Scheme 4) involving (1) formation of a sulphonate or halide derivative as described above. (2) Reaction of this product with sodium azide in a solvent such as DMF, dimethyl acetamide, DMPU or ethanol at a temperature between 20 and 80° C. and (3) reduction of the resulting azide with a reagent such as triphenylphosphine/water in THF or, alternatively, boron trifluoride etherate/1,3-propane-dithiol in a solvent such as dichloromethane.

Scheme 4

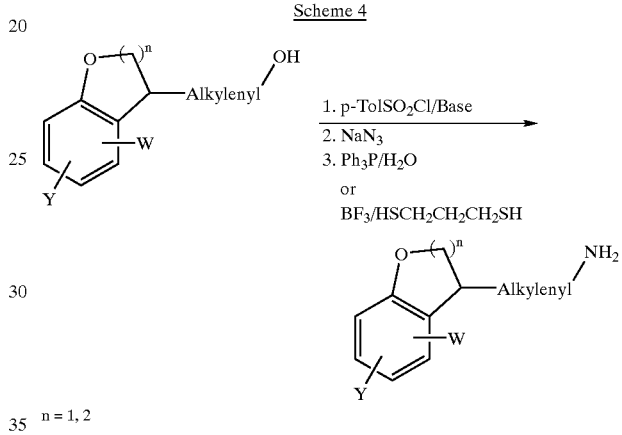

n = 1, 2

An amino functionality can also be introduced into the heterocycle side chain (Scheme 5) by conversion of an appropriate side chain alkene, first to an alcohol, using a hydoboration oxidation sequence, as previously described, then oxidation of the alcohol to the corresponding ketone using any of a number of common oxidation reagents such as Swern's reagent. (For a review, see Hudlicky, T. *Oxidations in Organic Chemistry,* ACS Publications 1990). This is followed by reductive amination of the ketone (Abdel-Magid, A. F.; Maryanoff, C. A. *Reductions in Organic Synthesis,* ACS Symp. Ser., 641, p201, ACS Publications 1996) with an appropriate amine and a reducing agent, such as sodium cyanoborohydride or sodium triacetoxyborohydride, in a solvent such as methanol, THF, acetonitrile, HMPA, or water, either alone or as co-solvents. In certain cases, the amine functionality may be part of the heterocyclic side chain, in which case, a ring will be formed, which ring contains a secondary or tertiary amine).

Scheme 5

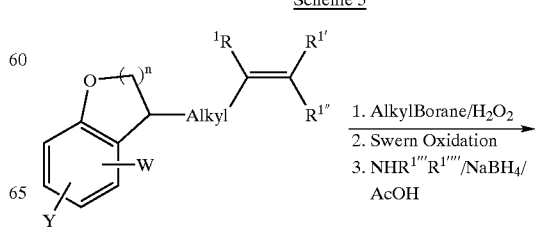

-continued

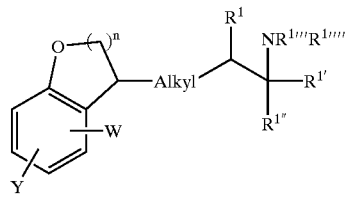

n = 1, 2

Another convenient method for introduction of an amino functionality into the side chain involves treatment of a side chain carboxylic acid with diphenylphosphoryl azide and a base, such as triethylamine or diisopropylamine, in a solvent, such as dichloromethane, THF, toluene or benzene, at a temperature usually between 0° C. and room temperature. (For a review, see Banthrope, *The Chemistry of the Azido Group*, S. Patai Ed. Wiley Interscience N.Y. 1971.) Subsequent thermolysis of the resulting acyl azide (at room temperature to 140° C.) in the presence of an alcohol, such as t-butanol, benzyl alcohol or allyl alcohol, provides the corresponding carbamate, which can be cleaved to the amine using standard protecting group chemistry. Thermolysis of the acyl azide in the absence of an alcohol produces the corresponding isocyanate, which can be reacted subsequently with a variety of amines to provide urethanes. (For a modification that also provides a convenient preparation of secondary amines, see Pfister, J. R.; Wymann, W. E. *Synthesis*, 1983, 38.) Alternatively, a urethane can be incorporated by reaction of a side chain amino functionality with an appropriate isocyanate. An imide functionality can be introduced by reaction of a side chain alcohol with a preformed, N-unsubstituted-imide using Mitsunobu's reagent (Mitsunobu. O., *Synthesis*, 1981, 1) The imide, so formed, can also be converted to the corresponding amine by treatment with hydrazine in a solvent such as ethanol. Alternatively, the imide group can be introduced by acylation of a side chain amide with an acid choride (or an activated ester) in the presence of a base such as sodium hydride.

An amide linkage can be introduced into the heterocycle side chain by reaction of an amine (introduced using a method such as described above) with a carboxylic acid. Suitable conditions for effecting this transformation involve activation of the acid with a reagent, such as thionyl chloride, isopropyl chloroformate, oxalylchloride/DMF, TBTU, DCC, DICC/HOBT, CDI, BOP, EEDQ or PyBroP, usually in the presence of a base, such as triethylamine, diisopropyl-ethylamine and/or DMAP. in a solvent, such as dichloromethane, DMF, dimethylacetamide or DMPU, at or above room temperature (For reviews see (a) Blackburn, C.; Kates, S. A. *Methods Enzymol.* 1997, 289, 175. (b) Bodanszky, M.; Trost, B. M. *Principles of Peptide Synthesis* 2nd Ed., Springer Verlag, N.Y. 1993). The reverse orientation of the amide unit can be prepared by reaction of an heterocycle side chain, containing an acid functionality, with an amine. An acid functionality can be formed in the side chain by oxidation of a side chain alcohol, first to the aldehyde, followed by oxidation of the aldehyde to the corresponding carboxylic acid. A particularly suitable reagent for this transformation is sodium chlorate (Lidgren, B. O.; Hilsson, T. *Acta. Chem. Scand.* 1973, 58, 238). Alternatively, an aldehyde can be generated by oxidation of an olefin, using osmium tetroxide with a co-catalyst, such as sodium periodate, in a solvent, such as THF/water or t-butanol/water. A carboxylic acid can also be obtained by cleavage of an appropriate ester according to standard protecting group methodology. A sulphonamide linkage can be introduced into the side chain by reaction of a side chain amino functionality with a sulphonyl chloride in the presence of a base, such as pyridine, triethylamine, diisopropylethylamine or sodium hydroxide, in a solvent, such as dichloromethane, pyridine, DMF or an alcohol such as ethanol or iso-propanol. The reverse orientation of the sulphonamide linkage can be produced by the method of Liskamp (Moree, W. J.; Van der Marel, G. A.; Liskamp, R. J. *J. Org. Chem.* 1995, 60, 1995) from a side chain thioacetate. The thioacetate functionality can be prepared by displacement of a halide or sulphonate with sodium thioacetate in a solvent, such as DMF, DMPU, HMPA or DMSO.

A sulphide linkage can be incorporated into the side chain by saponification of the thioacetate fuctional group, followed by alkylation of the resulting thiol with an appropriate alkyl halide or sulphonate (such as tosylate, triflate or mesylate). Alternatively, the sulphide linkage can be incorporated by direct reaction of a side chain alkyl chloride, bromide, iodide, tosylate or mesylate with a thiolate ion in a solvent, such as benzene, DMF, DMPU, HMPA or DMSO. In certain cases, a sulphide can be formed from an appropriate disulphide and a side chain alcohol in the presence of tributylphosphine in a solvent such as THF. The corresponding side chain sulphoxide and sulphone functionalities can be introduced by mild oxidation of the sulphides with an oxidizing reagent, such as m-chloroperbenzoic acid in dichloromethane chloroform or benzene at or below room temperature.

An ether linkage can be prepared from reaction of a side chain alcohol with an alkyl halide, sulphonate or $\alpha,\beta$-unsaturated ketone and a base, such as sodium hydride potasium hydride, in a solvent, such as DMF, DMSO, THF, DMPU or HMPA (for a review see *Comprehensive Organic Chemistry* Vol 1, p 799, Ed. Barton, D.; Ollis, W. D., Pergamon Press, 1979). Alternatively, an ether linkage can be obtained using a side chain alkyl halide, sulphonate or $\alpha,\beta$-unsaturated ketone and an appropriate alcohol under the same conditions. Another method of ether formation involves formation of a thiono-ester from a side chain ester or lactone by reaction with a thionating reagent, such as Lawesson's reagent (for a review see Cava, M. P.; Levinson, M. I. *Tetrahedron*, 1985, 41, 5061), followed by reduction of the thiono group with a hydride reducing agent, such as tributyltin hydride, usually in the presence of a free radical initiater, such as AIBN.

Introduction of a nitrile can be achieved by conversion of an aldehyde to the corresponding oxime by reacting the aidehyde with hydroxylamine hydrochloride (Scheme 6) in a solvent, such as DMF, toluene or xylene, in the presence of a catalyst, such as toluene sulphonic acid and a desiccant, such as magnesium sulphate according to the method of Ganbao and Palomo (Ganbao, I.; Palomo, C. *Syn. Commun.* 1983, 13, 219. For alternatives to this procedure see Wang, E-C.; Lin, G-J. *Tetrahedron Lett.* 1998, 39, 4047 and references therein) The heating of the oxime with these reagents at a temperature between about 80° C. and 150° C. then results in dehydration to form the corresponding nitrile.

Scheme 6

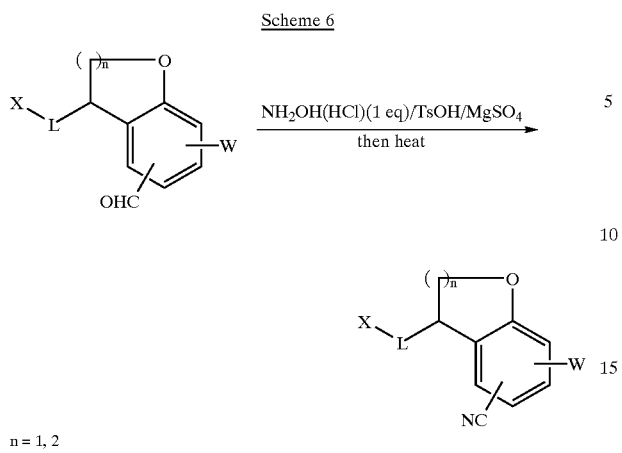

n = 1, 2

Introduction of a nitrile group para to the oxygen functionality of the heterocyclic ring can be effected by a sequence (Scheme 7) involving treatment with bromine in a solvent, such as acetic acid or chloroform. The resulting aryl bromide can then be converted to the corresponding-cyano-derivative using zinc cyanide and a palladium catalyst, preferably tetrakis(triphenylphosphine) palladium(o) in DMF at a temperature between 70–90° C. (Tschaen; D. M.; Desmond, R.; King, A. O.; Fortin, M. C.; Pipik, B.; King, S.; Verhoeven, T. R. *Syn. Commun.*, 1994, 24, 887). This conversion can also be effected using copper cyanide in a solvent such as DMF, at elevated temperatures generally greater than 120° C. (Ellis, G. P.; Romney-Alexander, T. M.; *Chem. Rev.*, 1987, 87, 779).

Scheme 7

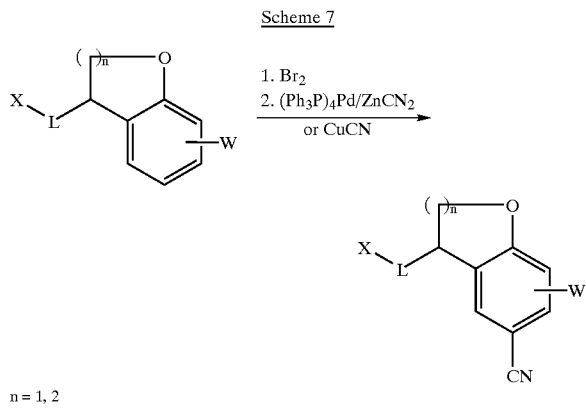

n = 1, 2

A particular embodiment of the current invention employs dihydrobenzofurans and benzopyrans substituted with a side chain that contains a bi-aromatic moiety, for example a biaryl, biheteroaryl, an aryl group substituted with a heteroaryl group, or an heteroaryl group substituted with an aryl group. bi-aromatic moieties can be prepared by cross coupling (Scheme 8) of an appropriately substituted aryl (or heteroaryl) halide or aryl (or heteroaryl) triflates with an aryl (or heteroaryl) organometallic (most commonly zinc, boron, magnesium or tin derivative) under catalysis by Pd(O) or Ni(O). For examples of such cross coupling reactions and conditions, see Tsuji, J. Palladium Reagents and Catalysts, J. Wiley Publications, 1996.

Scheme 8

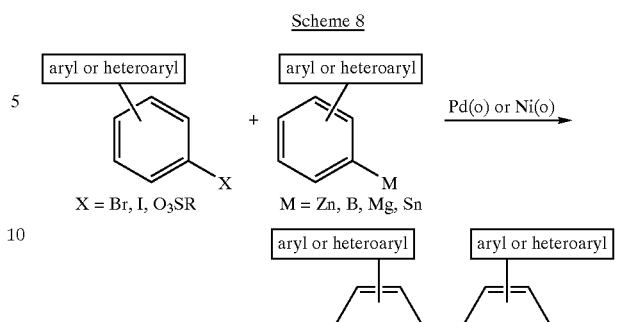

Aryl and heteroaryl substituted heterocycles can also be prepared by direct ring synthesis. A wide variety of methods and conditions for this kind of process are known in the chemical literature (for example, see Katritzky, A. R.; Rees, C. W.; Scriven, E. F. V. Eds. Comprehensive Heterocyclic Chemstry II, Elsevier Science 1996).

In another embodiment of this invention the dihydrobenzofuran/benzopyran side chain contains a substituted aryl group. One particularly useful aryl group substituent comprises a 1,1-dimethyl alkyl chain (FIG. 1) further substituted with a heteroatom functionality (such as an amine, amide, sulphonamide, carbamate or urethane), a heteroatom cluster (such as a diol or amino-alcohol) or a heterocycle (such as imidazole).

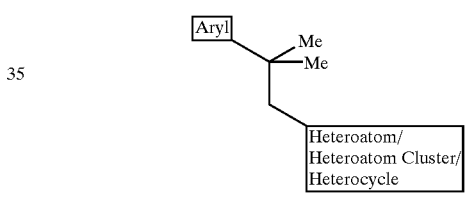

These systems can be prepared from 2-(4-furan-2-ylphenyl)-2-methylpropionic acid methyl ester, 2-(4-bromophenyl)-2-methylpropionic acid methyl ester (see experimental section) or 4-bromophenyl acetonitrile as shown in Schemes 9 and 10. Specifically, treatment of 2-(4-furan-2-ylphenyl)-2-methylpropionic acid methyl ester (1, Scheme 9) with methyl lithium in the presence of lithium hexamethyldisilazide, at or below room temperature, and reaction of the resulting enolate with TMS chloride provides the corresponding silyl enol ether. Reaction of this intermediate with 1 eq of bromine at low temperature (typically –78° C.) furnishes the a-bromo-ketone (2). This compound can be treated with formamide at elevated temperatures (from about 50° C.–180° C.) to provide the corresponding imidazole (3). Alternatively, a-bromo ketone (2) can be reacted with sodium azide followed by reduction with sodium borohydride to provide the amino alcohol (5). After protection of the amino alcohol as a BOC derivative of the amine and a t-butyl di-methyl silyl ether (TBS ether) of the alcohol, the furan ring in (5) can be oxidatively cleaved to provide the benzoic acid derivative (6) using catalytic ruthenium trichloride/sodium periodate (a similar procedure can be used to prepare acid (4) from furan (3)). These benzoic acid units can then be attached to the dihydrobenzofuran or benzopyran scaffolds through amide bond formation as described above.

Scheme 9

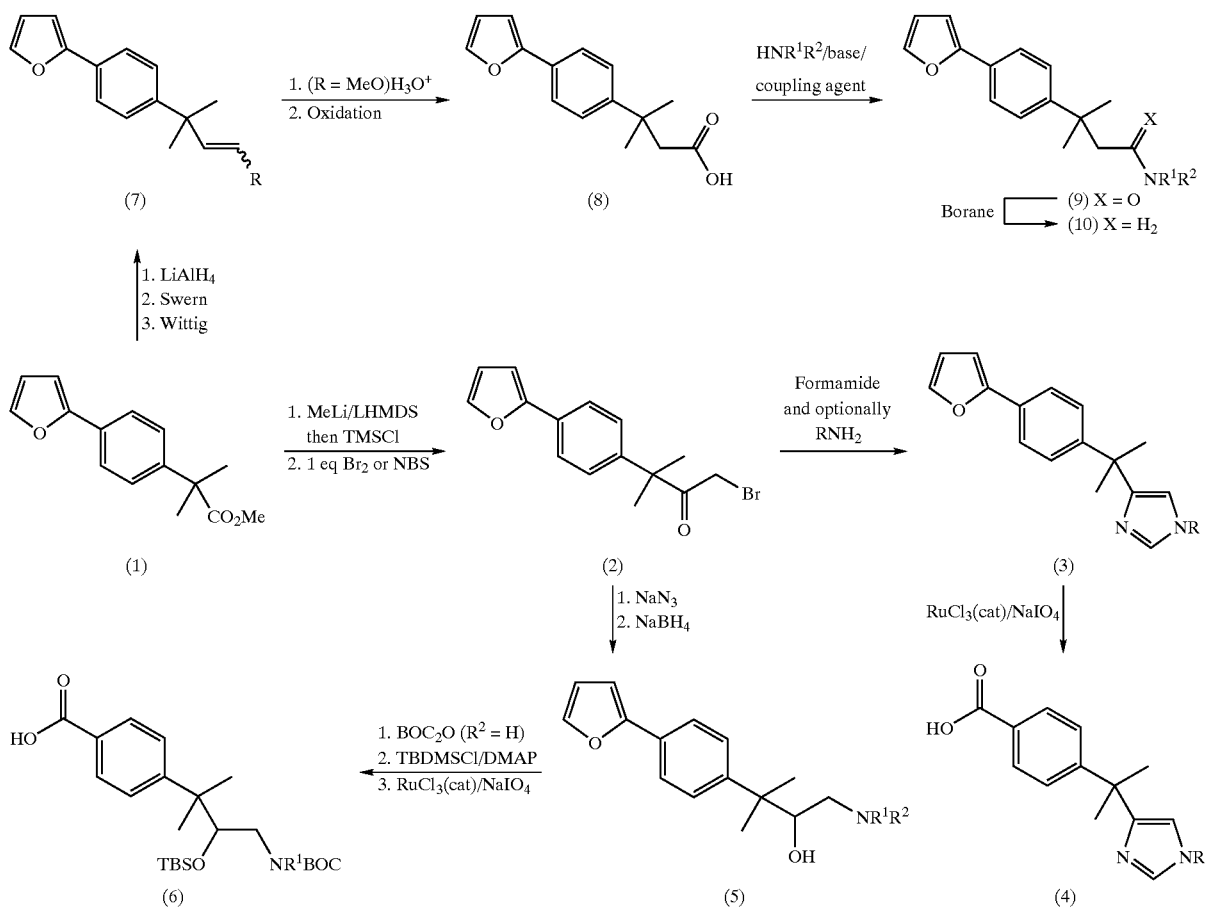

Additionally, The methyl ester in (1) can be converted to an olefin of general formula (7) employing a sequence involving reduction with lithium aluminum hydride in a solvent such as THF or ether followed by oxidation of the resulting primary alcohol to the corrsponding aldehyde and Wittig or Horner-Emmons olefination (For a review see Cadogan, J. I. G. *Organophosphorus Reagents in Organic Synthesis,* Academic Press, 1979). In the case of the olefin compound where R=OMe, this system can be hydrolysed to the corresponding aldehyde with dilute HCl then oxidized to the carboxylic acid (8) as previously described. Amide formation on (8) produces (9) that can be further reacted with a reagent such as borane in THF to provide the amines (10). Subsequent oxidative cleavage of the furan ring in these systems, as described above, provides the acid functional group that is then coupled to the heterocyclic scaffold.

Alternatively, (Scheme 10) treatment of 2-(4-bromophenyl)-2-methylpropionic acid methyl ester (11) with diisobutylaluminum hydride at −78° C. in dichloromethane followed by Swern oxidation of the resulting alcohol and Wittig reaction on the aldehyde provides the one carbon chain extended olefin (12). Osmylation of this species (12), followed by protection of the resulting diol as an acetonide (13) allows introduction of the carboxylic acid attachment point for coupling to the dihydrobenzofuran and benzopyran scaffolds.

Scheme 10

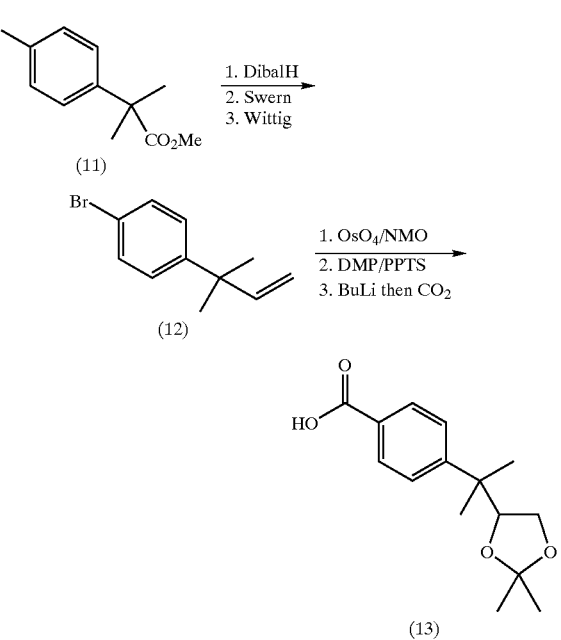

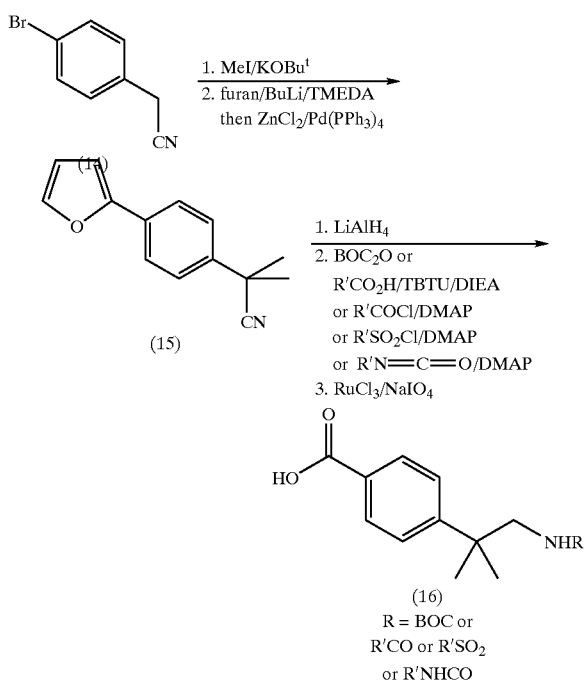

In addition, derivatized amine units such as (16) can be prepared from 4-bromophenyl acetonitrile (14) by a sequence involving methylation, then introduction of the furan to provide (15), reduction of the nitrile in (15) followed by amine derivatization with a carbonate, carboxylic acid, acid chloride, sulphonyl chloride or isonitrile and finally oxidative cleavage of the furan ring.

Certain preferred embodiments of this invention involve structures containing an amidine functional group. This group can be easily prepared from a nitrile (Scheme 11) employing a number of standard procedures. (for examples see Judkins, B. D.; Allen, D. G.; Cook, T. A.; Evans, B.; Sardharwala, T. E. *Syn. Comm.* 1996, 26, 4351 and references therein). In particular, treatment of the nitrile (17) with HCl in a solvent such as methanol or ethanol at a temperature at or above room temperature provides the imidate ester intermediate which can then be converted to the amidine (18) by treatment with ammonia or an alkylamine in a solvent such as methanol or ethanol. Alternatively, reaction of the nitrile with hydrogen sulphide in a solvent such as pyridine, followed by alkylation of the resulting thioamide with an alkylating agent such as methyl iodide in a solvent such as acetone at a temperature at or above room temperature and treatment of this product with ammonia or ammonium acetate in a solvent such as methanol at or above room temperature provides the final amidine (18).

Scheme 11

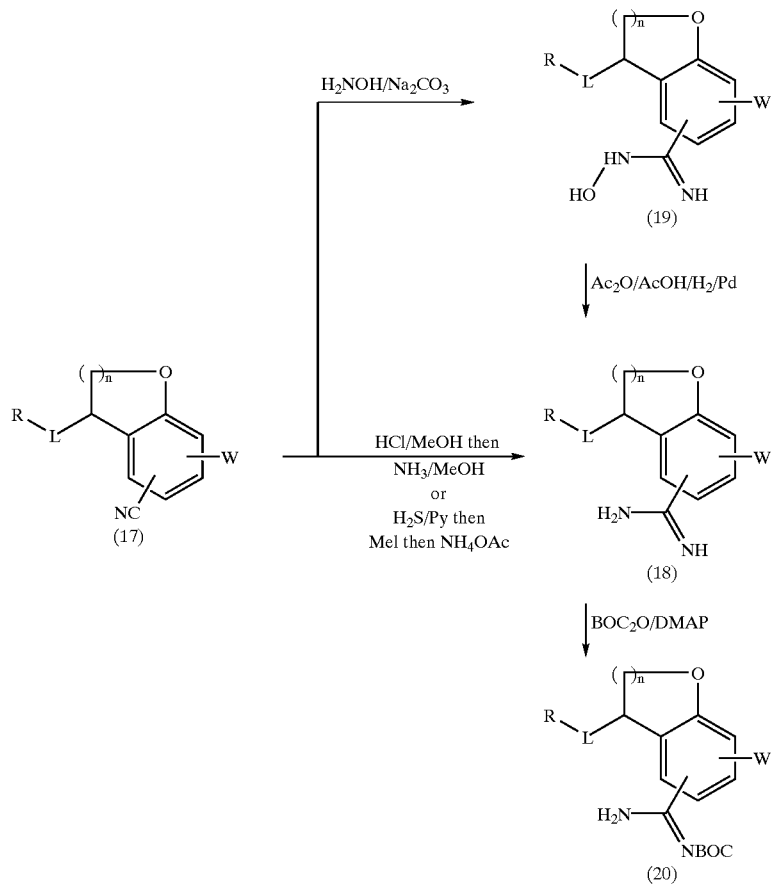

An amidine can also be prepared by addition of hydroxylamine to the nitrile to form the corresponding N-hydroxyamidine (19) followed by acylation and hydrogenolysis of the N—O bond using hydrogen/acetic acid (AcOH)/acetic anhydride (AC$_2$O) in the presence of a catalyst such as palladium on carbon.

For certain transformations of the side chain, it may be necessary or preferable to protect the amidine nitrogen as an inert derivative (Protective Groups in Organic Synthesis, T. W. Greene and P. G. M. Wuts; John Wiley Publications 1991). A particularly suitable derivative for this purpose is the t-butyloxy-carbamate (20). This can be prepared by reaction of the appropriate amidine with di-t-butyldicarbonate in THF or dichloromethane in the presence of a base such as DMAP/triethylamine or disopropylethylamine at a temperature at or above room temperature. Cleavage of these BOC derivatives can be accomplished by treatment with trifluoro acetic acid (TFA) in dichloromethane or with HCl in ethyl acetate.

It will be apparent to those skilled in the art that certain compounds of formula I can exhibit isomerism, for example geometrical isomerism, e.g., E or Z isomerism, and optical isomerism, e.g., R or S configurations. Geometrical isomers include the cis and trans forms of compounds of the invention having alkenyl moieties. Individual geometrical isomers and stereoisomers within formula I, and their mixtures, are within the scope of the invention.

Such isomers can be separated from their mixtures by the application or adaptation of known methods, for example, chromatographic techniques and recrystallization techniques, or they can be separately prepared from the appropriate isomers of their intermediates, for example, by the application or adaptation of methods described herein.

The compounds of the present invention are useful in the form of the free base or acid or in the form of a pharmaceutically acceptable salt thereof. All forms are within the scope of the invention.

Where a compound of the present invention is substituted with a basic moiety, acid addition salts are formed, and are simply a more convenient form for use; and in practice, use of the salt form inherently amounts to use of the free base form. The acids that can be used to prepare the acid addition salts are preferably those which produce, when combined with the free base, pharmaceutically acceptable salts, that is, salts whose anions are non-toxic to the patient in pharmaceutical doses of the salts, so that the beneficial inhibitory effects on Factor Xa inherent in the free base are not vitiated by side effects ascribable to the anions. Although pharmaceutically acceptable salts of said basic compounds are preferred, all acid addition salts are useful as sources of the free base form, even if the particular salt, per se, is desired only as an intermediate product as, for example, when the salt is formed only for purposes of purification and identification, or when it is used as intermediate in preparing a pharmaceutically acceptable salt by ion exchange procedures. Pharmaceutically acceptable salts within the scope of the invention are those derived from the following acids: mineral acids, such as hydrochloric acid, sulfuric acid, phosphoric acid and sulfamic acid; and organic acids, such as acetic acid, citric acid, lactic acid, tartaric acid, malonic acid, methanesufonic acid, ethanesulfonic acid, benzenesulfonic acid, p-toluenesulfonic acid, cyclohexylsulfamic acid, quinic acid, and the like. The corresponding acid addition salts comprise the following: hydrohalides, e.g. hydrochlorides and hydrobromides, sulfates, phosphates, nitrates, sulfamates, acetates, citrates, lactates, tartarates, malonates, oxalates, salicylates, propionates, succinates, fumarates, maleates, methylene-bis-β-hydroxy-naphthoates, gentisates, mesylates, isethionates, di-p-toluoyltartrates, methanesulfonates, ethanesulfonates, benzenesulfonates, p-toluenesulfonates, cyclohexylsulfamates and quinates.

According to a further feature of the invention, acid addition salts of the compounds of this invention are prepared by reaction of the free base with the appropriate acid, by the application or adaptation of known methods. For example, the acid addition salts of the compounds of this invention are prepared either by dissolving the free base in aqueous or aqueous-alcohol solution or other suitable solvents containing the appropriate acid, and isolating the salt by evaporating the solution; or by reacting the free base and acid in an organic solvent, in which case the salt separates directly or can be precipitated by concentration of the solution.

The parent compounds of this invention can be regenerated from the acid addition salts by the application or adaptation of known methods. For example, parent compounds of the invention can be regenerated from their acid addition salts by treatment with an alkali, e.g., aqueous sodium bicarbonate solution or aqueous ammonia solution.

Where the compound of the invention is substituted with an acidic moiety, base addition salts thereof may be formed, and are simply a more convenient form for use; in practice, use of the salt form inherently amounts to use of the free acid form. The bases which can be used to prepare the base addition salts are preferably those which produce, when combined with the free acid, pharmaceutically acceptable salts, that is, salts whose cations are non-toxic to the animal organism in pharmaceutical doses of the salts, so that the beneficial inhibitory effects on Factor Xa inherent in the free base are not vitiated by side effects ascribable to the cations. Pharmaceutically acceptable salts, including, for example, alkali and alkaline earth metal salts, within the scope of the invention, are those derived from the following bases: sodium hydride, sodium hydroxide, potassium hydroxide, calcium hydroxide, aluminum hydroxide, lithium hydroxide, magnesium hydroxide, zinc hydroxide, ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, and the like.

Metal salts of compounds of the present invention may be obtained by contacting a hydride, hydroxide, carbonate or similar reactive compound of the chosen metal in an aqueous or organic solvent with the free acid form of the compound. The aqueous solvent employed may be water or it may be a mixture of water with an organic solvent, preferably an alcohol such as methanol or ethanol, a ketone such as acetone, an aliphatic ether such as tetrahydrofuran, or an ester such as ethyl acetate. Such reactions are normally conducted at ambient temperature but they may, if desired, be conducted with heating.

Amine salts of compounds of the present invention may be obtained by contacting an amine in an aqueous or organic solvent with the free acid form of the compound. Suitable aqueous solvents include water and mixtures of water with alcohols such as methanol or ethanol, ethers such as tetrahydrofuran, nitrites such as acetonitrile, or ketones such as acetone. Amino acid salts may be similarly prepared.

The parent compounds of this invention can be regenerated from the base addition salts by the application or adaptation of known methods. For example, parent compounds of the invention can be regenerated from their base addition salts by treatment with an acid, e.g. hydrochloric acid.

Pharmaceutically acceptable salts also include quaternary lower alkyl ammonium salts. The quaternary salts are prepared by the exhaustive alkylation of basic nitrogen atoms in compounds, including nonaromatic and aromatic basic nitrogen atoms, according to the invention, i.e., by alkylating the non-bonded pair of electrons of the nitrogen moieties with an alkylating agent such as methylhalide, particularly methyl iodide, or dimethyl sulfate. Quaternarization results in the nitrogen moiety becoming positively charged and having a negative counter ion associated therewith.

As will be self-evident to those skilled in the art, some of the compounds of this invention do not form stable salts. However, acid addition salts are most likely to be formed by compounds of this invention having a nitrogen-containing heteroaryl group and/or wherein the compounds contain an amino group as a substituent. Preferable acid addition salts of the compounds of the invention are those wherein there is not an acid labile group.

As well as being useful in themselves as active compounds, salts of compounds of the invention are useful for the purposes of purification of the compounds, for example by exploitation of the solubility differences between the salts and the parent compounds, side products and/or starting materials by techniques well known to those skilled in the art.

The starting materials and intermediates are prepared by the application or adaptation of known methods, for example, methods as described in the Reference Examples or their obvious chemical equivalents, or by methods according to this invention.

The present invention is further exemplified, but not limited, by the following illustrative examples, which illustrate the preparation of compounds according to the invention.

Experimental Section

Unless otherwise stated, all starting materials can be obtained from commercial suppliers and are used without further purification. Reactions are routinely carried out under an inert atmosphere of nitrogen or argon using anhydrous solvents obtained from Aldrich Chemical Company. Flash column chromatography is performed on Merck silica gel (230–400 mesh), eluting with the specified solvent mixture. Reverse phase HPLC is performed using Dynamax C-18 (60A) columns, eluting with a water/acetonitrile gradient (containing a fixed 0.1% v/v trifluoroacetic acid additive) with UV detection ($\lambda$=220, 254, 294 nM). $^1$H NMR spectra are recorded at a frequency of 300 MHz in the specified deuterated solvent. Chemical shifts are in ppm relative to the resonance frequency of tetramethylsilane $\delta$=0.00. The following conventions are used throughout to describe NMR spectra: s=singlet, d=doublet, t=triplet, q=quartet, m=multiplet, b=broad. Coupling constants are designated with the symbol J and are quoted in Hz.

EXAMPLE 1a 5-(Pyridin-2-yl)-thiophene-2-carboxylic acid (2-[5-carbamimidoyl-2,3-dihydrobenzofuran-3-yl]ethyl) amide To a solution of 5-pyridin-2-ylthiophene-2-carboxylic acid (2-[5-{N-tert-butoxycarbonyl}carbamimidoyl-2,3-dihydrobenzofuran-3-yl]ethyl)amide (Reference Example 1a, 69 mg, 0.14 mmol) in $CH_2Cl_2$ (8 mL) is added $H_2O$ (0.1 mL) and trifluoroacetic acid (2 mL). After stirring under nitrogen for 3 hours, the reaction mixture is concentrated, then placed under high vacuum overnight to give a quantitative yield of the title compound as a tan solid (m.p. 54–56° C.). $^1$H NMR ($CD_3OD$): $\delta$1.95 (1H, m), 2.11 (1H, m), 3.51 (2H, m), 3.65 (1H, m), 4.48 (1H, m), 4.83 (1H, m), 6.93 (1H, d, J=8.5 Hz), 7.38 (1H, dd, $J_1$=8.8 Hz, $J_2$=4.7 Hz), 7.65 (1H, d, J=8.5 Hz), 7.69 (1H, d, J=4.0 Hz), 7.72 (1H, d, J=4.0 Hz), 7.92 (2H, m), 7.98 (1H, s), 8.55 (1H, d, J=4.7 Hz). MS (ion spray) m/z: 393 $(M+H)^+$. Exact mass (FAB) calcd for $C_{21}H_{21}N_4O_2S$ (M+H) 393.1385, found 393.1352.

The following compounds are prepared using essentially the same procedure described in example 1a except using the cited N-tert-butoxycarbonyl-protected amidine as substrate.

EXAMPLE 1b 4-tert-Butyl-N-(2-[5-carbamimidoyl-2,3-dihydrobenzofuran-3-yl]ethyl)benzamide Using the product from Reference Example 1b, and following the procedure of Example 1a, the title compound is produced. White solid (m.p. 167–169° C.). $^1$H NMR ($CD_3OD$): $\delta$1.34 (9H, s), 1.94 (1H, m), 2.12 (1H, m), 3.52 (2H, m), 3.64 (1H, m), 4.48 (1H, m), 4.83 (1H, m), 6.94 (1H, d, J=8.6 Hz), 7.51 (2H, d, J=8.6 Hz), 7.64 (1H, d, J=8.6 Hz), 7.76 (2H, d, J=8.6 Hz), 7.77 (1H, s), 8.57 (1H, br, m). MS (FAB) m/z: 366 $(M+H)^+$. Anal. calcd for $C_{22}H_{27}N_3O_2 \cdot C_2HF_3O_2 \cdot 0.25H_2O$: C, 59.6%; H, 5.9%; 8.7%. Found: C, 59.7%; H, 6.0%; N, 8.1%.

EXAMPLE 1c 4-(2-Amino-1,1-dimethylethyl)-N-(2-[5-carbamimidoyl-2,3-dihydrobenzofuran-3-yl]ethyl) benzamide Using the product from Reference Example 1 c, and following the procedure of Example 1a, the title compound is produced. White solid (m.p. 209–210° C.). $^1$H NMR ($CD_3OD$): $\delta$1.46 (6H, s), 1.95 (1H, m), 2.12 (1H, m), 3.23 (2H, s), 3.53 (2H, m), 3.64 (1H, m), 4.48 (1H, m), 4.86 (1H, m), 6.94 (1H, d, J=8.5 Hz), 7.57 (2H, d, J=8.5 Hz), 7.65 (1H, d, J=8.5 Hz), 7.78 (1H, s), 7.87 (2H, d, J=8.5 Hz), 8.65 (1H, br, m). MS (ion spray) m/z: 381 $(M+H)^+$. Anal. calcd for $C_{22}H_{28}N_4O_2 \cdot 2C_2HF_3O_2 \cdot 2H_2O$: C, 48.4%; H, 5.3%; N, 8.7%. Found: C, 48.2%; H, 5.0%; N, 8.7%.

EXAMPLE 1d

N-[2-(5-carbamimidoyl-2,3-dihydro-benzofuran-3-yl)-ethyl]-4-(3-amino-propyl)-benzamide Using the product from Reference Example 1d, and following the procedure of Example 1a, the title compound is produced. $^1$H NMR (DMSO) $\delta$1.84 (m, 3H), 2.04 (m, 1H), 2.70 (t, J=8 Hz, 2H), 2.80 (m, 2H), 3.40 (m, 2H), 3.58 (m, 1H), 4.43 (m, 1H), 4.81 (t, J=9 Hz, 1H), 7.00 (d, J=8 Hz, 1H), 7.31 (d, J=8 Hz, 2H), 7.68 (dd, J=9, 2 Hz, 1H), 7.81 (m, 6H), 8.59 (bt, 1H), 9.01 (s, 2H), 9.10 (s, 2H). MS (ion spray) m/z 367 $(M+H)^+$. Combustion Analysis: $C_{21}H_{26}N_4O_2$; $(C_2HF_3O_2)_2;(H_2O)_{2.5}$ requires C 47.0, H 5.2, N 8.8. Found C 47.2, H 4.6, N 8.4.

EXAMPLE 1e

N-[2-(5-carbamimidoyl-2,3-dihydro-benzofuran-3-yl)-ethyl]-2-(N-phenyl-amino)-Benzamide Using the product from Reference Example 1e, and following the procedure of Example 1a, the title compound is produced. MS m/z=401 M+H

EXAMPLE 1f

N-[2-(5-carbamimidoyl-2,3-dihydro-benzofuran-3-yl)-ethyl]-2-(phenoxy)-Benzamide

Using the product from Reference Example 1f, and following the procedure of Example 1a, the title compound is produced. MS m/z=402 M+H

EXAMPLE 1g

N-[2-(5-carbamimidoyl-2,3-dihydro-benzofuran-3-yl)-ethyl]-4-(N,N-diethylamino)-Benzamide Using the product from Reference Example 1g, and following the procedure of Example 1a, the title compound is produced. MS m/z=381 M+H

EXAMPLE 1h

N-[2-(5-carbamimidoyl-2,3-dihydro-benzofuran-3-yl)-ethyl]-4-(phenoxy)-Benzamide

Using the product from Reference Example 1h, and following the procedure of Example 1a, the title compound is produced. MS m/z=402 M+H

EXAMPLE 1i

N-[2-(5-carbamimidoyl-2,3-dihydro-benzofuran-3-yl)-ethyl]-2-methyl-3-phenyl-prop-2-enoic acid amide Using the product from Reference Example 1i, and following the procedure of Example 1a, the title compound is produced. MS m/z=350 M+H

EXAMPLE 1j

N-[2-(5-carbamimidoyl-2,3-dihydro-benzofuran-3-yl)-ethyl]-10-cyano-decanoic acid amide Using the product from Reference Example 1j, and following the procedure of Example 1a, the title compound is produced. MS m/z=399 M+H.

EXAMPLE 1k

N-[2-(5-carbamimidoyl-2,3-dihydro-benzofuran-3-yl)-ethyl]-4-oxo-(4-methoxy-phenyl)-butyramide Using the product from Reference Example 1k, and following the procedure of Example 1a, the title compound is produced. MS m/z=396 M+H.

EXAMPLE 1l

N-[2-(5-carbamimidoyl-2,3-dihydro-benzofuran-3-yl)-ethyl]-(1-methyl-pyrrole-2-carboxamide)

Using the product from Reference Example 1l, and following the procedure of Example 1a, the title compound is produced. MS m/z=313 M+H.

EXAMPLE 1m

N-[2-(5-carbamimidoyl-2,3-dihydro-benzofuran-3-yl)-ethyl]-(2,2-diphenyl-propionamide)

Using the product from Reference Example 1m, and following the procedure of Example 1a, the title compound is produced. MS m/z=414 M+H.

EXAMPLE 1n

N-[2-(5-carbamimidoyl-2,3-dihydro-benzofuran-3-yl)-ethyl]-(2-(4-chloro-phenoxy)-2-methyl-propionamide Using the product from Reference Example 1n, and following the procedure of Example 1a, the title compound is produced. MS m/z=402 M+H.

EXAMPLE 1o

N-[2-(5-carbamimidoyl-2,3-dihydro-benzofuran-3-yl)-ethyl]-(2-[4-phenyl]-phenyl-acetamide)

Using the product from Reference Example 1o, and following the procedure of Example 1a, the title compound is produced. MS m/z=400 M+H.

EXAMPLE 1p

N-[2-(5-carbamimidoyl-2,3-dihydro-benzofuran-3-yl)-ethyl]-3-[3,4-dimethoxy-phenyl]-prop-2-enoic acid amide Using the product from Reference Example 1p, and following the procedure of Example 1a, the title compound is produced. MS m/z=396 M+H.

EXAMPLE 1q

N-[2-(5-carbamimidoyl-2,3-dihydro-benzofuran-3-yl)-ethyl]-(5-oxo-5-phenyl-pentanoic acid amide)

Using the product from Reference Example 1q, and following the procedure of Example 1a, the title compound is produced. MS m/z=380 M+H.

EXAMPLE 1r

N-[2-(5-carbamimidoyl-2,3-dihydro-benzofuran-3-yl)-ethyl]-xanthine-9-carboxamide Using the product from Reference Example 1r, and following the procedure of Example 1a, the title compound is produced. MS m/z=414 M+H.

EXAMPLE 1s

5-[1,2] dithiolan-3-yl-pentanoic Acid-N-[2-(5-carbamimidoyl-2,3-dihydro-benzofuran-3-yl)-ethyl]-amide Using the product from Reference Example 1s, and following the procedure of Example 1a, the title compound is produced. MS m/z=394 M+H.

EXAMPLE 1t

N-[2-(5-carbamimidoyl-2,3-dihydro-benzofuran-3-yl)-ethyl]-5-methoxy-indole-2 carboxamide Using the product from Reference Example 1t, and following the procedure of Example 1a, the title compound is produced. MS m/z=379 M+H.

EXAMPLE 1u

N-[2-(5-carbamimidoyl-2,3-dihydro-benzofuran-3-yl)-ethyl]-3,4-methylenedioxy cinnamic acid amide Using the product from Reference Example 1u, and following the procedure of Example 1a, the title compound is produced. MS m/z=380 M+H.

EXAMPLE 1v

N-[2-(5-carbamimidoyl-2,3-dihydro-benzofuran-3-yl)-ethyl]-3-quinoline carboxamide Using the product from reference example 1v, and following the procedure of Example 1a, the title compound is produced. MS m/z=361 M+H.

EXAMPLE 1w 2,3-Dihydro-benzo[1,4]-dioxine-2-carboxylic Acid-N-[2-(5-carbamimidoyl-2,3-dihydro-benzofuran-3-yl)-ethyl]-amide Using the product from Reference Example 1w, and following the procedure of Example 1a, the title compound is produced. MS m/z=368 M+H.

EXAMPLE 1x

N-[2-(5-carbamimidoyl-2,3-dihydro-benzofuran-3-yl)-ethyl]-(2-[4-cyano-phenoxy]-2-methyl-propionamide Using the product from Reference Example 1x, and following the procedure of Example 1a, the title compound is produced. MS m/z=393 M+H.

EXAMPLE 1y

N-[2-(5-carbamimidoyl-2,3-dihydro-benzofuran-3-yl)-ethyl]-2-(4-oxo-3,4-dihydro-pthalazin-1-yl)-acetamide Using the product from Reference Example 1y, and following the procedure of Example 1a, the title compound is produced. MS m/z=392 M+H.

EXAMPLE 1z

3-Methyl-sulfanyl-4-oxo-4,5,6,7-tetrahydro-benzo[c]-thiophene-1-carboxylic acid N-[2-(5-carbamimidoyl-2,3-dihydro-benzofuran-3-yl)-ethyl]-amide Using the product from Reference Example 1z, and following the procedure of Example 1a, the title compound is produced. MS m/z=430 M+H.

EXAMPLE 1aa 4,5-Dimethyl-1-phenyl-pyrrole-3-carboxylic Acid N-[2-(5-carbamimidoyl-2,3-dihydro-benzofuran-3-yl)-ethyl]-amide Using the product from Reference Example 1aa, and following the procedure of Example 1a, the title compound is produced. MS m/z=403 M+H.

EXAMPLE 1ab

4-Oxo-4H-9-thia-1,4a-diaza-fluorene-3-carboxylic Acid N-[2-(5-carbamimidoyl-2,3-dihydro-benzofuran-3-yl)-ethyl]-amide Using the product from reference example 1ab, and following the procedure of Example 1a, the title compound is produced. MS m/z=434 M+H.

EXAMPLE 1ac 6-(1-pyrazole)-nicotinic acid N-[2-(5-carbamimidoyl-2,3-dihydro-benzofuran-3-yl)-ethyl]-amide Using the product from Reference Example 1ac, and following the procedure of Example 1a, the title compound is produced. MS m/z=377 M+H.

EXAMPLE 1ad

3-Nitro-4-(1-pyrazolyl)benzoic Acid N-[2-(5-carbamimidoyl-2,3-dihydro-benzofuran-3-yl)-ethyl]-amide Using the product from Reference Example 1ad, and following the procedure of Example 1a, the title compound is produced. MS m/z=421 M+H.

EXAMPLE 1ae

N-Tosyl-3-pyrrole-carboxylic Acid N-[2-(5-carbamimidoyl-2,3-dihydro-benzofuran-3-yl)-ethyl]-amide Using the product from Reference Example 1ae, and following the procedure of Example 1a, the title compound is produced. MS m/z=453 M+H.

EXAMPLE 1af 4-oxo-4,5,6,7-tetrahydro-benzofuran-3-carboxylic acid [2-(5-carbamimidoyl-2,3-dihydro-benzofuran-3-yl)-ethyl]-amide Using the product from reference example 1af, and following the procedure of Example 1a, the title compound is produced. MS m/z=368 M+H.

EXAMPLE 1ag 4-tert-butyl-2,6-dimethyl-cyclohexanecarboxylic Acid [2-(5-carbamimidoyl-2,3-dihydro-benzofuran-3-yl)-ethyl]-amide Using the product from Reference Example 1ag, and following the procedure of Example 1a, the title compound is produced. MS m/z=394 M+H.

EXAMPLE 1ah 5-methyl-1-(3-trifluoromethyl-phenyl)-4,5-dihydro-1H-[1,2,3]triazole-4-carboxylic Acid [2-(5-carbamimidoyl-2,3-dihydro-benzofuran-3-yl)-ethyl]-amide Using the product from Reference Example 1ah, and following the procedure of Example 1a, the title compound is produced. MS m/z=459 M+H.

EXAMPLE 1ai 2-benzylsulfanyl-N-[2-(5-carbamimidoyl-2,3-dihydro-benzofuran-3-yl)-ethyl]-propionamide Using the product from reference example 1ai, and following the procedure of Example 1a, the title compound is produced. MS m/z=384 M+H.

EXAMPLE 1aj 5-pyridin-2-yl-thiophene-2-carboxylic acid [2-(5-carbamimidoyl-2,3-dihydro-benzofuran-3-yl)-ethyl]-amide Using the product from Reference Example 1aj, and following the procedure of Example 1a, the title compound is produced. MS m/z=393 M+H.

EXAMPLE 1ak 4-butyl-cyclohexanecarboxylic acid [2-(5-carbamimidoyl-2,3-dihydro-benzofuran-3-yl)-ethyl]-amide Using the product from Reference Example 1ak, and following the procedure of Example 1a, the title compound is produced. MS m/z=372 M+H.

EXAMPLE 1al 5-methyl-1-phenyl-1H-pyrazole-4-carboxylic acid [2-(5-carbamimidoyl-2,3-dihydro-benzofuran-3-yl)-ethyl]-amide Using the product from Reference Example 1al, and following the procedure of Example 1a, the title compound is produced. MS m/z=390 M+H.

EXAMPLE 1am

N-[2-(5-carbamimidoyl-2,3-dihydro-benzofuran-3-yl)-ethyl]-6-pyrrol-1-yl-nicotinamide Using the product from Reference Example 1am, and following the procedure of Example 1a, the title compound is produced. MS m/z=376 M+H.

EXAMPLE 1an 4-chloro-1,3-dimethyl-1H-pyrazolo[3,4-b]pyridine-5-carboxylic Acid [2-(5-carbamimidoyl-2,3-dihydro-benzofuran-3-yl)-ethyl]-amide Using the product from Reference Example 1an, and following the procedure of Example 1a, the title compound is produced. MS m/z=413 M+H.

EXAMPLE 1ao 4-methyl-2-(4-trifluoromethyl-phenyl)-thiazole-5-carboxylic acid [2-(5-carbamimidoyl-2,3-dihydro-benzofuran-3-yl)-ethyl]-amide Using the product from Reference Example 1ao, and following the procedure of Example 1a, the title compound is produced. MS m/z=475 M+H.

EXAMPLE 1ap (S)-2-(6-Methoxynaphthyl)-N-(2-[5-carbamimidoyl-2,3-dihydrobenzofuran-3-yl]ethyl)propionamide Using the product from Reference Example 1ap, and following the procedure of Example 1a, the title compound is produced. MS m/z 418 M+H.

EXAMPLE 1aq

N-(2-[5-Carbamimidoyl-2,3-dihydrobenzofuran-3-yl]ethyl)-3-chlorobenzothiophene-2-carboxamide Using the product from Reference Example 1aq, and following the procedure of Example 1a, the title compound is produced. MS m/z=400 M+H.

EXAMPLE 1ar

4-Benzyloxy-N-(2-[5-carbamimidoyl-2,3-dihydrobenzofuran-3-yl]ethyl)benzamide

Using the product from Reference Example 1ar, and following the procedure of Example 1a, the title compound is produced. MS m/z=416 M+H.

EXAMPLE 1as 4-(4-n-Propylphenyl)-N-(2-[5-carbamimidoyl-2,3-dihydrobenzofuran-3-yl]ethyl)benzamide Using the product from Reference Example 1as, and following the procedure of Example 1a, the title compound is produced. MS m/z=428 M+H.

EXAMPLE 1at

2-Methylthio-N-(2-[5-carbamimidoyl-2,3-dihydrobenzofuran-3-yl]ethyl)benzamide

Using the product from Reference Example 1at, and following the procedure of Example 1a, the title compound is produced. MS m/z=356 M+H.

EXAMPLE 1au 3-(4-Pyridyl)-N-(2-[5-carbamimidoyl-2,3-dihydrobenzofuran-3-yl]ethyl)acrylamide Using the product from Reference Example 1au, and following the procedure of Example 1a, the title compound is produced. MS m/z=337 M+H.

EXAMPLE 1av

N-(2-[5-Carbamimidoyl-2,3-dihydrobenzofuran-3-yl]ethyl)-4-tert-butylcyclohexanecarboxamide Using the product from reference example 1av, and following the procedure of Example 1a, the title compound is produced. MS m/z=372 M+H.

EXAMPLE 1aw

N-(2-[5-Carbamimidoyl-2,3-dihydrobenzofuran-3-yl]ethyl)-5-methylindole-2-carboxamide Using the product from Reference Example 1aw, and following the procedure of Example 1a, the title compound is produced. MS m/z=363 M+H.

EXAMPLE 1ax

N-(2-[5-Carbamimidoyl-2,3-dihydrobenzofuran-3-yl]ethyl)quinoline-6-carboxamide

Using the product from Reference Example 1ax, and following the procedure of Example 1a, the title compound is produced. MS m/z=361 M+H.

EXAMPLE 1ay

N-(2-[5-Carbamimidoyl-2,3-dihydrobenzofuran-3-yl]ethyl)benzothiophene-2-carboxamide Using the product from Reference Example 1ay, and following the procedure of Example 1a, the title compound is produced. MS m/z=366 M+H.

EXAMPLE 1az

2-Pyrrolyl-N-(2-[5-carbamimidoyl-2,3-dihydrobenzofuran-3-yl]ethyl)benzamide

Using the product from Reference Example 1az, and following the procedure of Example 1a, the title compound is produced. MS m/z=375 M+H.

EXAMPLE 1aaa

4-Methyl-2-phenyl-N-(2-[5-carbamimidoyl-2,3-dihydrobenzofuran-3-yl]ethyl)-1,2,3-triazole-5-carboxamide MS m/z=391 M+H.

EXAMPLE 1aab

N-(2-[5-Carbamimidoyl-2,3-dihydrobenzofuran-3-yl]ethyl)-phthalide-3-acetamide

Using the product from reference example 1aaa. MS m/z=380 M+H.

EXAMPLE 1aac

N-[2-(5-Carbamimidoyl-2,3-dihydro-Benzofuran-3-yl)-ethyl]-4-(phenyl)-Benzamide

To a suspension of N-[2-(5-cyano-2,3-dihydro-Benzofuran-3-yl)-ethyl]-4-(phenyl)-benzamide (reference example 1aab, 476 mg, 1.29 mmol) in methanol (1 mL) is added a saturated solution of HCl in methanol (12 mL). The resulting mixture is stirred for 3 h then concentrated. The residue is dissolved in a saturated solution of ammonia in methanol (12 mL) and this solution stirred for 16 h. The solution is then concentrated and the residue purified by flash chromatography (eluting with 10% methanol in $CH_2Cl_2$) to give the title compound as a solid (431 mg). $^1$H NMR (DMSO) d 1.88 (m, 1H), 2.10 (m, 1H), 3.44 (m, 2H), 3.64 (m, 1H), 4.45 (t, J=9 Hz, 1H), 4.95 (t, J=9 Hz, 1H), 7.01 (d, J=8 Hz, 1H), 7.4–7.55 (m, 3H), 7.7–7.84 (m, 5H), 7.90 (s, 1H), 8.0 (d, J=8 Hz, 2H), 8.83 (bt, 1H), 9.05 (s, 2H), 9.25 (bs, 2H), MS (FAB) m/z 386 (M+H)$^+$. Combustion Analysis: $C_{24}H_{23}N_3O;(HCl);(H_2O)_{1.5}$ requires C 64.2, H 5.8, N 9.4. Found C 64.3, H 5.6, N 9.4.

The following compounds are prepared using essentially the same procedure described in example 1aab except using the cited nitrile as substrate.

EXAMPLE 1aad

N-[2-(5-Carbamimidoyl-2,3-dihydro-Benzofuran-3-yl)-ethyl]-4-(pyridin-3-yl)-Benzamide Using the product from reference example 1aac. $^1$H NMR ($CD_3OD$) d 2.00 (m, 1H), 2.18 (m, 1H), 3.55 (m, 2H), 3.70 (m, 1H), 4.53 (dd, J=8, 7 Hz, 1H), 4.89 (t, J=8 Hz, 1H), 6.97 (d, J=8 Hz, 1H), 7.60 (dd, J=7, 4 Hz, 1H), 7.70 (dd, J=8, 1 Hz, 1H), 7.84 (m, 3H), 8.02 (d, J=8 Hz, 2H), 8.20 (bd, J=7 Hz, 1H), 8.60 (bd, J=4 Hz, 1H), 8.89 (bs, 1H). MS (FAB) m/z 387 (M+H)$^+$.

EXAMPLE 1aae 4-(1-Aminomethyl-cyclopentyl)-N-[2-(5-carbamimidoyl-2,3-dihydro-Benzofuran-3-yl)-ethyl]-benzamide Using the product from reference example 1aad. $^1$H NMR ($CD_3OD$) d 1.66–2.20 (m, 10H), 3.53 (t, J=7 Hz, 2H), 3.67 (m, 1H), 4.48 (dd, J=8, 7 Hz, 1H), 4.83 (t, J=8 Hz, 1H), 6.92 (d, J=8 Hz, 1H), 7.53 (d, J=8 Hz, 2H), 7.68 (dd, J=8, 1 Hz, 1H), 7.81 (d, J=1 Hz, 1H), 7.90 (d, J=8 Hz, 2H). MS (ion spray) m/z 407 (M+H)$^+$.

EXAMPLE 1aaf

N-[2-(5-carbamimidoyl-2,3-dihydro-Benzofuran-3-yl)-ethyl]-4-(pyridine-N-oxid-3-yl)-benzamide Using the product from reference example 1aae.

EXAMPLE 1aag

N-[2-(5-carbamimidoyl-2,3-dihydro-Benzofuran-3-yl)-ethyl]-4-(pyridin-4-yl)-benzamide Using the product from reference example 1aaf.

EXAMPLE 1aah

N-[2-(5-carbamimidoyl-2,3-dihydro-Benzofuran-3-yl)-ethyl]-4-(6-oxo-1,6-dihydro-pyridin-3-yl)-benzamide Using the product from reference example 1 aag.

EXAMPLE 1aai

N-[2-(5-carbamimidoyl-2,3-dihydro-Benzofuran-3-yl)-ethyl]-4-[(3-(aminomethyl)-phenyl]-benzamide Using the product from reference example 1aah.

EXAMPLE 1aaj

N-[2-(5-carbamimidoyl-2,3-dihydro-Benzofuran-3-yl)-ethyl]-4-(pyridazin-3-yl)-benzamide Using the product from reference example 1aai.

EXAMPLE 1aak

N-[2-(5-carbamimidoyl-2,3-dihydro-Benzofuran-3-yl)-ethyl]-4-(pyridazin-4-yl)-benzamide Using the product from reference example 1aaj.

EXAMPLE 1aal

N-[2-(5-carbamimidoyl-2,3-dihydro-Benzofuran-3-yl)-ethyl]-4-(pyrimidin-5-yl)-benzamide Using the product from reference example 1aak.

EXAMPLE 1aam

N-[Biphenyl-4-yl-methyl]-2-(5-carbamimidoyl-2,3-dihydro-benzofuranyl) acetamide

Using the product from reference example 34a. $^1$H NMR (DMSO): δ2.58 (dd, J=16, 8 Hz, 1H), 2.71 (dd, J=16, 6 Hz, 1H), 3.92 (m, 1H), 4.30 (dd, J=15, 5 Hz, 1H), 4.38 (dd, J=15, 5 Hz, 1H), 4.47 (dd, J=8, 7 Hz, 1H), 4.84 (t, J=8 Hz, 1H), 7.0 (d, J=8 Hz, 1H), 7.30 (d, J=8 Hz, 2H), 7.37 (m, 1H), 7.45 (m, 2H), 7.62 (m, 6H), 7.83 (bs, 1H), 8.65 (t, J=7 Hz, 1H), 8.93 (s, 2H), 9.2 (s, 2H). MS (FAB) m/z 386 (M+H).

EXAMPLE 1aan

N-[Biphenyl-4-yl]-2-(5-carbamimidoyl-2,3-dihydro-benzofuranyl) acetamide

Using the product from reference example 34b. $^1$H NMR ($CD_3OD$): δ2.79 (dd, J=16, 8 Hz, 1H), 2.93 (dd, J=16, 7 Hz, 1H), 4.07 (m, 1H), 4.51 (dd, J=8, 7 Hz, 1H), 4.90 (t, J=8 Hz, 1H), 6.97 (d, J=8 Hz, 1H), 7.31 (m, 1H), 7.42 (m, 2H), 7.6 (m, 8H), 7.75 (bs, 1H). MS (FAB) m/z 372 (M+H).

EXAMPLE 1aao 3-(3-Biphenyl-4-ylmethyl-ureido-methyl)-2,3-dihydrobenzofuran-5-carboxamidine Using the product from reference example 35. $^1$H NMR ($CD_3OD$): δ3.48 (t, J=6 Hz, 2H), 3.75 (m, 1H), 4.30 (d, J=15 Hz, 1H), 4.37 (d, J=15 Hz, 1H), 4.55 (dd, J=9, 5 Hz, 1H), 4.73 (t, J=9 Hz, 1H), 6.43 (bt, 1H), 6.57 (bt, 1H), 6.93 (d, J=8 Hz, 1H), 7.3 (m, 3H), 7.41 (m, 2H), 7.55 (m, 4H), 7.65 (dd, J=8, 1 Hz, 1H), 7.73 (d, J=1 Hz, 1H). MS (FAB) m/z 401.

EXAMPLE 1aap

3-[2-(4-Benzyl-piperazin-1-yl-2-oxo-ethyl]-2,3-dihydro-benzofuran-5-carboxamidine Using the product from reference example 34c. $^1$H NMR ($CD_3OD$): δ2.80 (dd, J=15, 7 Hz, 1H), 3.05 (m, 1H), 3.35 (bm, 8H), 3.98 (m, 1H), 4.39 (m, 3H), 4.40 (t, J=9 Hz, 1H), 6.94 (d, J=8 Hz, 1H), 7.52 (m, 5H), 7.65 (dd, J=8, 1 Hz, 1H), 7.75 (bs, 1H). MS (FAB) m/z 379 (M+H).

EXAMPLE 1aaq

3-[2-(4-Benzyl-piperidin-1-yl-2-oxo-ethyl]-2,3-dihydro-benzofuran-5-carboxamidine Using the product from reference example 34d. $^1$H NMR ($CD_3OD$): δ1.4 (m, 2H), 1.59 (m, 2H), 1.75 (m, 1H), 2.62

(m, 2H), 3.0 (m, 2H), 3.82 (m, 2H), 4.33 (m, 2H), 4.87 (t, J=9 Hz, 1H), 6.98 (d, J=8 Hz, 1H), 7.18 (m, 3H), 7.30 (m, 2H), 7.66 (bd, J=8 Hz, 1H), 7.82 (bs, 1H), 8.90 (bs, 2H), 9.2 (bs, 2H). MS (FAB) m/z 378 (M+H).

EXAMPLE 1aar

3-{2-[4-(1,1-Dimethylpropyl)benzenesulfonylamino] ethyl}-5-carbamimidoyl-2,3-dihydrobenzofuran Using the product from reference example 36. m.p. 52-56° C. $^1$H NMR (CD$_3$OD): δ0.665 (3H, t, J=7 Hz), 1.32 (6H, s), 1.71 (2H, q, J=7 Hz), 1.75 (1H, m), 1.96 (1H, m), 2.98 (2H, m), 3.64 (1H, m), 4.35 (1H, m), 4.74 (1H, t, J=9 Hz), 6.92 (1H, d, J=8 Hz), 7.56 (2H, d, J=8 Hz), 7.64 (1H, d, J=8 Hz), 7.69 (1H, s), 7.78 (2H, d, J=8 Hz). LC/MS (ion spray) m/z=416 (M+H)$^+$.

EXAMPLE 1aas

3-[2-(7-Chlorobenzo[1,2,5]oxadiazole-5-sulfonylamino)ethyl]-5-carbamididoyl-2,3-dihydrobenzofuran Using the product from reference example 37. m.p. 210-212° C. $^1$H NMR (CD$_3$OD): δ1.82 (1H, m), 2.02 (1H, m), 3.19 (2H, m), 3.69 (1H, m), 4.40 (1H, m), 4.78 (1H, t, J=9 Hz), 6.92 (1H, d, J=8 Hz), 7.64 (1H, d, J=8 Hz), 7.70 (1H, s), 7.76 (1H, d, J=7 Hz), 8.06 (1H, d, J=7 Hz). MS (ion spray) m/z=422 (M+H)$^+$. Anal. calcd for C$_{17}$H$_{16}$N$_5$O$_4$SC$_1$.C$_2$HO$_2$F$_3$: C, 42.59; H, 3.20; N, 13.07. Found: C, 42.62; H, 3.10; N, 12.44.

Reference Example 1a

5-Pyridin-2-ylthiophene-2-carboxylic Acid (2-[5-{N-tert-butoxycarbonyl}carbamimidoyl-2,3-dihydrobenzofuran-3-yl]ethyl)amide To a cooled (0° C.) solution of 5-(pyrid-2-yl)thiophene-2-carboxylic acid (107 mg, 0.521 mmol) and 4-methylmorpholine (0.11 ml, 1.04 mmol) in 10 ml CH$_2$Cl$_2$ (10 mL) is added dropwise a solution of isopropyl chloroformate in toluene (1.04 mL, 1M)). After stirring under nitrogen for 30 minutes, 2-(5-[N-tert-butoxycarbonyl] carbamimidoyl-2,3-dihydrobenzofuran-3-yl)ethylamine (0.191 g, 0.625 mmol) (Reference Example 28) in DMF (12.5 mL) is added, and the reaction allowed to warm to room temperature overnight. The reaction mixture is concentrated, and the resulting residue chromatographed (30:1, then 20:1 CH$_2$Cl$_2$: MeOH) to provide 0.069 g of the title compound as a yellow solid. $^1$H NMR (CDCl$_3$): δ1.54 (9H, s), 1.83 (1H, m), 1.95 (1H, m), 3.41 (1H, m), 3.49 (2H, m), 4.36 (1H, m), 4.71 (1H, m), 6.73 (1H, br, m), 6.76 (1H, d, J=8.4 Hz), 7.22 (1H, m), 7.55 (1H, d, J=3.8 Hz), 7.67–7.81 (4H, m), 8.02 (1H, s), 8.58 (1H, d, J=4.7 Hz). MS (FAB) m/z: 493 (M+H)$^+$.

Reference Example 1b

By employing essentially the same procedure as used in reference example 1a, except using 4-tert-buty-benzoic acid, there is prepared 4-tert-Butyl-N-(2-[5-{N-tert-butoxycarbonyl}carb-amimidoyl-2,3-dihydrobenzofuran-3-yl]ethyl)benzamide. $^1$H NMR (CDCl$_3$): δ1.33 (9H, s), 1.54 (9H, s), 1.86 (1H, m), 2.00 (1H, m), 3.45–3.53 (3H, m), 4.37 (1H, m), 4.72 (1H, m), 6.52 (1H, br, m), 6.76 (1H, d, J=8.6 Hz), 7.45 (2H, d, J=8.5 Hz), 7.67 (1H, d, J=8.6 Hz), 7.75 (2H, d, J=8.5 Hz), 7.83 (1H, s). MS (ion spray) m/z: 466 (M+H)$^+$.

Reference Example 1c 4-(2-tert-Butoxycarbonylamino-1,1-dimethylethyl)-N-(2-[5-{N-tert-butoxycarbonyl}carbamimidoyl-2,3-dihydrobenzofuran-3-yl]ethyl)benzamide To a suspension of 4-(2-tert-butoxycarbonylamino-1,1-dimethylethyl)benzoic acid (220 mg, 0.750 mmol) (reference example 28a) and N,N-diisopropylethylamine (DIEA, 0.145 ml, 0.825 mmol) in CH$_2$Cl$_2$ (10 mL) is added TBTU (246 mg, 0.765 mmol). After the reaction is stirred under nitrogen for 20 minutes, 2-(5-[N-tert-butoxycarbonyl] carbamimidoyl-2,3-dihydrobenzo-furan-3-yl)ethylamine (0.229 g, 0.750 mmol) (reference example 2) in DMF (15 mL) and DIEA (0.145 ml, 0.825 mmol) are added, and stirring is continued overnight. The reaction mixture is concentrated, and the resulting residue chromatographed (30:1, then 20:1 CH$_2$Cl$_2$: MeOH) to provide 0.360 g of the title compound as a foamy brown solid. $^1$H NMR (CDCl$_3$): δ1.33 (6H, s), 1.38 (9H, s), 1.54 (9H, s), 1.90 (1H, m), 2.01 (1H, m), 3.33 (2H, d, J=6.3 Hz), 3.50 (2H, m), 3.55 (1H, m), 4.31 (1H, br, m), 4.38 (1H, dd, J$_1$=9.0 Hz, J$_2$=6.0 Hz), 4.73 (1H, m), 6.52 (1H, br, m), 6.77 (1H, d, J=8.5 Hz), 7.46 (2H, d, J=8.2 Hz), 7.66 (1H, d, J=8.5 Hz), 7.76 (2H, d, J=8.2 Hz), 7.86 (1H, s). MS (ion spray) m/z: 581 (M+H)$^+$.

Reference Example 1d

By employing essentially the same procedure as used in reference example 1c, except using the product from reference example 31, there is prepared N-[2-(5-N-t-butoxycarbonylcarb-amimidoyl-2,3-dihydro-benzofuran-3-yl)-ethyl]-4-(3-N-t-butoxycarbonylamino-propyl)-benzamide. $^1$H NMR (DMSO) δ1.38 (s, 9H), 1.44 (s, 9H), 1.76 (m, 3H), 2.06 (m, 1H), 2.62 (m, 2H), 2.93 (m, 2H), 3.39 (m, 2H), 3.56 (m, 1H), 4.36 (m, 1H), 4.75 (m, 1H), 6.88 (m, 2H), 7.28 (m, 3H), 7.82 (m, 3H), 7.95 (bs, 1H), 8.50 (bt, 1H), 9.0 (bs, 1H). MS (ion spray) m/z 567 (M+H)$^+$.

General Procedure for Reference Example 1 e–1 aaa

A solution of 3-(2-aminoethyl)-5-(tert-butoxycarbonylcarbamimidoyl)-2,3-dihydrobenzofuran (Reference Example 2, 0.18 mL, 0.05 M in DMF) is added to 50 mg of the appropriate acylated 4-carbamoyl-2,3,5,6-tetrafluorophenol substituted resin (as disclosed in international patent application No. PCT/US99/14252, the contents of which are hereby incorporated herein by reference) (0.2 mmol/g), the mixture is shaken for 72 hours, and then filtered. The resin is washed with a further portion of DMF (1 mL), and then the combined filtrates are concentrated under high vacuum. The residue is used without further purification.

The following compounds are prepared using this procedure:

Reference Example 1e

N-[2-(5-[N-tert-butoxycarbonyl]-carbamimidoyl-2,
3-dihydro-benzofuran-3-yl)-ethyl]-2-(N-phenyl-
amino)-Benzamide

Reference Example 1f

N-[2-(5-[N-tert-butoxycarbonyl]-carbamimidoyl-2,
3-dihydro-benzofuran-3-yl)-ethyl]-2-(phenoxy)-
Benzamide

Reference Example 1g

N-[2-(5-[N-tert-butoxycarbonyl]-carbamimidoyl-2,
3-dihydro-benzofuran-3-yl)-ethyl]-4-(N,N-
diethylamino)-Benzamide

Reference Example 1h

N-[2-(5-[N-tert-butoxycarbonyl]-carbamimidoyl-2,
3-dihydro-benzofuran-3-yl)-ethyl]-4-(phenoxy)-
Benzamide

Reference Example 1i

N-[2-(5-[N-tert-butoxycarbonyl]-carbamimidoyl-2,
3-dihydro-benzofuran-3-yl)-ethyl]-2-methyl-3-
phenyl-prop-2-enoic acid amide

Reference Example 1j

N-[2-(5-[N-tert-butoxycarbonyl]-carbamimidoyl-2,
3-dihydro-benzofuran-3-yl)-ethyl]-10-cyano-
decanoic acid amide

Reference Example 1k

N-[2-(5-[N-tert-butoxycarbonyl]-carbamimidoyl-2,
3-dihydro-benzofuran-3-yl)-ethyl]-4-oxo-(4-
methoxy-phenyl)-butyramide

Reference Example 1l

N-[2-(5-[N-tert-butoxycarbonyl]-carbamimidoyl-2,
3-dihydro-benzofuran-3-yl)-ethyl]-(1-methyl-
pyrrole-2-carboxamide)

Reference Example 1m

N-[2-(5-[N-tert-butoxycarbonyl]-carbamimidoyl-2,
3-dihydro-benzofuran-3-yl)-ethyl]-(2,2-diphenyl-
propionamide)

Reference Example 1n

N-[2-(5-[N-tert-butoxycarbonyl]-carbamimidoyl-2,
3-dihydro-benzofuran-3-yl)-ethyl]-(2-(4-chloro-
phenoxy)-2-methyl-propionamide

Reference Example 1o

N-[2-(5-[N-tert-butoxycarbonyl]-carbamimidoyl-2,
3-dihydro-benzofuran-3-yl)-ethyl]-(2-[4-phenyl]-
phenyl-acetamide

Reference Example 1p

N-[2-(5-[N-tert-butoxycarbonyl]-carbamimidoyl-2,
3-dihydro-benzofuran-3-yl)-ethyl]-3-[3,4-
dimethoxy-phenyl]-prop-2-enoic acid amide

Reference Example 1q

N-[2-(5-[N-tert-butoxycarbonyl]-carbamimidoyl-2,
3-dihydro-benzofuran-3-yl)-ethyl]-(5-oxo-5-phenyl-
pentanoic acid amide

Reference Example 1r

N-[2-(5-[N-tert-butoxycarbonyl]-carbamimidoyl-2,
3-dihydro-benzofuran-3-yl)-ethyl]-xanthine-9-
carboxamide

Reference Example 1s

5-[1,2] dithiolan-3-yl-pentanoic acid-N-[2-(5-[N-
tert-butoxycarbonyl]-carbamimidoyl-2,3-dihydro-
benzofuran-3-yl)-ethyl]-amide

Reference Example 1t

N-[2-(5-[N-tert-butoxycarbonyl]-carbamimidoyl-2,
3-dihydro-benzofuran-3-yl)-ethyl]-5-methoxy-
indole-2 carboxamide

Reference Example 1u

N-[2-(5-[N-tert-butoxycarbonyl]-carbamimidoyl-2,
3-dihydro-benzofuran-3-yl)-ethyl]-3,4-
methylenedioxy cinnamic acid amide

Reference Example 1v

N-[2-(5-[N-tert-butoxycarbonyl]-carbamimidoyl-2,
3-dihydro-benzofuran-3-yl)-ethyl]-3-quinoline
carboxamide

Reference Example 1w 2,3-Dihydro-benzo[1,4]-dioxine-2-carboxylic Acid-
N-[2-(5-[N-tert-butoxycarbonyl]-carbamimidoyl-2,
3-dihydro-benzofuran-3-yl)-ethyl]-amide

Reference Example 1x

N-[2-(5-[N-tert-butoxycarbonyl]-carbamimidoyl-2,
3-dihydro-benzofuran-3-yl)-ethyl]-(2-[4-cyano-
phenoxy)-2-methyl-propionamide

Reference Example 1y

N-[2-(5-[N-tert-butoxycarbonyl]-carbamimidoyl-2,
3-dihydro-benzofuran-3-yl)-ethyl]-2-(4-oxo-3,4-
dihydro-pthalazin-1-yl)-acetamide

Reference Example 1z

3-Methyl-sulfanyl-4-oxo-4,5,6,7-tetrahydro-benzo
[c]-thiophene-1-carboxylic Acid N-[2-(5-[N-tert-
butoxycarbonyl]-carbamimidoyl-2,3-dihydro-
benzofuran-3-yl)-ethyl]-amide

Reference Example 1aa 4,5-Dimethyl-1-phenyl-pyrrole-3-carboxylic Acid
N-[2-(5-[N-tert-butoxycarbonyl]-carbamimidoyl-2,
3-dihydro-benzofuran-3-yl)-ethyl)-amide

Reference Example 1ab

4-Oxo-4H-9-thia-1,4a-diaza-fluorene-3-carboxylic
acid N-[2-(5-[N-tert-butoxycarbonyl]-
carbamimidoyl-2,3-dihydro-benzofuran-3-yl)-ethyl]-
amide Reference Example 1ac 6-(1-pyrazole)-nicotinic acid N-[2-(5-[N-tert-butoxycarbonyl]-carbamimidoyl-2,3-dihydro-benzofuran-3-yl)-ethyl]-amide Reference Example 1ad 3-Nitro-4-(1-pyrazolyl)benzoic Acid N-[2-(5-[N-tert-butoxycarbonyl]-carbamimidoyl-2,3-dihydro-benzofuran-3-yl)-ethyl]-amide Reference Example 1ae N-Tosyl-3-pyrrole-carboxylic Acid N-[2-(5-[N-tert-butoxycarbonyl]-carbamimidoyl-2,3-dihydro-benzofuran-3-yl)-ethyl]-amide Reference Example 1af 4-oxo-4,5,6,7-tetrahydro-benzofuran-3-carboxylic Acid [2-(5-[N-tert-butoxycarbonyl]-carbamimidoyl-2,3-dihydro-benzofuran-3-yl)-ethyl]-amide Reference Example 1ag 4-tert-butyl-2,6-dimethyl-cyclohexanecarboxylic Acid [2-(5-[N-tert-butoxycarbonyl]-carbamimidoyl-2,3-dihydro-benzofuran-3-yl)-ethyl]-amide Reference Example 1ah 5-methyl-1-(3-trifluoromethyl-phenyl)-4,5-dihydro-1H-[1,2,3]triazole-4-carboxylic Acid [2-(5-[N-tert-butoxycarbonyl]-carbamimidoyl-2,3-dihydro-benzofuran-3-yl)-ethyl]-amide Reference Example 1ai 2-benzylsulfanyl-N-[2-(5-[N-tert-butoxycarbonyl]-carbamimidoyl-2,3-dihydro-benzofuran-3-yl)-ethyl]-propionamide Reference Example 1aj 5-pyridin-2-yl-thiophene-2-carboxylic Acid (2-(5-[N-tert-butoxycarbonyl]-carbamimidoyl-2,3-dihydro-benzofuran-3-yl)-ethyl]-amide Reference Example 1ak 4-butyl-cyclohexanecarboxylic Acid [2-(5-[N-tert-butoxycarbonyl]-carbamimidoyl-2,3-dihydro-benzofuran-3-yl)-ethyl]-amide Reference Example 1al 5-methyl-1-phenyl-1H-pyrazole-4-carboxylic Acid [2-(5-[N-tert-butoxycarbonyl]-carbamimidoyl-2,3-dihydro-benzofuran-3-yl)-ethyl]-amide Reference Example 1am N-[2-(5-[N-tert-butoxycarbonyl]-carbamimidoyl-2,3-dihydro-benzofuran-3-yl)-ethyl]-6-pyrrol-1-yl-nicotinamide Reference Example 1an 4-chloro-1,3-dimethyl-1H-pyrazolo[3,4-b]pyridine-5-carboxylic Acid [2-(5-[N-tert-butoxycarbonyl]-carbamimidoyl-2,3-dihydro-benzofuran-3-yl)-ethyl]-amide Reference Example 1ao 4-methyl-2-(4-trifluoromethyl-phenyl)-thiazole-5-carboxylic acid [2-(5-[N-tert-butoxycarbonyl]-carbamimidoyl-2,3-dihydro-benzofuran-3-yl)-ethyl]-amide Reference Example 1ap (S)-2-(6-Methoxynaphthyl)-N-(2-[5-[N-tert-butoxycarbonyl]-carbamimidoyl-2,3-dihydrobenzofuran-3-yl]ethyl)propionamide. MS m/z=418 M+H.

Reference Example 1aq

N-(2-[5-Carbamimidoyl-2,3-dihydrobenzofuran-3-yl]ethyl)-3-chlorobenzothiophene-2-carboxamide Reference Example 1ar 4-Benzyloxy-N-(2-[5-[N-tert-butoxycarbonyl]-carbamimidoyl-2,3-dihydrobenzofuran-3-yl]ethyl)benzamide Reference Example 1as 4-(4-n-Propylphenyl)-N-(2-[5-[N-tert-butoxycarbonyl]-carbamimidoyl-2,3-dihydrobenzofuran-3-yl]ethyl)benzamide Reference Example 1at 2-Methylthio-N-(2-[5-[N-tert-butoxycarbonyl]-carbamimidoyl-2,3-dihydrobenzofuran-3-yl]ethyl)benzamide Reference Example 1au 3-(4-Pyridyl)-N-(2-[5-[N-tert-butoxycarbonyl]-carbamimidoyl-2,3-dihydrobenzofuran-3-yl]ethyl)acrylamide Reference Example 1av N-(2-[5-Carbamimidoyl-2,3-dihydrobenzofuran-3-yl]ethyl)-4-tert-butylcyclohexanecarboxamide Reference Example 1aw N-(2-[5-Carbamimidoyl-2,3-dihydrobenzofuran-3-yl]ethyl)-5-methylindole-2-carboxamide Reference Example 1ax N-(2-[5-Carbamimidoyl-2,3-dihydrobenzofuran-3-yl]ethyl)quinoline-6-carboxamide Reference Example 1ay N-(2-[5-Carbamimidoyl-2,3-dihydrobenzofuran-3-yl]ethyl)benzothiophene-2-carboxamide Reference Example 1az 2-Pyrrolyl-N-(2-[5-[N-tert-butoxycarbonyl]-carbamimidoyl-2,3-dihydrobenzofuran-3-yl]ethyl)benzamide Reference Example 1aaa 4-Methyl-2-phenyl-N-(2-[5-[N-tert-butoxycarbonyl]-carbamimidoyl-2,3-dihydrobenzofuran-3-yl]ethyl)-1,2,3-triazole-5-carboxamide Reference Example 1aab N-(2-[5-Carbamimidoyl-2,3-dihydrobenzofuran-3-yl]ethyl)-phthalide-3-acetamide Reference Example 1aac N-[2-(5-cyano-2,3-dihydro-Benzofuran-3-yl]-4-(phenyl)-Benzamide.

To a cooled (0° C.) solution of 2-(5-cyano-2,3-dihydro-benzofuran-3-yl)-ethyl amine (reference example 6, 382 mg, 2 mmol) in CH$_2$Cl$_2$ (9 mL) is added Et$_3$N (0.55 mL, 4 mmol) followed by 4-phenyl-benzoyl chloride (440 mg, 2.03 mmol). The resulting solution is stirred for 15 min. then diluted with ethyl acetate, washed with water and brine, dried over MgSO$_4$ and concentrated. The residue is purified by flash chromatography (50% ethyl acetate/10% CH$_2$Cl$_2$ in hexanes) to give the title compound (476 mg) as a solid $^1$H NMR (CDCl$_3$) d 1.96 (m, 1H), 2.10 (m, 1H), 3.50–3.70 (m, 3H), 4.50 (dd, J=9, 8 Hz, 1H), 4.83 (t, J=9 Hz, 1H), 6.31 (bt, 1H), 6.86 (d, J=8 Hz, 1H), 7.37-7.59 (m, 5H), 7.6-7.75 (m, 4H), 7.85 (d, J=8 Hz, 2H). MS (EI) m/z 368 (M)$^+$.

Reference Example 1aad

By employing essentially the same procedure as used in reference example 1aab, except using 4-(pyridin-3-yl)-benzoyl chloride there is prepared N-[2-(5-cyano-2,3-dihydro-Benzofuran-3-yl]-4-(pyridin-3-yl)-Benzamide. $^1$H NMR (CDCl$_3$) d 1.96 (m, 1H), 2.10 (m, 1H), 3.47–3.70 (m, 3H), 4.46 (dd, J=9, 8 Hz, 1H), 4.80 (t, J=9 Hz, 1H), 6.60 (bt, 1H), 6.84 (d, J=8 Hz, 1H), 7.40 (dd, J=7, 4 Hz, 1H), 7.50 (d, J=1 Hz, 1H), 7.54 (dd, J=8, 1 Hz, 1H), 7.64 (m, 3H), 7.90 (d, J=2 Hz, 2H), 8.65 (d, 1H), 8.84 (d, J=1 Hz, 1H). MS (EI) m/z 369 (M)$^+$.

Reference Example 1aae

By employing essentially the same procedure as used in reference example 1c, except using the product from reference examples 28b, and 6 as substrates there is prepared 4-(1-(t-Butyloxy-carbonylaminomethyl)-cyclopentyl)-N-[2-(5-cyano-2,3-dihydro-Benzofuran-3-yl)-ethyl]-benzamide. $^1$H NMR (CDCl$_3$) d 1.36 (s, 9H), 1.6–2.1 (m, 10H), 3.25 (bd, J=6 Hz, 2H), 3.42-3.68 (m, 3H), 4.17 (bs, 1H), 4.93 (bt, J=8 Hz, 1H), 4.77 (t, J=9 Hz, 1H), 6.33 (bt, 1H), 6.83 (d, J=8 Hz, 1H), 7.33 (bd, J=8 Hz, 2H), 7.45 (d, J=8 Hz, 1H), 7.49 (bs, 1H), 7.70 (bd, J=8 Hz, 2H). MS (ion spray) m/z 490 (M+H)$^+$.

Reference Examples 1aaf–1aak

The following compounds are prepared using essentially the same procedure described in reference example 1c except using the cited carboxylic acid.

Reference Example 1aal

N-[2-(5-cyano-2,3-dihydro-Benzofuran-3-yl)-ethyl]-4-(pyridine-N-oxid-3-yl)-benzamide Using the product from reference example 21.

Reference Example 1aam

N-[2-(5-cyano-2,3-dihydro-Benzofuran-3-yl)-ethyl]-4-(pyridin-4-yl)-benzamide

Using the product from reference Example 17a.

Reference Example 1aan

N-[2-(5-cyano-2,3-dihydro-Benzofuran-3-yl)-ethyl]-4-(6-oxo-1,6-dihydro-pyridin-3-yl)-benzamide Using the product from reference example 37.

Reference Example 1aao

N-[2-(5-cyano-2,3-dihydro-Benzofuran-3-yl)-ethyl]-4-[(3-(N-tert-butoxycarbonyl-aminomethyl)-phenyl]-benzamide Using the product from reference example 17f.

Reference Example 1aap

N-[2-(5-cyano-2,3-dihydro-Benzofuran-3-yl)-ethyl]-4-(pyridazin-3-yl)-benzamide

Using the product from reference example 17d.

Reference Example 1aaq

N-[2-(5-cyano-2,3-dihydro-Benzofuran-3-yl)-ethyl]-4-(pyridazin-4-yl)-benzamide

Using the product from reference example 17e.

Reference Example 1aar

N-[2-(5-cyano-2,3-dihydro-Benzofuran-3-yl)-ethyl]-4-(pyrimidin-5-yl)-benzamide

Using the product from reference example 17c

Reference Example 2

[2-(5-[N-(t-Butoxycarbonyl)-carbamimidoyl]-2,3-dihydro-benzofuran-3-yl)-ethylamine To a solution of O-Allyl-N-[2-(5-[N-(t-Butoxycarbonyl)-carbamimidoyl]-2,3-dihydro-benzofuran-3-yl)-ethyl]-carbamate (133 mg, 0.34 mmol) (reference example 3) in CH$_2$Cl$_2$ (2 mL) was added morpholine (135 mL, 1.55 mmol) followed by (Ph$_3$P)$_4$Pd (9 mg, 8 mmol). This solution was stirred for 20 min then concentrated. The residue was purified by flash chromatography (eluting with 10% methanol/2% NH$_3$ in CH$_2$Cl$_2$) to give 73 mg of the title compound as an oil. $^1$H NMR (CDCl$_3$) d 1.52 (s, 9H), 1.70 (m, 1H), 1.90 (m, 1H), 2.75 (m, 2H), 3.50 (m, 1H), 4.24 (dd, J=9, 8 Hz, 1H), 4.66 (t, J=9 Hz, 1H), 6.71 (d, J=8 Hz, 1H), 7.58 (dd, J=8, 1 Hz, 1H), 7.75 (bs, 1H). MS (FAB) m/z 306 (M+H)$^+$.

Reference Example 3

O-Allyl-N-[2-(5-[N-(t-Butoxycarbonyl)-carbamimidoyl]-2,3-dihydro-benzofuran-3-yl)-ethyl]-carbamate To a solution of O-Allyl-N-(2-(5-carbamimidoyl-2,3-dihydro-benzofuran-3-yl)-ethyl]-carbamate acetate salt (1.4 g, 4 mmol) (reference example 4) in CH$_2$Cl$_2$ (28 mL) was added Et$_3$N (1.5 mL, 10.8 mmol) followed by di-t-buytlcarbonate (1.16 g, 5.3 mmol). The resulting mixture was stirred for 1 hr then concentrated. The residue was purified by flash chromatography (eluting with 40% ethyl acetate in hexanes to give 1.1 g of the title compound. $^1$H NMR (CDCl$_3$) d 1.50 (s, 9H), 1.75 (m, 1H), 1.91 (m, 1H), 3.24 (m, 2H), 3.45 (m, 1H), 4.29 (dd, J=9, 8 Hz, 1H), 4.53 (d, J=6 Hz, 2H), 4.67 (t, J=9 Hz, 1H), 5.0 (bt, J=6 Hz, 1H), 5.2 (d, J=11 Hz, 1H), 5.27 (d, J=17 Hz, 1H), 5.88 (m, 1H), 6.73 (d, J=8 Hz, 1H), 7.63 (bd, J=8 Hz, 1H), 7.79 (bs, 1H). MS (ion spray) m/z 390 (M+H)$^+$.

Reference Example 4

O-Allyl-N-[2-(5-carbamimidoyl-2,3-dihydro-benzofuran-3-yl)-ethyl]-carbamate acetate salt To a solution of O-Allyl-N-[2-(5-cyano-2,3-dihydro-benzofuran-3-yl)-ethyl]-carbamate (3.36 g, 12.3 mmol) (reference example 5) in 10% triethylamine/pyridine (84 mL) was added H$_2$S gas in a slow stream for 10 min. The resulting green colored solution was stirred for 24 hr then concentrated under reduced pressure. The residue was taken up in toluene and this solution concentrated under reduced pressure. This residue was dissolved in acetone (84 mL) then methyl iodide added (20 mL, 311 mmol). The resulting solution was warmed to 60° C. and stirred at this temperature for 1 hr. The solution was allowed to cool to room temperature then concentrated. The residue was dissolved in methanol (84 mL) then ammonium acetate added (10.92 g, 131 mmol). The resulting solution was warmed to 60° C. then stirred at this temperature for 4 hr. The solution was allowed to cool to room temperature then stirred for 18 hr before being concentrated under vacuum. The residue was purified by flash chromatography (eluting with 10% then 15% methanol in $CH_2Cl_2$) to give 3.62 g of the title compound. $^1$H NMR ($CD_3OD$) d 1.80 (m, 1H), 1.98 (s, 3H), 2.0 (m, 1H), 3.23 (m, 2H), 3.61 (m, 1H), 4.40 (dd, J=9, 8 Hz, 1H), 4.53 (d, J=6 Hz, 2H), 4.80 (t, J=9 Hz, 1H), 5.18 (d, J=11 Hz, 1H), 5.3 (d, J=17 Hz, 1H), 5.92 (m, 1H), 6.92 (d, J=8 Hz, 1H), 7.1 (bt, J=6 Hz, 1H), 7.66 (dd, J=8, 1 Hz, 1H), 7.75 (bs, 1H). MS (ion Spray) m/z 290 $(M+H)^+$.

Reference Example 5

O-Allyl-N-[2-(5-cyano-2,3-dihydro-benzofuran-3-yl)-ethyl]-carbamate

To a solution of 2-(5-cyano-2,3-dihydro-benzofuran-3-yl)-ethyl azide (3.3 g, 15.4 mmol) (reference example 7) in THF 60 mL) was added $(Ph)_3P$ (4.44 g, 16.7 mmol). The resulting mixture was stirred for 5 hr then water (594 mL, 30.3 mmol) was added. This solution was stirred for 18 hr then a solution of sodium carbonate (4.0 g, 37.7 mmol) in water (20 mL) was added. To this mixture was added allyl chloroformate (1.75 mL, 16.5 mmol). The resulting mixture was stirred for 20 min then diluted with ethyl acetate. The ethyl acetate solution was washed, sequentially, with water and brine, dried over $MgSO_4$ and concentrated. The residue was purified by flash chromatography (eluting with 30% ethyl acetate in hexanes) to give 3.56 g of the title compound as a solid. $^1$H NMR ($CDCl_3$) d 1.81 (m, 1H), 1.98 (m, 1H), 3.30 (m, 2H), 3.55 (m, 1H), 4.38 (dd, J=9, 8 Hz, 1H), 4.60 (d, J=6 Hz, 1H), 4.76 (t, J=9 Hz, 1H), 4.91 (bt, J=6 Hz, 1H), 5.24 (d, J=11 Hz, 1H), 5.32 (d, J=17 Hz, 1H), 5.92 (m, 1H), 6.83 (d, J=8 Hz, 1H), 7.46 (m, 2H). MS (EI) m/z 273 $(M+H)^+$.

Reference Example 6

3-(2-Amino-ethyl)-5-cyano-2,3-dihydro-benzofuran

To a solution of 3-(2-azido-ethyl)-5-cyano-2,3-dihydro-benzofuran (434 mg, 2 mmol) (reference example 7) in THF (10 mL) was added $Ph_3P$ (576 mg, 2.2 mmol). The resulting solution was stirred for 7 hr then $H_2O$ added (72 ml, 4 mmol). This solution was stirred for 18 hr then concentrated. The residue was azeotroped with toluene then used without further purification. $^1$H NMR ($CDCl_3$) d 1.81 (m, 1H), 1.93 (m, 1H) 2.5 (bs, 2H), 2.81 (m, 2H), 3.60 (m, 1H), 4.32 (dd, J=8, 6 Hz, 1H), 4.73 (t, J=8 Hz, 1H) 6.83 (d, J=8 Hz, 1H), 7.46 (m, 2H).

Reference Example 7

3-(2-Azido-Ethyl)-5-Cyano-2,3-Dihydro-Benzofuran

To a cooled (0° C.) solution of 3-(2-hydroxy-ethyl)-5-cyano-2,3-dihydro-benzofuran (3.71 g, 19.6 mmol) (reference example 8) in $CH_2Cl_2$ (40 mL) was added $Et_3N$ (2.76 g, 20 mmol) and tosyl chloride (3.55 g, 18.7 mmol).

The cold bath was removed and stirring continued for 16 hr. The reaction mixture was then diluted with ethyl acetate and washed, sequentially, with water and brine, dried over $MgSO_4$ and concentrated. The residue was taken up in DMF (75 mL) then $NaN_3$ added (2.8 g, 43 mmol). The resulting mixture was warmed to 60° C. and stirred at this temperature for 5 hr. The reaction mixture was then allowed to cool to room temperature and diluted with ethyl acetate. This solution was then washed, sequentially, with water and brine, dried over $MgSO_4$ then concentrated. The residue was purified by flash chromatography (eluting with 20% ethyl acetate in hexanes) to give 3.31 g of the title compound as an oil which solidified on standing. $^1$H NMR ($CDCl_3$) d 1.85 (m, 1H), 2.00 (m, 1H), 3.41 (m, 2H), 3.57 (m, 1H), 4.30 (dd, J=9, 8 Hz, 1H), 4.75 (t, J=9 Hz, 1H), 6.84 (d, J=8 Hz, 1H), 7.43 (m, 2H). MS (EI) m/z 214 $(M)^+$.

Reference Example 8

3-(2-hydroxy-ethyl)-5-cyano-2,3-dihydro-benzofuran

To a cooled (0° C.) solution of 3-(carboxy-methyl)-5-cyano-2,3-dihydro-benzofuran (approx. 3.48 g, 17 mmol) (reference example 9 or in enantiomerically pure form, reference example 13) in THF (60 mL) was added $BH_3$:THF (19 mL, 1M in THF). The cold bath was removed and stirring continued for 17 hr. The reaction was quenched with 1 M aqueous HCl and the resulting mixture diluted with ethyl acetate. This solution was washed sequentially, with sat. aqueous $NaHCO_3$, and brine, dried over $MgSO_4$ and concentrated to give 3.7 g of crude alcohol which solidified on standing. $^1$H NMR ($CDCl_3$) d 1.85 (m, 1H), 2.03 (m, 1H), 3.67 (m, 1H), 3.78 (m, 2H), 4.40 (dd, J=9, 8 Hz, 1H), 4.80 (t, J=9 Hz, 1H), 6.84 (d, J=8 Hz, 1H), 7.45 (m, 2H). MS (EI) m/z 190 $(M+H)^+$.

Reference Example 9

3-(carboxy-methyl)-5-cyano-2,3-dihydro-benzofuran

To a solution of methyl [5-cyano-2,3-dihydro-benzofuran-3-yl]-acetate (3.73 g, 17.2 mmol) (reference example 10a) in THF:MeOH (2:1, 60 mL) was added aqueous NaOH (16 mL, 2M). The resulting mixture was stirred for 10 min then acidified to pH 1 with 2M aqueous HCl. This mixture was diluted with ethyl acetate and washed, sequentially, with water and brine, dried over $MgSO_4$ and concentrated. The crude solid product was used without further purification. $^1$H NMR ($CDCO_3$) d 2.70 (dd, 16, 8 Hz, 1H), 2.85 (dd, J=16, 5 Hz, 1H), 3.91 (m, 1H), 4.38 (dd, J=8, 6 Hz, 1H), 4.85 (t, J=8 Hz, 1H), 6.84 (d, J=8 Hz, 1H), 7.47 (m, 2H). MS (EI) m/z 203 $(M)^+$.

Reference Example 10a

Methyl [5-Cyano-2,3-Dihydro-Benzofuran-3-yl]-Acetate

To a cooled (−100° C.) solution of methyl 4-[4-cyano-2-iodo-phenoxy]-but-2-enoate (4.3 g, 12.5 mmol) (reference example 1 a) in THF: $Et_2O$ (4:1, 125 mL) was added dropwise n-buLi (5.5 mL, 2.5 M in hexanes). On complete addition, the reaction mixture was stirred for 15 min then quenched with 1 M aqueous HCl (20 mL). This mixture was diluted with ethyl acetate and washed, sequentially, with water and brine, dried over $MgSO_4$ and concentrated. The residue was purified by flash chromatography (eluting with 25% ethyl acetate in hexanes) to give 3.73 g of the title compound. $^1$H NMR (CDCl$_3$) d 2.63 (dd, 16, 8 Hz, 1H), 2.80 (dd, J=16, 5 Hz, 1H), 3.74 (s, 3H), 3.91 (m, 1H), 4.35 (dd, J=8, 6 Hz, 1H), 4.86 (t, J=8 Hz, 1H), 6.84 (d, J=8 Hz, 1H), 7.47 (m, 2H). MS (EI) m/z 203 (M)$^+$. MS (EI) m/z 217 (M)$^+$.

Using essentially the same procedure described in reference example 10a, except using methyl 4-[2-iodo-phenoxy]-but-2-enoate (referece example 11b), there is prepared

Reference Example 10b

Methyl [2,3-Dihydro-Benzofuran-3-yl]-Acetate $^1$H NMR (CDCl$_3$) d 2.59 (dd, J=16, 9 Hz, 1H), 2.80 (dd, J=16, 6 Hz, 1H), 3.73 (s, 3H), 3.87 (m, 1H), 4.26 (dd, J=8, 6 Hz, 1H), 4.77 (t, J=8 Hz, 1H), 6.84 (m, 2H), 7.14 (m, 2H). MS m/z 192 (M+).

Reference Example 11a

Methyl 4-[4-Cyano-2-Iodo-Phenoxy]-But-2-enoate

To a cooled (0° C.) suspension of NaH (1.5 g of 60% suspension in mineral oil, 38 mmol) in THF (80 mL) was added a solution comprised of 4-hydroxy-3-iodo-benzonitrile (8.4 g, 34 mmol) (reference example 12), methyl bromo-crotonate (6.65 mL tech. grade, approx. 51 mmol) and DMPU (10 mL) in THF (20 mL). On complete addition, the cold bath was removed and replaced with an oil bath. The reaction mixture was heated to 55° C. and stirred at this temperature for 4.5 hr, cooled to room temperature and acidified with 2M aqueous HCl. The mixture was then diluted with ethyl acetate, washed sequentially with water and brine, dried over MgSO$_4$ and concentrated. The residue was triturated with hexane several times, leaving 8.6 g of the title compound as a solid. $^1$H NMR (CDCl$_3$) d 3.78 (s, 3H), 4.80 (dd, J=4, 1 Hz, 1H), 6.35 (dt, J=16, 1 Hz, 1H), 6.79 (d, J=8 Hz, 1H), 7.05 (dt, J=16, 4 Hz, 1H), 7.60 (dd, J=8, 1 Hz, 1H), 8.06 (d, J=1 Hz, 1H). MS (EI) m/z 343 (M)$^+$.

Using essentially the same procedure described in reference example 11a, except using 2-iodo-phenol as substrate, there is prepared:

Reference Example 11b

Methyl 4-[2-iodo-phenoxy]-but-2-enoate

Purified by flash chromatography (10% Ethyl acetate/10% CH$_2$Cl$_2$ in hexanes). $^1$H NMR (CDCl$_3$) d 3.78 (s, 3H), 4.75 (m, 2H), 6.40 (dt, J=16, 1 Hz, 1H), 6.77 (m, 2H), 7.09 (dt, J=16, 4 Hz, 1H), 7.30 (m, 1H), 7.80 (m, 1H). MS m/z 318 (M+)

Reference Example 12

4-Hydroxy-3-Iodo-Benzonitrile

To a solution of 4-hydroxy-3-iodo-benzaldehyde (7.9 g, 31.8 mmol) (prepared by the method of Barnes at al.; J. Chem. Soc., 1950, 2824) in xylene (120 mL) was added hydroxylamine hydrochloride (2.34 g, 33.4 mmol), magnesium sulphate (12.7 g) and p-toluene sulphonic acid monohydrate (1.27 g, 6.4 mmol). The resulting mixture was heated to reflux and stirred at this temperature for 90 min. The reaction mixture was then allowed to cool to room temperature and filtered. The solid was washed with ethyl acetate then the combined filtrates concentrated. The residue was purified by flash chromatography (eluting with 30% ethyl acetate in hexanes) to give 6.57 g of the title compound. $^1$H NMR (CDCl$_3$) d 6.1 (bs, 1H), 7.05 (d, J=8 Hz, 1H), 7.55 (dd, J=8, 1 Hz, 1H), 7.99 (d, J=1 Hz, 1H).

Reference Example 13

3-(2-hydroxy-ethyl)-5-cyano-2,3-dihydro-benzofuran

To a mixture of zinc cyanide (1.97 g, 17 mmol) and (Ph$_3$P)$_4$Pd (498 mg, 0.4 mmol) is added 3-(2-hydroxy-ethyl)-5-bromo-2,3-dihydro-benzofuran (reference example 14, 1.1 g, 4.3 mmol) in DMF (12 mL). The resulting mixture is heated to 75° C. and stirred at this temperature for 14 hr. The reaction mixture is then allowed to cool then diluted with ethyl acetate, washed with 5% aq. ammonia solution then brine. The organic phase is dried over Mg SO$_4$ then concentrated. The residue is purified by flash chromatography (50% ethyl acetate in hexanes) to give the product (653 mg) as a white solid.

Reference Example 14

3-(2-hydroxy-ethyl)-5-bromo-2,3-dihydro-benzofuran

A solution of 5-bromo-3-(carboxymethyl)-2,3-dihydro-benzofuran (reference example 15, 1.86 g , 7.68 mmol) in THF (21 mL) is cooled to 0° C. then a solution of borane in THF (7.7 mL, 1 M). On complete addition the cold bath is removed and stirring continued for 12 h. The reaction is quenched with aq. HCl (2M) diluted with ethyl acetate washed with sat. NaHCO$_3$ solution then brine, dried over MgSO$_4$ and concentrated. The residue is purified by flash chromatography (30% ethyl acetate in hexanes) to give the title compound (1.1 g) as an oil. $^1$H NMR (CDCl$_3$) d 1.55 (bs, 1H), 1.88 (m, 1H), 2.03 (m, 1H), 3.61 (m, 1H), 3.75 (t, J=6 Hz, 2H), 4.29 (dd, J=8, 7 Hz, 1H), 4.68 (t, J=8 Hz, 1H), 6.68 (d, J=8 Hz, 1H), 7.22 (dd, J=8, 1 Hz, 1H), 7.28 (d, J=1 Hz, 1H). MS m/z242/244 Br pattern (M+).

Reference Example 15

5-bromo-3-(carboxymethyl)-2,3-dihydro-benzofuran

To a solution of 3-(carboxymethyl)-2,3-dihydro-benzofuran (reference example 16, 1.26 g, 7.7 mmol) in CH$_2$Cl$_2$ (24 mL) is added, dropwise, a solution of Br$_2$ in CH$_2$Cl$_2$ (7 mL, 1 M). On complete addition the solution is stirred for a further 25 min. The reaction mixture is concentrated under vacuum to give the title compound (1.86 g) as a tan solid. $^1$H NMR (CDCl$_3$) d 2.67 (dd, J=16, 8 Hz, 1H), 2.85 (dd, J=16, 6 Hz, 1H), 3.88 (m, 1H), 4.29 (t, J=8 Hz, 1H), 4.79 (t, J=8 Hz, 1H), 6.69 (d, J=8 Hz, 1H), 7.26 (m, 2H). MS m/z 256/258 Br pattern (M+).

Reference Example 16

3-(carboxymethyl)-2,3-dihydro-benzofuran

To a solution of methyl [2,3-Dihydro-Benzofuran-3-yl]-acetate (reference example 10b, 6.18 g, 32 mmol) in THF (40 mL), methanol (40 mL) is added a solution of NaOH (40 mL, 1 M). The resulting solution is stirred for 2 hr then acidified with HCl (25 mL, 2M), diluted with ether, washed with brine, dried over MgSO$_4$ and concentrated. The residue crystallized on standing to give the title compound (5.62 g) as a colorless solid. $^1$H NMR (CDCl$_3$) d 2.69 (dd, J=16, 9 Hz, 1H), 2.89 (dd, J=16, 6 Hz, 1H), 3.88 (m, 1H), 4.30 (dd, J=8, 6 Hz, 1H), 4.77 (t, J=8 Hz, 1H), 6.86 (m, 2H), 7.18 (m, 2H). The racemic acid, prepared above, can be resolved into individual enantiomers by recrystallization of the salt of racemic 3-(carboxy-methyl)-2,3-dihydro-benzofuran (1 eq) with enantiomerically pure a-methylbenzyl amine (0.5 eq)

from isopropanol. The free acid is generated from the salt by dissolving the salt in excess aq. HCl (1 M) and extracting the acid into ether. The ether extract is dried over $MgSO_4$ and concentrated to give the enantiomerically pure title compound ad ($CH_2Cl_2$, C=10 mg/mL)=−8.4 (using D-(+) a-methyl benzyl amine.

Reference Example 17a

4-[Pyridin-4-yl]-Benzoic Acid

To a suspension of 4-[pyridin-4-yl]-benzaldehyde (approx. 2.8 g, 15 mmol) (reference example 8a) in t-butanol (100 mL) was added 2-methy-but-2-ene (15 mL) followed by a solution comprised of $NaClO_2$ (14.7 g, tech. grade) and $NaH_2PO_4.H_2O$ (14.7 g, 105 mmol) in $H_2O$ (100 mL). This mixture was stirred for 20 min then the precipitated solid filtered off. This solid was washed with water then set aside. The organic phase of the mother liquor was separated then washed with brine, dried over $MgSO_4$ and concentrated to give a solid. This material was combined with the solid obtained by filtration and dried under vacuum to give 2.34 g of the title compound. $^1$H NMR (DMSO) d 7.77 (d, J=6 Hz, 2H), 7.93 (d, J=8 Hz, 2H), 8.06 (d, J=8 Hz, 2H), 8.70 (d, J=6 Hz, 2H). MS (EI) m/z 199 (M)$^+$.

Reference Example 17b

By employing essentially the same procedure as used in reference example 17a, except using the product from reference example 18b, there is prepared 4-[Pyridin-3-yl]-Benzoic Acid. $^1$H NMR (DMSO) d 7.52 (dd, J=8, 5 Hz, 1H), 7.87 (d, J=8 Hz, 2H), 8.06 (d, J=8 Hz, 2H), 8.15 (dd, J=8, 2 Hz, 1H), 8.62 (dd, J=5, 2 Hz, 1H), 8.96 (s, 1H), 13.05 (bs, 1H). MS (EI) m/z 199 (M)$^+$.

Reference Example 17c

By employing essentially the same procedure as used in reference example 17a, except using the product from reference example 18c, there is prepared 4-[Pyrimidin-5-yl]-Benzoic Acid. $^1$H NMR (DMSO) d 7.95 (d, J=8 Hz, 2H), 8.10 (d, J=8 Hz, 2H), 9.23 (s, 2H), 9.25 (s, 1H), MS (EI) m/z 200 (M)$^+$.

Reference Example 17d

By employing essentially the same procedure as used in reference example 17a, except using the product from reference example 18d, there is prepared 4-[Pyridazin-3-yl]-Benzoic Acid. $^1$H NMR (DMSO) d 7.85 (dd, J=8, 4 Hz. 1H), 8.1 (d, J=8 Hz, 2H), 8.29 (d, J=8 Hz, 2H), 8.31 (d, J=8 Hz, 1H), 9.26 (d, J=4 Hz, 1H). MS (EI) m/z 200 (M)$^+$.

Reference Example 17e

By employing essentially the same procedure as used in reference example 17a, except using the product from reference example 18e, there is prepared 4-[Pyridazin-4-yl]-Benzoic Acid. $^1$H NMR (DMSO) d 8.10 (m, 5H), 9.33 (d, J=4 Hz, 1H), 9.67 (bs, 1H). MS (EI) m/z 200 (M)$^+$.

Reference Example 17f

By employing essentially the same procedure as used in reference example 17a, except using the product from reference example 18f, there is prepared 3'-[N-(t-Butoxycarbonyl)-Aminomethy]-Biphenyl-4-Carboxylic Acid. $^1$H NMR (CDCl$_3$) d 1.46 (s, 9H), 4.40 (d, J=6 Hz, 2H), 7.30 (bd, J=6 Hz, 1H), 7.41 (t, J=8 Hz, 1H), 7.55 (d, J=8 Hz, 2H), 7.68 (d, J=8 Hz, 2H), 8.14 (m, 2H), MS (FAB),/z 328 (M+H)$^+$.

Reference Example 17g

By employing essentially the same procedure as used in reference example 71a, except using the product from reference example 18g, there is prepared 4-(2-methoxy-pyridin-5-yl)-benzoic acid. $^1$H NMR (DMSO) δ3.92 (s, 3H), 6.95 (d, J=9 Hz, 1H), 7.80 (d, J=8 Hz, 2H), 8.02 (d, J=8 Hz, 2H), 8.10 (dd, J=9, 2 Hz), 8.58 (d, J=2 Hz, 1H). MS (EI) m/z 229 (M+).

Reference Example 18a

4-[Pyridin-4-yl]-Benzaldehyde. To a cooled (−78° C.) solution of oxalyl chloride in $CH_2Cl_2$ (15 mL, 1M) was added, dropwise, DMSO (3 mL). The resulting solution was stirred for 5 min then a solution of 4-[pyridin-4-yl]-benzyl alcohol (2.80 g, 15 mmol) (reference example 19a) in $CH_2Cl_2$/DMSO (27 mL, 3:1 $CH_2Cl_2$/DMSO) was added dropwise. The resulting mixture was stirred 5 min then Et$_3$N added (15 mL, 108 mmol) in one portion. The cold bath was removed and stirring continued for 15 min. The reaction mixture was then diluted with ethyl acetate, washed with water and then brine, dried over $MgSO_4$ and concentrated. The crude, orange solid product was used without further purification.

Reference Example 18b

By employing essentially the same procedure as used in reference example 18a, except using the product from reference example 19b, there is prepared 4-[Pyridin-3-yl]-Benzaldehyde.

Reference Example 18c

By employing essentially the same procedure as used in reference example 18a, except using the product from reference example 19c, there is prepared 4-[Pyrimidin-5-yl]-Benzaldehyde.

Reference Example 18d

By employing essentially the same procedure as used in reference example 18a, except using the product from reference example 24a, there is prepared 4-[Pyridazin-3-yl]-Benzaldehyde.

Reference Example 18e

By employing essentially the same procedure as used in reference example 18a, except using the product from reference example 24b, there is prepared 4-[Pyridazin-4-yl]-Benzaldehyde.

Reference Example 18f

By employing essentially the same procedure as used in reference example 18a, except using the product from reference example 24c, there is prepared 4-(3-[N-(t-Butyloxy-Carbonyl)-Aminomethy]-phenyl)-Benzaldehyde

Reference Example 18g

By employing essentially the same procedure as used in reference example 18a, except using the product from reference example 19d, there is prepared 4-(2-methoxy-pyridin-5-yl)-benzaldehyde. $^1$H NMR (CDCl$_3$) δ4.00 (s, 3H), 6.86 (d, J=9 Hz, 1H), 7.70 (d, J=8 Hz, 2H), 7.84 (dd, J=9, 2 Hz, 1H), 7.96 (d, J=8 Hz, 2H), 8.46 (d, J=2 Hz, 1H).

Reference Example 19a

4-[Pyridin-4-yl]-Benzyl alcohol

To a cooled (−78° C.) solution of 4-bromo-benzyl-(t-butyldimethylsilyl)-ether (5.46 g, 18 mmol) (reference example 20) in THF (40 mL) was added, dropwise, n-buLi (8.8 mL, 2.5M in hexanes). On complete addition, the resulting solution was stirred for 10 min then $ZnCl_2$ (40 mL, 0.5M in THF) was added. The cold bath was removed and stirring continued for 10 min. To this solution was added 4-bromo-pyridine* (approx. 2.2 mL, 22 mmol) in hexanes (25 mL) followed by $(Ph_3P)_4Pd$ (900 mg, 0.77 mmol). The resulting mixture was heated to 60° C. and stirred at this temperature for 1 hr. The reaction mixture was allowed to cool to room temperature then diluted with ether, washed, sequentially, with 5% aqueous ammonium hydroxide solution and brine, dried over $MgSO_4$ and concentrated. The residue was taken up in THF (30 mL) and treated with n-$Bu_4NF$ (25 mL, 1M in THF). The resulting solution was stirred for 25 min then diluted with ethyl acetate, washed with water and brine, dried over $MgSO_4$ and concentrated. The residue was triturated with ether, filtered and the solid dried under vacuum to give 2.8 g of the title compound as a tan solid.

* 4-bromo-pyridine was obtained from its HCl salt by dissolving the salt in cold 1M NaOH (5% excess) then extracting with cold hexane. The hexane extract was dried over $MgSO_4$ and used without further manipulation.

Reference Example 19b

By employing essentially the same procedure as used in reference example 19a, except using 3-bromo-pyridine, there is prepared 4-[Pyridin-3-yl]-Benzyl alcohol. $^1$H NMR (DMSO) d 4.55 (d, J=6 Hz, 2H), 5.25 (t, J=6 Hz, 1H), 7.44 (d, J=8 Hz, 2H), 7.48 (dd, J=8, 5 Hz, 1H), 7.68 (d, J=8 Hz, 2H), 8.07 (dt, J=8, 2 Hz, 1H), 8.56 (dd, J=5, 2 Hz, 1H), 8.88 (d, J=2 Hz, 1H). MS (EI) m/z 185 $(M)^+$.

Reference Example 19c

By employing essentially the same procedure as used in reference example 19a, except using 5-bromo-pyrimidine, there is prepared 4-[Pyrimidin-5-yl] Benzyl Alcohol. $^1$H NMR ($CDCl_3$) d 2.61 (bs, 1H), 4.80 (d, J=7 Hz, 2H), 7.55 (m, 4H), 8.88 (s, 2H), 9.20 (s, 1H). MS (EI) m/z 186 $(M)^+$.

Reference Example 19d

By employing essentially the same procedure as used in reference example 9a, except using 5-bromo-2-methoxy-pyridine, there is prepared 4-(2-methoxy-pyridin-5-yl)-benzyl alcohol. $^1$H NMR ($CDCl_3$) δ3.98 (s, 3H), 4.70 (bs, 1H), 4.74 (bs, 2H), 6.82 (d, J=9 Hz, 1H), 7.44 (d, J=8 Hz, 2H), 7.52 (d, J=8 Hz, 2H), 7.79 (dd, J=9, 2 Hz, 1H), 8.38 (d, J=2 Hz, 1H). MS (EI) m/z 215 $(M)^+$.

Reference Example 20

4-Bromobenzyl-(t-butyldimethylsilyl)-ether

To a cooled (0° C.) solution of 4-bromo-benzyl alcohol (3.74 g, 20 mmol) in ether (80 mL) was added 2,6-lutidine (2.6 mL, 22 mmol) followed by t-butyldimethylsilyl trifluoromethanesulphonate (5.05 mL, 22 mmol). The resulting mixture was stirred for 40 min then diluted with ether, washed, sequentially, with water and brine dried over MgSO4 and concentrated. The residue was purified by flash chromatography (eluting with 5% ether in hexanes) to give 6.0 g of the title compound as an oil. $^1$H NMR ($CDCl_3$) d 0.09 (s, 6H), 0.93 (s, 9H), 4.68 (s, 2H), 7.18 (d, J=8 Hz, 2H), 7.44 (d, J=8 Hz, 2H). MS (EI) m/z 300 $(M)^+$.

Reference Example 21

4-[pyridine-N-oxide-3-yl]-Benzoic Acid

To a solution of methyl 4-[pyridine-N-oxide-3-yl]-benzoate (reference example 22) in THF/$CH_3OH$ (4 mL, 1:1) was added a 1M solution of aqueous NaOH (1.5 mL). The resulting mixture was stirred for 18 hr then acidified with a 1M solution of aqueous HCl (1.6 mL). The precipitated solid was filtered, washed, sequentially, with water and ethyl acetate then dried under vacuum to give 214 mg of the title compound as a white solid. $^1$H NMR (DMSO) d 7.54 (t, J=7 Hz, 1H), 7.71 (d, J=7 Hz, 1H), 7.90 (d, J=8 Hz, 2 H), 8.04 (d, J=8 Hz, 2H), 8.29 (d, J=7 Hz, 1H), 8.67 (s, 1H). MS (EI) m/z 215 $(M+)^+$.

Reference Example 22

Methyl 4-[pyridine-N-oxide-3-yl]-benzoate

To a cooled (0° C.) solution of methyl 4-[pyridin-3-yl]-benzoate (1.74 g, 8.2 mmol) (reference example 23) in $CH_2Cl_2$ (41 mL) was added m-CPBA (2.02 g, 70% technical grade, 8.2 mmol). The resulting solution was stirred for 1 hr then a further portion of m-CPBA added (1.01 g, 4.1 mmol). This solution was stirred for 1 hr (temperature held between 5–10° C.) then the reaction mixture poured directly onto a silica gel column. Elution with 10% MeOH/40% EtOAc/ 50% $CH_2Cl_2$ gave 1.67 g of the title compound as a white solid. $^1$H NMR ($CDCl_3$) d 3.96 (s, 3H), 7.38 (t, J=8 Hz, 1H), 7.50 (d, J=8 Hz, 1H), 7.63 (m, 2H), 8.17 (m, 2H), 8.25 (d, J=8 Hz, 1H), 8.49 (s, 1H). MS (EI) m/z 229 $(M)^+$.

Reference Example 23

Methyl 4-[Pyridin-3-yl]-Benzoate

To a solution of 4-[pyridin-3-yl]-benzoic acid (2.2 g, 11 mmol) (reference example 17b) in methanol (33 mL) was added conc. $H_2SO_4$ (5 mL). The resulting solution was warmed to 60° C. and stirred at this temperature for 45 min. The reaction mixture was then allowed to cool to room temperature then poured into ice. The pH of the resulting solution was adjusted to 7 using a 10 M solution of NaOH. The product was then extracted into ethyl acetate. This solution was washed with brine, dried over $MgSO_4$ and concentrated to give 1.74 g of the title compound as a tan solid. $^1$H NMR ($CDCl_3$) d 3.96 (s, 3H), 7.40 (dd, J=8, 5 Hz, 1H), 7.66 (m, 2H), 7.93 (m, 1H), 8.15 (m, 2H), 8.65 (bs, 1H), 8.89 (bs, 1H). MS (EI) m/z 213 $(M)^+$.

Reference Example 24a

4-[Pyridazin-3-yl]-Benzyl Alcohol

To a solution of 4-[pyridazin-3-yl]-benzyl-(t-butyldimethylsilyl)ether (2.71 g, 9 mmol) (reference example 25, less polar product) was added a solution of tetra-n-butylammonium fluoride in THF (12 mL, 1M). The resulting solution was stirred for 15 min then diluted with ethyl acetate. This solution was washed with water then brine. The aqueous washings were back extrated with 10% methanol in $CH_2Cl_2$. The combined organic extracts were dried over $MgSO_4$ then concentrated. The residue was purified by flash chromatography (eluting with ethyl acetate) to give 1.50 g of the title compound as a white solid. $^1$H NMR ($CDCl_3$) d 2.28 (t, J=5 Hz, 1H), 4.79 (d, J=5 Hz, 2H), 7.50 (m, 3H), 7.85 (dd, J=8, 1 Hz, 1H), 8.05 (d, J=8 Hz, 2H), 9.13 (dd, J=5, 1 Hz, 1) MS (EI) m/z 186 $(M)^+$.

Reference Example 24b

By employing essentially the same procedure as used in reference example 24a, except using the more polar product from reference example 25, there is prepared 4-[Pyridazin-4-yl]-Benzyl Alcohol. $^1$H NMR ($CDCl_3$) d 2.20 (t, J=6 Hz, 1H), 4.79 (d, J=6 Hz, 2H), 7.53 (d, J=8 Hz, 2H), 7.63 (m, 3H), 9.18 (d, J=4 Hz, 1H), 9.42 (bs, 1H). MS (EI) m/z 186 (M)+.

Reference Example 24c

By employing essentially the same procedure as used in reference example 24a, except using the product from reference example 26a, there is prepared 4-(3-[N-(t-Butoxycarbonyl)-Aminomethy]-phenyl)-Benzyl Alcohol. $^1$H NMR (CDCl$_3$) d 1.36 (s, 9H), 4.25 (d, J=6 Hz, 2H), 4.65 (s, 2H), 7.15 (m, 2H), 7.25–7.40 (m, 4H), 7.45 (d, J=8 Hz, 2H). MS (EI) m/z 313 (M+).

Reference Example 25

4-[Pyridazin-3-yl]-Benzyl-(t-Butyldimethylsilyl) Ether and 4-[Pyridazin-4-yl]-Benzyl-(t-Butyidimethylsilyl)Ether To a solution cooled (−78° C.) of 4-bromobenzyl(t-butyldimethylsilyl)-ether (9.03 g, 30 mmol) (reference example 10) in THF (60 mL) was added, dropwise, n-BuLi (12.6 mL, 2.5M in hexanes). The resulting solution was stirred for 5 min then pyridazine (2.25 mL, 31 mmol) (Aldrich) was added in one portion. This solution was stirred for 20 min then aqueous HCl added (30 mL, 1M). The reaction mixture was diluted with ether, washed with brine dried over MgSO$_4$ and concentrated. The residue was taken up in acetone (45 mL) and this solution added to a solution of KMnO$_4$ in acetone (9.3 g, 60 mmol in approx. 200 mL). On complete addition, the brown colored mixture was stirred 5 min then filtered through celite. The mother liquor was concentrated and the residue purified by flash chromatography (eluting with 50% ethyl acetate in hexanes) to give 2.71 g of 4-[pyridazin-3-yl]-benzyl-(t-butyldimethylsilyl) ether: $^1$H NMR (CDCl$_3$) d 0.12 (s, 6H), 0.99 (s, 9H), 4.83 (s, 2H), 7.50 (d, J=8 Hz, 2H), 7.53 (dd, J=8, 5 Hz, 1H), 7.85 (dd, J=8, 1 Hz, 1H), 8.06 (d, J=8 Hz, 2H), 9.14 (dd, J=5, 1 Hz, 1H). MS (EI) m/z 301 (M+H)+ and 2.0 g of 4-[pyridazin-4-yl]-benzyl-(t-butyldimethylsilyl)ether: $^1$H NMR (CDCl$_3$) d 0.11 (s, 6H), 0.96 (s, 9H), 4.80 (s, 2H), 7.47 (d, J=8 Hz, 2H), 7.63 (m, 3H), 9.20 (d, J=4 Hz, 1H), 9.45 (bs, 1H). MS (EI) m/z 301 (M+H)+.

Reference Example 26a 4-(3-[N-(t-Butoxycarbonyl)-aminomethy]-phenyl)-Benzyl-(t-Butyidimethylsilyl)Ether To a cooled (0° C.) solution of lithium aluminum hydride in THF (12 mL, 0.5M) was added a solution of 4-(3-cyano-phenyl)-Benzyl-(t-Butyidimethylsilyl)ether (2.0 g, 6.2 mmol) (reference example 27) in THF (4 mL). On complete addition, the reaction mixture was stirred until no starting material was detected by TLC analysis. At this point, water (240 ml) was added, dropwise, followed by 5N NaOH (240 ml) then a further portion of water (480 ml). This mixture was diluted with ether filtered through celite and the filtrate concentrated. The residue was taken up in THF (15 mL) then di-t-butyl carbonate added (1.5 g, 6.9 mmol). The resulting solution was stirred for 20 min then concentrated under reduced pressure. The residue was purified by flash chromatography (eluting with 5% then 10% ethyl acetate in hexanes) to give 1.0 g of the title compound as an oil. $^1$H NMR (CDCl$_3$) d 0.21 (s, 6H), 1.05 (s, 9H), 1.56 (s, 9H), 4.46 (d, J=5 Hz, 2H), 4.88 (s, 2H), 7.34 (m, 1H), 7.48 (m, 3H), 7.56 (m, 2H), 7.63 (d, J=8 Hz, 2H). MS (ion spray m/z 428 (M+H)+.

Reference Example 26b

By employing essentially the same procedure as used in reference example 26a, except using the product from reference example 29a, there is prepared 2-[4-(2-[N-t-Butoxycarbonyl-amino]-1,1-dimethyl-ethyl)-phenyl]-furan. $^1$H NMR (CDCl$_3$) d 1.31 (s, 6H), 1.39 (s, 9H), 3.31 (bd, J=6 Hz, 2H), 6.45 (dd, J=2, 1 Hz, 1H), 6.61 (d, J=2 Hz, 1H), 7.35 (d, J=8 Hz, 2H), 7.44 (d, J=1 Hz, 1H), 7.62 (d, J=8 Hz, 2H). MS (ion spray) m/z 316 (M+H)+.

Reference Example 26c

By employing essentially the same procedure as used in reference example 26a, except using the product from reference example 29b, there is prepared 2-[4-(1-[N-t-Butoxycarbonylamino]-cyclopentyl)-phenyl]-Furan. $^1$H NMR (CDCl$_3$) d 1.40 (s, 9H), 1.65–2.03 (m, 8H), 3.27 (d, J=6 Hz, 2H), 4.25 (bs, 1H), 6.46 (dd, J=3, 1 Hz, 1H), 6.63 (d, J=3 Hz, 1H), 7.30 (d, J=8 Hz, 2H), 7.47 (d, J=1 Hz, 1), 7.63 (d, J=8 Hz, 2H). MS (EI) m/z 341 (M)+.

Reference Example 27

4-(3-cyano-phenyl)-Benzyl-(t-Butyldimethylsilyl) Ether

To a cooled (−78° C.) solution of 4-bromo-benzyl-(t-butyldimethylsilyl)-ether (2.73 g, 9 mmol) (reference example 10) in THF (40 mL) was added, dropwise, n-buLi (4.4 mL, 2.5M in hexanes). On complete addition, the resulting solution was stirred for 10 min then ZnCl$_2$ (10 mL, 0.5M in THF) was added. The cold bath was removed and stirring continued for 10 min. To this solution was added a solution comprised of 3-bromo-benzonitrile (1.82 g, 10 mmol) (Aldrich), (Ph$_3$P)$_4$Pd (410 mg, 0.35 mmol) in THF (5 mL). The resulting mixture was heated to 65° C. and stirred at this temperature for 20 min. The reaction mixture was allowed to cool to room temperature then diluted with ether, washed, sequentially, with sat. ammonium chloride solution and brine, dried over MgSO$_4$ and concentrated. The residue was purified by flash chromatography (eluting with 5% EtOAc in hexanes) to give 2.0 g of the title compound. $^1$H NMR (CDCl$_3$) d 0.15 (s, 6H), 1.00 (s, 9H), 4.80 (s, 2H), 7.43 (d, J=8 Hz, 2H), 7.45–7.65 (m, 4H), 7.80 (m, 1H), 7.85 (bs, 1). MS (ion spray) m/z 324 (M+H)+.

Reference Example 28a 4-(2-[N-t-Butoxycarbonyl-amino]-1,1-dimethyl-ethyl)-Benzoic Acid To a solution of 2-[4-(2-[N-t-Butyloxy-carbonyl-amino]-1,1-dimethyl-ethyl)-phenyl]-furan (2.5 g, 7.9 mmol) (reference example 26b) in CCl$_4$/CH$_3$CN (100 mL, 1:1) was added, sequentially, water (75 mL) and NaIO$_4$, (7.7 g, 36 mmol). The resulting mixture was stirred vigorously and cooled to 10° C. RuCl$_3$;(H$_2$O) (20 mg, 0.1 mmol) was added and stirring continued for 3 hr as the temperature rose to 22° C. The reaction mixture was then diluted with ethyl acetate, washed with water and brine, dried over MgSO$_4$ and concentrated. The residue was passed through a short plug of silica (eluting with 60% EtOAc in hexanes) to give 1.84 g of the title compound as a tan solid. $^1$H NMR (CDCl$_3$) d 1.30 (s, 6H), 1.38 (s, 9H), 3.26 (bs, 1H), 3.33 (d, J=6 Hz, 2H), 7.44 (d, J=8 Hz, 2H), 8.05 (d, J=8 Hz, 2H).

Reference Example 28b

By employing essentially the same procedure as used in reference example 18a, except using the product from reference example 26c, there is prepared 4-(1-[N-t-Butoxycarbonyl-amino]-cyclopentyl)-Benzoic Acid. $^1$H NMR (DMSO) d 1.26 (s, 9H), 1.57 (m, 2H), 1.71 (m, 4H), 1.95 (m, 2H), 3.08 (d, J=6 Hz, 2H), 6.60 (bt, J=6 Hz, 1H), 7.33 (d, J=8 Hz, 2H), 7.82 (d, J=8 Hz, 2H). MS (ion spray) m/z 320 (M+H)$^+$.

Reference Example 29a 2,2-Dimethyl-(4-[Furan-2-yl]-Phenyl)-Acetonitrile

To a cooled (0° C.) mixture of TMEDA (11.4 mL, 76 mmol) and THF (75 mL) was added furan (5.7 mL, 78 mmol) followed by n-BuLi (15 mL, 2.5M in hexanes). The resulting solution was stirred for 30 min then ZnCl$_2$ added (60 mL, 0.5M in THF). To this solution was added a solution comprised of (4-bromo-phenyl)-2,2-dimethyl-acetonitrile (4.48 g, 20 mmol) (reference example 30a) and (Ph$_3$P)$_4$Pd (460 mg, 0.4 mmol) in THF (10 mL). The resulting mixture was warmed to 50° C. and stirred at this temperature for 2.5 hr. The reaction mixture was allowed to cool to room temperature, diluted with ether, then washed, sequentially, with aqueous hydrochloric acid (2M) and brine, then dried over MgSO$_4$ and concentrated. The residue was purified by flash chromatography (eluting with 10% ethyl acetate in hexanes) to give 3.9 g of the title compound as an oil. $^1$H NMR (CDCl$_3$) d 1.74 (s, 6H), 6.47 (dd, J=2, 1 Hz, 1H), 6.66 (d, J=2 Hz, 1H), 7.47 (m, 3H), 7.68 (m, 2H), MS (EI) m/z 211 (M)$^+$.

Reference Example 29b

By employing essentially the same procedure as used in reference example 19a, except using the product from reference example 30b, there is prepared 2-[4-(1-cyano-cyclopentyl)-phenyl]-Furan. $^1$H NMR (CDCl$_3$) d 1.85–2.13 (m, 6H), 2.45 (m, 2H), 6.47 (dd, J=3, 1 Hz, 1H), 6.65 (d, J=3 Hz, 1H), 7.44 (m, 3H), 7.66 (d, J=8 Hz, 2H). MS (EI) m/z 237 (M)$^+$.

Reference Example 30a (4-bromo-phenyl)-2,2-dimethyl-acetonitrile

To a cooled (0° C.) solution of 4-bromo-phenyl-acetonitrile (7.0 g, 35.7 mmol) in THF (70 mL) was added methyl iodide (4.9 mL, 78.6 mmol) followed by KOBu-t (79 mL, 1M in THF). On complete addition, the cold bath was removed and stirring continued for a further 1 hr. The reaction mixture was then diluted with ether, washed sequentially with water and brine, dried over MgSO$_4$ and concentrated. The residue was purified by flash chromatography (eluting with 10% ethyl acetate in hexanes) to give 7.49 g of the title compound as an oil. $^1$H NMR (CDCl$_3$) d 1.70 (s, 6H), 7.34 (d, J=8 Hz, 2H), 7.50 (d, J=8 Hz, 2H). MS (EI) m/z 223, 225 Br pattern (M)$^+$

Reference Example 30b

By employing essentially the same procedure as used in reference example 30a, except using 1,4-diiodobutane (Aldrich), there is prepared 1-[4-bromo-phenyl]-1-cyano-cyclopentane. $^1$H NMR (CDCl$_3$) d 1.82–2.1 (m, 6H), 2.45 (m, 2H), 7.3 (m, 2H), 7.49 (m, 2H). MS (EI) m/z 249/251 Br pattern (M)$^+$.

Reference Example 31

4-(3-N-t-butoxycarbonylamino-propyl)-benzoic Acid

To a solution of 4-(3-N-t-butoxycarbonylamino-propyl)-benzoic acid ethyl ester (1.4 g, 4.6 mmol) (reference example 32) in 1:1 THF-methanol (15 mL) was added NaOH (10N) (4.6 mL, 46 mmol). The resulting solution was stirred for 16 hrs then cooled to 0°–5° C. and adjusted to pH 3 with cold HCl (2N, 0° C.). The precipitated solid was filtered off, washed with a small volume of water, azeotroped 3× with toluene then dried under high vacuum to give 1.02 g of title compound as a white solid. $^1$H NMR (DMSO) δ1.38 (s, 9H), 1.68 (m, J=7 Hz, 2H), 2.63 (t, J=8 Hz, 2H), 2.93 (q, J=7 Hz, 2H), 6.88 (bt, 1H), 7.32 (d, J=8 Hz, 2H), 7.86 (d, J=8 Hz, 2H), 12.79 (s, 1H). MS (EI) m/z 280 (M+H)$^+$.

Reference Example 32

4-(3-N-t-butoxycarbonylamino-propyl)-benzoic acid ethyl ester

To a solution of 4-(3-N-t-butoxycarbonylamino-propyn)-benzoic acid ethyl ester (1.73 g, 5.7 mmol) (reference example 33) in ETOH (12 mL), under argon, was added 10% palladium on carbon (260 mg). The resulting mixture was heated to 60° C. and stirred under H$_2$ for 6 hrs then cooled to 20° C. The mixture was filtered through a celite pad to remove the catalyst, using CH$_2$Cl$_2$ as a wash. The filtrate was conc and the residue purified by flash chromatography (eluting with 40% ether in hexanes) to give 1.4 g of title compound as a white crystalline solid. $^1$H NMR (CDCl$_3$) δ1.39 (t, J=7 Hz, 3H), 1.44 (s, 9H), 1.82 (m, J=7 Hz, 2H), 2.69 (t, J=8 Hz, 2H), 3.15 (q, J=7 Hz, 2H), 4.36 (q, J=7 Hz, 2H), 4.62 (bs, 1H), 7.24 (d, J=8 Hz, 2H), 7.96 (d, J=8 Hz, 2H). MS (EI) m/z 308 (M+H)$^+$.

Reference Example 33

4-(3-N-t-butoxycarbonylamino-propyn)-benzoic acid ethyl ester

Ethyl-4-iodobenzoate (2.76 g, 10 mmol), copper iodide 99.999% (76 mg, 0.4 mmol), tetrakis(triphenylphosphine)palladium(0) (462 mg, 0.4 mmol), piperidine (1.28 mL, 13 mmol) and a solution of propargylamine (686 μL, 10 mmol) are combined in THF (10 mL). The resulting mixture is stirred for 1 hr then di-t-butyldicarbonate (4.36 g, 20 mmol) is added and stirring continued for 15 min. A further portion of di-t-butyldicarbonate (436 mg, 2 mmol) is added to the mixture and stirred for 30 min. The mixture is then diluted with ethyl acetate, washed with water and then brine, dried over MgSO$_4$ and concentrated. The residue is purified by flash chromatography (eluting with 20% ethyl acetate in hexanes) to give 1.73 g of the title compound as a yellow crystalline solid. $^1$H NMR (CDCl$_3$) δ1.39 (t, J=7 Hz, 3H), 1.47 (s, 9H), 4.18 (bd, J=5 Hz, 2H), 4.37 (q, J=7 Hz, 2H), 4.82 (bs, 1H), 7.46 (d, J=8 Hz, 2H), 7.98 (d, J=8 Hz, 2H). MS (EI) m/z 304 (M+H)$^+$.

Reference Example 34a

N-[Biphenyl-4-yl-methyl]-2-(5-cyano-2,3-dihydro-benzofuranyl)acetamide

To a cooled (0° C.) suspension of 3-(carboxy-methyl)-5-cyano-2,3-dihydrobenzofuran (300 mg, 1.5 mmol, reference example 9) in CH$_2$Cl$_2$ (4 mL) is added triethylamine (210 mL, 1.5 mmol) followed by isopropyl chloroformate (1.65 mL, 1 M in CH$_2$Cl$_2$). The resulting solution is stirred for 20 min then a further portion of triethylamine is added (455 mL, 3.3 mmol) followed by 4-aminomethyl biphenyl hydrochloride (330 mg, 1.5 mmol). The cold bath is removed and stirring continued for 5 h. The reaction mixture is then diluted with CH$_2$Cl$_2$, washed with water and brine, dried over MgSO$_4$ and concentrated. The residue was triturated with ether and the solid filtered to give 400 mg of the title compound. $^1$H NMR (CDCl$_3$) δ2.55 (dd, J=16, 8 Hz, 1H), 2.65 (dd, J=16, 6 Hz, 1H), 4.06 (m, 1H), 4.42 (dd, J=8, 7 Hz, 1H), 4.49 (dd, J=15, 6 Hz, 1H), 4.55 (dd, J=15, 6 Hz, 1H), 4.88 (t, J=8 Hz, 1H), 6.83 (m, 1H), 7.38 (m, 3H), 7.37 (m, 1H), 7.45 (m, 4H), 7.61 (m, 4H). MS (EI) m/z 368 (M+).

Reference Example 34b

Using essentially the same procedure described in reference example 34a, except using 4-amino-biphenyl instead of 4-aminomethyl-biphenyl there is prepared: N-[Biphenyl-4-yl]-2-(5-cyano-2,3-dihydro-benzofuranyl)acetamide. $^1$H NMR (CDCl$_3$) δ2.72 (dd, J=16, 8 Hz, 1H), 2.87 (dd, J=16, 7 Hz, 1H), 4.1 (m, 1H), 4.46 (dd, J=8, 7 Hz, 1H), 4.92 (t, J=8 Hz, 1H), 6.87 (d, J=8 Hz, 1H), 7.1–7.68 (m, 11H). MS (FAB) m/z 355 (M+H).

Reference Example 34c

Using essentially the same procedure described in reference example 34a, except using 1-benzyl piperazine instead of 4-aminomethyl-biphenyl there is prepared: 3-[2-(4-Benzyl-piperazin-1-yl)-2-oxo-ethyl]-5-cyano-2,3-dihydro-benzofuran. $^1$H NMR (CDCl$_3$) δ2.46 (m, 2H), 2.60 (dd, J=15, 8 Hz, 1H), 2.84 (dd, J=15, 5, Hz, 1H), 3.44 (m, 2H), 3.55 (s, 2H), 3.67 (m, 2H), 4.0 (m, 1H), 4.32 (dd, J=9, 5 Hz, 1H), 4.94 (t, J=9 Hz, 1H), 6.81 (d, J=8 Hz, 1H), 7.31 (m, 5H), 7.45 (m, 2H). MS (EI) m/z 361 (M+).

Reference Example 34d

Using essentially the same procedure described in reference example 34a, except using 4-benzyl piperidine instead of 4-aminomethyl-biphenyl there is prepared: 3-[2-(4-Benzyl-piperidin-1-yl)-2-oxo-ethyl]-5-cyano-2,3-dihydro-benzofuran. $^1$H NMR (CDCl$_3$) δ1.15 (m, 2H), 1.75 (m, 3H), 2.83 (m, 1H), 2.96 (m, 1H), 3.74 (bd, J=14 Hz, 1H), 3.97 (m, 1H), 4.31 (m, 1H), 4.61 (bd, J=14 Hz, 1H), 4.95 (dt, J=9, 1 Hz, 1H), 6.82 (d, J=8 Hz, 1H), 7.1–7.35 (m, 6H), 7.49 (m, 2H). MS (EI) m/z 360 (M+)

Reference Example 35

3-(3-Biphenyl-4-ylmethyl-ureido-methyl)-5-cyano-2,3-dihydrobenzofuran

To a suspension of 3-(carboxy-methyl)-5-cyano-2,3-dihydrobenzofuran (200 mg, 1.0 mmol, reference example 9) in CH$_2$Cl$_2$ (4 mL) is added triethylamine (140 mL, 1 mmol) followed by diphenylphosphoryl azide (236 mL, 1.1 mmol). The resulting solution is stirred for 20 min. then diluted with ether, washed with water and brine, dried over MgSO$_4$ and concentrated under vacuum at less than 30° C. to give 300 mg of a tan solid. This solid is dissolved in toluene (10 mL) then added to a boiling toluene solution (5 mL) over 5 min. On complete addition, the mixture is stirred a further 5 min then cooled to room temperature. To this solution is added 4-aminomethyl-biphenyl hydrochloride (220 mg, 1 mmol) followed by triethyl amine (160 mL, 1.15 mmol). The resulting mixture was stirred for 90 min then diluted with CH$_2$Cl$_2$, washed with 1M HCl then brine dried over MgSO$_4$ and concentrated to give 300 mg of a tan solid product. $^1$H NMR (DMSO) δ3.35 (m, 2H), 3.67 (m, 1H), 4.27 (d, J=5 Hz, 2H), 4.46 (m, 1H), 4.70 (t, J=9 Hz, 1H), 6.24 (t, J=5 Hz, 1H), 6.50 (bt, 1H), 6.98 (d, J=8 Hz, 1H), 7.3 (m, 4H), 7.47 (m, 2H), 7.64 (m, 5H),. MS (EI) m/z 383.

Reference Example 36

3-{2-[4-(1,1-Dimethylpropyl)benzenesulfonylamino] ethyl}-5-tert-butoxycarbonylcarbamimidoyl-2,3-dihydrobenzofuran To a solution of 3-(2-aminoethyl)-5-tert-butoxycarbonylcarbamimidoyl-2,3-dihydrobenzofuran [0.152 g, 0.500 mmol] in DMF [10 ml] and pyridine [5 ml] was added 4-tert-amylbenzene-sulfonyl chloride [0.130 g, 0.525 mmol]. After 18 hours the reaction mixture was concentrated and the resulting residue chromatographed (2:1, then 1:1 hexane:ethyl acetate) to give 44 mg of the product as a yellow oil. $^1$H NMR (CDCl$_3$): δ0.660 (3H, t, J=7 Hz), 1.30 (6H, s), 1.53 (9H, s), 1.66 (2H, q, J=7 Hz), 1.80 (1H, m), 1.90 (1H, m), 2.92–3.13 (2H, m), 3.56 (1H, m), 4.26 (1H, m), 4.66 (1H, t, J=7 Hz), 6.77 (1H, d, J=7 Hz), 7.45 (2H, d, J=8 Hz), 7.74 (1H, d, J=7 Hz), 7.80 (2H, d, J=8 Hz), 7.83 (1H, s). MS (ion spray) m/z=516 (M+H)$^+$, 416 (M+H-BOC)$^+$.

Reference Example 37

Using essentially the same procedure used to prepare reference example 36 except using 7-Chlorobenzo[1,2,5] oxadiazole-5-sulfonyl chloride there is prepared 3-[2-(7-Chlorobenzo-[1,2,5]oxadiazole-5-sulfonylamino)ethyl]-5-tert-butoxycarbonylcarbamididoyl-2,3-dihydrobenzo-furan. $^1$H NMR (CDCl$_3$): δ1.53 (9H, s), 1.82–2.00 (2H, m), 3.13 (2H, m), 3.58 (1H, m), 4.30 (1H, m), 4.70 (1H, t, J=9 Hz), 6.77 (1H, d, J=9 Hz), 7.58 (1H, d, J=7 Hz), 7.66 (1H, d, J=9 Hz), 7.80 (1H, s), 8.01 (1H, d, J=7 Hz). MS (ion spray) m/z=522 (M+H)$^+$, 466 (M+H-butyl)$^+$, 422 (M+H-BOC)$^+$.

Reference Example 38

A mixture of 4-(2-methoxy-pyridin-5-yl)-benzoic acid (1 mmol, 229 mg, reference example 17g) and pyridinium hydrochloride (4 g, 35 mmol) is heated to 165° C. and stirred at this temperature for 5 min. The mixture is then allowed to cool and then water is added. The resulting mixture is filtered under vacuum. The solid is washed with water, dried under high vacuum then used without further purification.

The molecules described herein inhibit blood coagulation by virtue of their ability to inhibit the penultimate enzyme in the coagulation cascade, Factor Xa (rather than thrombin). Both free Factor Xa and Factor Xa assembled in the prothrombinase complex (Factor Xa, Factor Va, calcium and phospholipid) are inhibited. Factor Xa inhibition is obtained by direct complex formation between the inhibitor and the enzyme, and is therefore independent of the plasma co-factor antithrombin III. Effective Factor Xa inhibition is achieved by administering the compounds either by oral administration, by continuous intravenous infusion, by bolus intravenous administration or by any other parenteral route such that it achieves the desired effect of preventing the Factor Xa induced formation of thrombin from prothrombin.

Anticoagulant therapy is indicated for the treatment and prophylaxis of a variety of physiological thrombotic conditions of both the venous and arterial vasculature. In the arterial system, abnormal thrombus formation is primarily associated with arteries of the coronary, cerebral and peripheral vasculature. The diseases associated with thrombotic occlusion of these vessels principally include acute myocardial infarction (AMI), unstable angina, thromboembolism, acute vessel closure associated with thrombolytic therapy and percutaneous transluminal coronary angioplasty (PTCA), transient ischemic attacks, stroke, intermittent claudication and bypass grafting (CABG) of the coronary or peripheral arteries. Chronic anticoagulant therapy may also be beneficial in preventing the vessel luminal narrowing (restenosis) that often occurs following PTCA and CABG, and in the maintenance of vascular access patency in long-term hemodialysis patients. With respect to the venous vasculature, pathologic thrombus formation frequently occurs in the veins of the lower extremities following abdominal, knee and hip surgery (deep vein thrombosis, DVT). DVT further predisposes the patient to a higher risk of pulmonary thromboembolism. A systemic, disseminated intravascular coagulopathy (DIC) commonly occurs in both vascular systems during septic shock, certain viral infections and cancer. This condition is characterized by a rapid consumption of coagulation factors and their plasma inhibitors resulting in the formation of life-threatening thrombin throughout the microvasculature of several organ systems. The indications discussed above include some, but not all, of the possible clinical situations where anticoagulant therapy is warranted. Those experienced in this field are well aware of the circumstances requiring either acute or chronic prophylactic anticoagulant therapy.

These compounds may be used alone or in combination with other diagnostic, anticoagulant, antiplatelet or fibrinolytic agents. For example adjunctive administration of inhibitors of the activity of Factor Xa with standard heparin, low molecular weight heparin(s), synthetic pentasaccharides, direct thrombin inhibitors (e.g. hirudin, Agratroban (Novastan®), aspirin, fibrinogen receptor antagonists, statins/fibrates streptokinase, urokinase and/or tissue plasminogen activator. The compounds described herein may be administered to treat thrombotic complications in a variety of animals such as primates including humans. Inhibition of factor Xa is useful not only in the anticoagulant therapy of individuals having thrombotic conditions but is useful whenever inhibition of blood coagulation is required such as to prevent coagulation of stored whole blood and to prevent coagulation in other biological samples for testing or storage. Thus, any inhibitor of Factor Xa activity can be added to or contacted with any medium containing or suspected of containing Factor Xa and in which it is desired that blood coagulation be inhibited.

In addition to their use in anticoagulant therapy, Factor Xa inhibitors may find utility in the treatment or prevention of other diseases in which the generation of thrombin has been implicated as playing a physiologic role. For example, thrombin has been proposed to contribute to the morbidity and mortality of such chronic and degenerative diseases as arthritis, cancer, atherosclerosis and Alzheimer's disease by virtue of its ability to regulate many different cell types through specific cleavage and activation of a cell surface thrombin receptor, mitogenic effects, diverse cellular functions such as cell proliferation, for example, abnormal proliferation of vascular cells resulting in restenosis or angiogenesis, release of PDGF and DNA syntheses. Inhibition of Factor Xa will effectively block thrombin generation and therefore neutralize any physiologic effects of thrombin on various cell types.

Accordingly, the invention provides a method of inhibiting Factor Xa comprising contacting a Factor Xa inhibitory amount of a compound of formula I with a composition containing Factor Xa.

According to a further feature of the invention there is provided a method of inhibiting the formation of thrombin comprising contacting Factor Xa inhibitory amount of a compound of formula I with a composition containing Factor Xa.

According to a further feature of the invention there is provided a method for the treatment of a human or animal patient suffering from, or subject to, conditions which can be ameliorated by the administration of an inhibitor of Factor Xa, for example conditions as hereinbefore described, which comprises the administration to the patient of an effective amount of compound of formula I or a composition containing a compound of formula I. "Effective amount" is meant to describe an amount of compound of the present invention effective in inhibiting Factor Xa and thus producing the desired therapeutic effect.

The present invention also includes within its scope pharmaceutical formulations which comprise at least one of the compounds of Formula I in association with a pharmaceutically acceptable carrier or coating.

In practice compounds of the present invention may generally be administered parenterally, intravenously, subcutaneously intramuscularly, colonically, nasally, intraperitoneally, rectally or orally.

The products according to the invention may be presented in forms permitting administration by the most suitable route and the invention also relates to pharmaceutical compositions containing at least one product according to the invention which are suitable for use in human or veterinary medicine. These compositions may be prepared according to the customary methods, using one or more pharmaceutically acceptable adjuvants or excipients. The adjuvants comprise, inter alia, diluents, sterile aqueous media and the various non-toxic organic solvents. The compositions may be presented in the form of tablets, pills, granules, powders, aqueous solutions or suspensions, injectable solutions, elixirs or syrups, and can contain one or more agents chosen from the group comprising sweeteners, flavorings, colorings, or stabilizers in order to obtain pharmaceutically acceptable preparations.

The choice of vehicle and the content of active substance in the vehicle are generally determined in accordance with the solubility and chemical properties of the product, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulfate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol and chloroform or mixtures thereof may also be used.

For parenteral administration, emulsions, suspensions or solutions of the products according to the invention in vegetable oil, for example sesame oil, groundnut oil or olive oil, or aqueous-organic solutions such as water and propylene glycol, injectable organic esters such as ethyl oleate, as well as sterile aqueous solutions of the pharmaceutically acceptable salts, are used. The solutions of the salts of the products according to the invention are especially useful for administration by intramuscular or subcutaneous injection. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride and that they are sterilized by heating, irradiation or microfiltration.

Suitable compositions containing the compounds of the invention may be prepared by conventional means. For example, compounds of the invention may be dissolved or suspended in a suitable carrier for use in a nebulizer or a suspension or solution aerosol, or may be absorbed or adsorbed onto a suitable solid carrier for use in a dry powder inhaler.

Solid compositions for rectal administration include suppositories formulated in accordance with known methods and containing at least one compound of formula I.

The percentage of active ingredient in the compositions of the invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration and the duration of the treatment, and the condition of the patient. In the adult, the doses are generally from about 0.01 to about 100, preferably about 0.01 to about 10, mg/kg body weight per day by inhalation, from about 0.01 to about 100, preferably 0.1 to 70, more especially 0.5 to 10, mg/kg body weight per day by oral administration, and from about 0.01 to about 50, preferably 0.01 to 10, mg/kg body weight per day by intravenous administration. In each particular case, the doses will be determined in accordance with the factors distinctive to the subject to be treated, such as age, weight, general state of health and other characteristics which can influence the efficacy of the medicinal product.

The products according to the invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. It goes without saying that, for other patients, it will be necessary to prescribe not more than one or two doses per day.

The compounds of the present invention may also be formulated for use in conjunction with other therapeutic agents such as agents or in connection with the application of therapeutic techniques to address pharmacological conditions which may be ameliorated through the application of a compound of formula I, as described herein.

The compounds of the present invention may be used in combination with any anticoagulant, antiplatelet, antithrombotic or fibrinolytic agent. Often patients are concurrently treated prior, during and after interventional procedures with agents of these classes either in order to safely perform the interventional procedure or to prevent deleterious effects of thrombus formation. Some examples of classes of agents known to be anticoagulant, antiplatelet, antithrombotic or profibrinolytic agents include any formulation of heparin, low molecular weight heparins, pentasaccharides, fibrinogen receptor antagonists, thrombin inhibitors, Factor Xa inhibitors, or Factor VIIa inhibitors.

The compounds of the present invention may be used in combination with any antihypertensive agent or cholesterol or lipid regulating agent, or concurrently in the treatment of restenosis, atherosclerosis or high blood pressure. Some examples of agents that are useful in combination with a compound according to the invention in the treatment of high blood pressure include compounds of the following classes; beta-blockers, ACE inhibitors, calcium channel antagonists and alpha-receptor antagonists. Some examples of agents that are useful in combination with a compound according to the invention in the treatment of elevated cholesterol levels or disregulated lipid levels include compounds known to be HMGCoA reductase inhibitors, compounds of the fibrate class.

It is understood that the present invention includes combinations of compounds of the present invention with one or more of the aforementioned therapeutic class agents.

Compounds within the scope of the present invention exhibit marked pharmacological activities according to tests described in the literature and below which tests results are believed to correlate to pharmacological activity in humans and other mammals.

Enzyme Assays

The ability of the compounds in the present invention to act as inhibitors of Factor Xa, thrombin, trypsin, tissue-plasminogen activator (t-PA), urokinase-plasminogen activator (u-PA), plasmin and activated protein C is evaluated by determining the concentration of inhibitor which resulted in a 50% loss in enzyme activity (IC50) using purified enzymes.

All enzyme assays are carried out at room temperature in 96-well microtiter plates using a final enzyme concentration of 1 nM. The concentrations of Factor Xa and thrombin are determined by active site titration and the concentrations of all other enzymes are based on the protein concentration supplied by the manufacturer. Compounds according to the invention are dissolved in DMSO, diluted with their respective buffers and assayed at a maximal final DMSO concentration of 1.25%. Compound dilutions are added to wells containing buffer and enzyme and pre-equilibrated for between 5 and 30 minutes. The enzyme reactions are initiated by the addition of substrate and the color developed from the hydrolysis of the peptide-p-nitroanilide substrates is monitored continuously for 5 minutes at 405 nm on a Vmax microplate reader (Molecular Devices). Under these conditions, less than 10% of the substrate is utilized in all assays. The initial velocities measured are used to calculate the amount of inhibitor which resulted in a 50% reduction of the control velocity ($IC_{50}$). The apparent Ki values are then determined according to the Cheng-Prusoff equation (IC50= Ki [1+[S]/Km]) assuming competitive inhibition kinetics.

An additional in vitro assay may be used to evaluate the potency of compounds according to the invention in normal human plasma. The activated partial thromboplastin time is a plasma-based clotting assay that relies on the in situ generation of Factor Xa, its assembly into the prothrombinase complex and the subsequent generation of thrombin and fibrin which ultimately yields the formation of a clot as the assay endpoint. This assay is currently used clinically to monitor the ex vivo effects of the commonly used anticoagulant drug heparin as well as direct acting antithrombin agents undergoing clinical evaluation. Therefore, activity in this in vitro assay is considered as a surrogate marker for in vivo anticoagulant activity.

Human Plasma Based Clotting Assay

Activated partial thromboplastin clotting times are determined in duplicate on a MLA Electra 800 instrument. A volume of 100 µl of citrated normal human pooled plasma (George King Biomedical) is added to a cuvette containing 100 µl of a compound according to the invention in Tris/NaCl buffer (pH 7.5) and placed in the instrument. Following a 3 minute warming period the instrument automatically adds 100 µl of activated cephaloplastin reagent (Actin, Dade) followed by 100 µl of 0.035 M $CaCl_2$ to initiate the clotting reaction. Clot formation is determined spectrophotometrically and measured in seconds. Compound potency is quantitated as the concentration required to double a control clotting time measured with human plasma in the absence of the compound according to the invention.

Compounds according to the invention may also be evaluated for their in vivo antithrombotic efficacy in two well established animal experimental models of acute vascular thrombosis. A rabbit model of jugular vein thrombosis and a rat model of carotid artery thrombosis are used to demonstrate the antithrombotic activity of these compounds in distinct animal model paradigms of human venous thrombosis and arterial thrombosis, respectively.

Experimental in vivo Rabbit Venous Thrombosis Model

This is a well characterized model of fibrin rich venous thrombosis that is validated in the literature and shown to be sensitive to several anticoagulant drugs including heparin (Antithrombotic Effect of Recombinant Truncated Tissue Factor Pathway Inhibitor (TFPI 1-161) in Experimental Venous Thrombosis-a Comparison with Low Molecular Weight Heparin, J. Hoist, B. Lindblad, D. Bergqvist, O. Nordfang, P. B. Ostergaard, J. G. L. Petersen, G. Nielsen and U. Hedner. Thrombosis and Haemostasis, 71, 214–219 (1994). The purpose of utilizing this model is to evaluate the ability of compounds to prevent the formation of venous thrombi (clots) in vivo generated at a site of injury and partial stasis in the jugular vein.

Male and female New Zealand white rabbits weighing 1.5–2 kg are anesthetized with 35 mg/kg of ketamine and 5 mg/kg xylazine in a volume of 1 mL/kg (i.m.). The right jugular vein is cannulated for infusion of anesthetic (ketamine/xylazine 17/2.5 mg/kg/hr at a rate of approximately 0.5 mL/hr) and administration of test substances. The right carotid artery is cannulated for recording arterial blood pressure and collecting blood samples. Body temperature is maintained at 39° C. with a GAYMAR T-PUMP. The left external jugular vein is isolated and all side branches along an exposed 2–3 cm of vessel are tied off. The internal jugular vein is cannulated, just above the bifurcation of the common jugular, and the tip of the cannula is advanced just proximal to the common jugular vein. A 1 cm segment of the vein is isolated with non-traumatic vascular clamps and a relative stenosis is formed by tying a ligature around the vein with an 18 G needle just below the distal most clamp. This creates a region of reduced flow and partial stasis at the injury site. The isolated segment is gently rinsed with saline 2–3 times via the cannula in the internal jugular. Thereafter the isolated segment is filled with 0.5 mL of 0.5% polyoxyethylene ether (W-1) for 5 minutes. W-1 is a detergent which disrupts the endothelial cell lining of the segment, thus providing a thrombogenic surface for initiating clot formation. After 5 minutes the W-1 is withdrawn from the segment, and the segment is again gently rinsed with saline 2–3 times. The vascular clamps are then removed, restoring blood flow through this portion of the vessel. Clot formation is allowed to form and grow for 30 minutes after which the vein is cut just below the stenotic ligature and inspected for blood flow (the absence of blood flow is recorded as complete occlusion). The entire isolated segment of vein is then ligated and the formed clot is removed and weighed (wet weight). The effect of test agents on final clot weights is used as the primary end point. Animals are maintained for an additional thirty minutes to obtain a final pharmacodynamic measure of anticoagulation. Drug administration is initiated 15 minutes prior to vascular injury with W-1 and continued through the period of clot formation and maturation. Three blood samples (3 mL ea.) are obtained for evaluation of hemostatic parameters: one just prior to administration of W-1; a second 30 minutes after removal of the vascular clamps and a third at the termination of the experiment. Antithrombotic efficacy is expressed as a reduction in the final clot weight in preparations treated with a compound according to the invention relative to vehicle treated control animals.

Experimental in vivo Rat Arterial Thrombosis Model

The antithrombotic efficacy of Factor Xa inhibitors against platelet-rich arterial thrombosis may be evaluated using a well characterized rat carotid artery $FeCl_2$-induced thrombosis model (Superior Activity of a Thromboxane Receptor Antagonist as Compared with Aspirin in Rat Models of Arterial and Venous Thrombosis, W. A. Schumacher, C. L. Heran, T. E. Steinbacher, S. Youssef and M. L. Ogletree. Journal of Cardiovascular Pharmacology, 22, 526–533 (1993); Rat Model of Arterial Thrombosis Induced by Ferric Chloride, K. D. Kurtz, B. W. Main, and G. E. Sandusky. Thrombosis Research, 60, 269–280 (1990); The Effect of Thrombin Inhibition in a Rat Arterial Thrombosis Model, R. J. Broersma, L. W. Kutcher and E. F. Heminger. Thrombosis Research 64, 405–412 (1991). This model is widely used to evaluate the antithrombotic potential of a variety of agents including heparin and the direct acting thrombin inhibitors.

Sprague Dawley rats weighing 375–450 g are anesthetized with sodium pentobarbital (50 mg/kg i.p.). Upon reaching an acceptable level of anesthesia, the ventral surface of the neck is shaved and prepared for aseptic surgery. Electrocardiogram electrodes are connected and lead 11 is monitored throughout the experiment. The right femoral vein and artery are cannulated with PE-50 tubing for administration of a compound according to the invention and for obtaining blood samples and monitoring blood pressure, respectively. A midline incision is made in the ventral surface of the neck. The trachea is exposed and intubated with PE-240 tubing to ensure airway patency. The right carotid artery is isolated and two 4-0 silk sutures are placed around the vessel to facilitate instrumentation. An electromagnetic flow probe (0.95–1 mm lumen) is placed around the vessel to measure blood flow. Distal to the probe a 4×4 mm strip of parafilm is placed under the vessel to isolate it from the surrounding muscle bed. After baseline flow measurements are made, a 2×5 mm strip of filter paper previously saturated in 35% $FeCl_2$ is placed on top of the vessel downstream from the probe for ten minutes and then removed. The $FeCl_2$ is thought to diffuse into the underlying segment of artery and cause deendothelialization resulting in acute thrombus formation. Following application of the $FeCl_2$-soaked filter paper, blood pressure, carotid artery blood flow and heart rate are monitored for an observation period of 60 minutes. Following occlusion of the vessel (defined as the attainment of zero blood flow), or 60 minutes after filter paper application if patency is maintained, the artery is ligated proximal and distal to the area of injury and the vessel is excised. The thrombus is removed and weighed immediately and recorded as the primary end point of the study.

Following surgical instrumentation a control blood sample (B1) is drawn. All blood samples are collected from the arterial catheter and mixed with sodium citrate to prevent clotting. After each blood sample, the catheter is flushed with 0.5 mL of 0.9% saline. A compound according to the invention is administered intravenously (i.v.) starting 5 minutes prior to $FeCl_2$ application. The time between $FeCl_2$ application and the time at which carotid blood flow reached zero is recorded as time to occlusion (TTO). For vessels that did not occlude within 60 minutes, TTO is assigned a value of 60 minutes. Five minutes after application of $FeCl_2$, a second blood sample is drawn (B2). After 10 minutes of $FeCl_2$ exposure, the filter paper is removed from the vessel and the animal is monitored for the remainder of the experiment. Upon reaching zero blood flow blood a third blood sample is drawn (B3) and the clot is removed and weighed. Template bleeding time measurements are performed on the forelimb toe pads at the same time that blood samples are obtained. Coagulation profiles consisting of activated partial thromboplastin time (APTT) and prothrombin time (PT) are performed on all blood samples. In some instances a compound according to the invention may be administered orally. Rats are restrained manually using standard techniques and compounds are administered by intragastric gavage using a 18 gauge curved dosing needle (volume of 5 mL/kg). Fifteen minutes after intragastric dosing, the animal is anesthetized and instrumented as described previously. Experiments are then performed according to the protocol described above.

The present invention may be embodied in other specific forms without departing from the spirit or essential attributes thereof.

What is claimed is:

1. A compound of formula I:

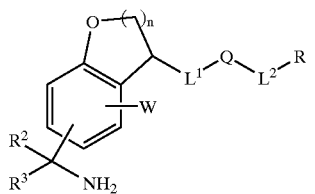

(I)

n=1 or 2

W is H or a ring system substituent.

R is hydrogen, cyano, cycloalkyl, cycloalkenyl, heterocyclyl, heterocyclenyl, fused arylcycloalkyl, fused heteroarylcycloalkyl, fused arylcycloalkenyl, fused heteroarylcycloalkenyl, fused arylheterocyclyl, fused heteroarylheterocyclyl, fused arylheterocyclenyl, fused heteroarylheterocyclenyl, aryl, fused cycloalkenylaryl, fused cycloalkylaryl, fused heterocyclylaryl, fused heterocyclenylaryl, heteroaryl, fused cycloalkylheteroaryl, fused cycloalkenylheteroaryl, fused heterocyclenylheteroaryl, or fused heterocyclylheteroaryl, $R^2$ and $R^3$ are each hydrogen, or, taken together are $=NR^4$;

$R^4$ is hydrogen, $R^5O_2C-$, $R^5O-$, $HO-$, cyano, $R^5CO-$, $HCO-$, lower alkyl, nitro, or $R^6R^7N-$;

$R^5$ is alkyl, aryl, heteroaryl, aralkyl, or heteroaralkyl;

$R^6$ and $R^7$ are independently hydrogen or alkyl;

$L^1$ is alkylene, alkenylene or alkynylene;

$L^2$ is absent (i.e. a chemical bond), alkylene, alkenylene, alkynylene, alkylene-O—, alkenylene-O—, alkynylene-O—, alkylene-S—, alkenylene-S—, alkynylene-S—, alkylene-S-alkylene, alkenylene-S-alkylene, alkynylene-S-alkylene, alkylene-O-alkylene, alkenylene-O-alkylene, alkynylene-O-alkylene, alkylene-C(O)—, alkenylene-C(O)—, alkynylene-C(O)—, provided that when $L^2$ is absent, then R is not hydrogen, and Q is attached to R through a carbon atom thereof;

Q is $-NR^{8'}-$, $-O-$, $-C(O)-$, $-C(O)-O-$, $-O-C(O)-$, $-NR^{8'}OC(X^1)-$, $-C(X^1)NR^{8'}-$, $-NR^8C(X^1)O-$, $-OC(X^1)NR^8-$, $-NR^8C(X^1)NR^8-$, $-NR^8C(X^1)NR^8-$, $-S(O)_m-$, $-NR^8SO_2-$ or $-SO_2NR^8-$, provided that a nitrogen atom or oxygen atom of Q is not directly bonded to a carbon atom of $L^1$ or $L^2$ having a double bond or triple bond;

$X^1$ is O or S;

$R^{8'}$ is hydrogen, alkyl, aralkyl, heteroaralkyl, acyl, aroyl, heteroaroyl or alkoxycarbonyl;

$R^8$ is hydrogen, alkyl, aralkyl, heteroaralkyl, acyl, aroyl or heteroaroyl; and m is 0, 1 or 2, an oxide thereof, a pharmaceutically acceptable salt thereof, a solvate thereof, or prodrug thereof, provided that the compound of formula I wherein $R^2$ and $R^3$ are each hydrogen, $L^1$ is methylene, Q is $-C(O)NH-$, $L^2$ is $-CH(COOCH_3)CH_2-$ and R is phenyl is excluded.

2. The compound of claim 1 wherein R is aryl, heteroaryl or heterocyclyl.

3. The compound of claim 1 wherein R is substituted phenyl.

4. The compound of claim 1 wherein W is H, lower alkyl, alkoxy, F or Cl.

5. The compound of claim 1 wherein W is H.

6. The compound of claim 1 wherein $R^8$ is hydrogen.

7. The compound of claim 1 wherein $R^2$ and $R^3$ taken together are $=NR^4$.

8. The compound of claim 1 wherein $R^4$ is hydrogen.

9. The compound of claim 1 wherein $R^5$ is alkyl.

10. The compound of claim 9 wherein $R^5$ is methyl.

11. The compound of claim 1 wherein $R^6$ and $R^7$ are hydrogen.

12. The compound of claim 1 wherein $L^1$ is alkylene.

13. The compound of claim 1 wherein $L^1$ is ethylene.

14. The compound of claim 1 wherein $L^2$ is alkylene-C(O)— or alkylene-O—.

15. The compound of claim 1 wherein $L^2$ is absent or alkylene.

16. The compound of claim 14 wherein $L^2$ is absent.

17. The compound of claim 1 wherein $X^1$ is O.

18. The compound of claim 1 wherein Q is $-NR^8CO-$, $-CONR^8-$, $-NR^8SO_2-$ or $-SO_2NR^8-$.

19. The compound of claim 1 wherein O is $-NR^8CO-$.

20. The compound of claim 1 wherein $R^8$ and R8' are hydrogen.

21. The compound of claim 1 wherein n is 2.

22. A compound according to claim 1 which is selected from the group consisting of 5-(Pyridin-2-yl)-thiophene-2-carboxylic acid (2-[5-carbamimidoyl-2,3-dihydrobenzofuran-3-yl]ethyl)amide;

4-tert-Butyl-N-(2-[5-carbamimidoyl-2,3-dihydrobenzofuran-3-yl]ethyl)benzamide;

4-(2-Amino-1,1-dimethylethyl)-N-(2-[5-carbamimidoyl-2,3-dihydrobenzofuran-3-yl]ethyl)benzamide;

N-[2-(5-carbamimidoyl-2,3-dihydro-benzofuran-3-yl)-ethyl]-4-(3-amino-propyl)-benzamide;

N-[2-(5-carbamimidoyl-2,3-dihydro-benzofuran-3-yl)-ethyl]-2-(N-phenyl-amino)-benzamide;

N-[2-(5-carbamimidoyl-2,3-dihydro-benzofuran-3-yl)-ethyl]-2-(phenoxy)-benzamide;

N-[2-(5-carbamimidoyl-2,3-dihydro-benzofuran-3-yl)-ethyl]-4-(N,N-diethylamino)-benzamide;

N-[2-(5-carbamimidoyl-2,3-dihydro-benzofuran-3-yl)-ethyl]-4-(phenoxy)-benzamide;

N-[2-(5-carbamimidoyl-2,3-dihydro-benzofuran-3-yl)-ethyl]-2-methyl-3-phenyl-prop-2-enoic acid amide;

N-[2-(5-carbamimidoyl-2,3-dihydro-benzofuran-3-yl)-ethyl]-10-cyano-decanoic acid amide;

N-[2-(5-carbamimidoyl-2,3-dihydro-benzofuran-3-yl)-ethyl]-4-oxo-(4-methoxy-phenyl)-butyramide;

N-[2-(5-carbamimidoyl-2,3-dihydro-benzofuran-3-yl)-ethyl]-(1-methyl-pyrrole-2)-carboxamide;

N-[2-(5-carbamimidoyl-2,3-dihydro-benzofuran-3-yl)-ethyl]-(2,2-diphenyl)-propionamide;

N-[2-(5-carbamimidoyl-2,3-dihydro-benzofuran-3-yl)-ethyl]-(2-(4-chloro-phenoxy)-2-methyl-propionamide;
N-[2-(5-carbamimidoyl-2,3-dihydro-benzofuran-3-yl)-ethyl]-(2-[4-phenyl]-phenyl)-acetamide;
N-[2-(5-carbamimidoyl-2,3-dihydro-benzofuran-3-yl)-ethyl]-3-[3,4-dimethoxy-phenyl]-prop-2-enoic acid amide;
N-[2-(5-carbamimidoyl-2,3-dihydro-benzofuran-3-yl)-ethyl]-(5-oxo-5-phenyl-pentanoic acid)amide;
N-[2-(5-carbamimidoyl-2,3-dihydro-benzofuran-3-yl)-ethyl]-xanthine-9-carboxamide;
5-[1,2] dithiolan-3-yl-pentanoic acid-N-[2-(5-carbamimidoyl-2,3-dihydro-benzofuran-3-yl)-ethyl]-amide;
N-[2-(5-carbamimidoyl-2,3-dihydro-benzofuran-3-yl)-ethyl]-5-methoxy-indole-2 carboxamide;
N-[2-(5-carbamimidoyl-2,3-dihydro-benzofuran-3-yl)-ethyl]-3,4-methylenedioxy cinnamic acid amide;
N-[2-(5-carbamimidoyl-2,3-dihydro-benzofuran-3-yl)-ethyl]-3-quinoline carboxamide;
2,3-Dihydro-benzo[1,4]-dioxine-2-carboxylic acid-N-[2-(5-carbamimidoyl-2,3-dihydro-benzofuran-3-yl)-ethyl]-amide;
N-[2-(5-carbamimidoyl-2,3-dihydro-benzofuran-3-yl)-ethyl]-(2-[4-cyano-phenoxy)-2-methyl-propionamide;
N-[2-(5-carbamimidoyl-2,3-dihydro-benzofuran-3-yl)-ethyl]-2-(4-oxo-3,4-dihydro-pthalazin-1-yl)-acetamide;
3-Methyl-sulfanyl-4-oxo-4,5,6,7-tetrahydro-benzo[c]-thiophene-1-carboxylic acid N-[2-(5-carbamimidoyl-2,3-dihydro-benzofuran-3-yl)-ethyl]-amide;
4,5-Dimethyl-1-phenyl-pyrrole-3-carboxylic acid N-[2-(5-carbamimidoyl-2,3-dihydro-benzofuran-3-yl)-ethyl]-amide;
4-Oxo-4H-9-thia-1,4a-diaza-fluorene-3-carboxylic acid N-[2-(5-carbamimidoyl-2,3-dihydro-benzofuran-3-yl)-ethyl]-amide;
6-(1-pyrazole)-nicotinic acid N-[2-(5-carbamimidoyl-2,3-dihydro-benzofuran-3-yl)-ethyl]-amide;
3-Nitro-4-(1-pyrazolyl)benzoic acid N-[2-(5-carbamimidoyl-2,3-dihydro-benzofuran-3-yl)-ethyl]-amide;
N-Tosyl-3-pyrrole-carboxylic acid N-[2-(5-carbamimidoyl-2,3-dihydro-benzofuran-3-yl)-ethyl]-amide;
4-oxo-4,5,6,7-tetrahydro-benzofuran-3-carboxylic acid [2-(5-carbamimidoyl-2,3-dihydro-benzofuran-3-yl)-ethyl]-amide;
4-tert-butyl-2,6-dimethyl-cyclohexanecarboxylic acid [2-(5-carbamimidoyl-2,3-dihydro-benzofuran-3-yl)-ethyl]-amide;
5-methyl-1-(3-trifluoromethyl-phenyl)-4,5-dihydro-1H-1,2,3-triazole-4-carboxylic acid [2-(5-carbamimidoyl-2,3-dihydro-benzofuran-3-yl)-ethyl]-amide;
2-benzylsulfanyl-N-[2-(5-carbamimidoyl-2,3-dihydro-benzofuran-3-yl)-ethyl]-propionamide;
5-pyridin-2-yl-thiophene-2-carboxylic acid [2-(5-carbamimidoyl-2,3-dihydro-benzofuran-3-yl)-ethyl]-amide;
4-butyl-cyclohexanecarboxylic acid [2-(5-carbamimidoyl-2,3-dihydro-benzofuran-3-yl)-ethyl]-amide;
5-methyl-1-phenyl-1H-pyrazole-4-carboxylic acid [2-(5-carbamimidoyl-2,3-dihydro-benzofuran-3-yl)-ethyl]-amide;
N-[2-(5-carbamimidoyl-2,3-dihydro-benzofuran-3-yl)-ethyl]-6-pyrrol-1-yl-nicotinamide;
4-chloro-1,3-dimethyl-1H-pyrazolo[3,4-b]pyridine-5-carboxylic acid [2-(5-carbamimidoyl-2,3-dihydro-benzofuran-3-yl)-ethyl]-amide;
4-methyl-2-(4-trifluoromethyl-phenyl)-thiazole-5-carboxylic acid [2-(5-carbamimidoyl-2,3-dihydro-benzofuran-3-yl)-ethyl]-amide;
(S)-2-(6-Methoxynaphthyl)-N-(2-[5-carbamimidoyl-2,3-dihydrobenzofuran-3-yl]ethyl)propionamide;
N-(2-[5-Carbamimidoyl-2,3-dihydrobenzofuran-3-yl]ethyl)-3-chlorobenzothiophene-2-carboxamide;
4-Benzyloxy-N-(2-[5-carbamimidoyl-2,3-dihydrobenzofuran-3-yl]ethyl)benzamide;
4-(4-n-Propylphenyl)-N-(2-[5-carbamimidoyl-2,3-dihydrobenzofuran-3-yl]ethyl)benzamide;
2-Methylthio-N-(2-[5-carbamimidoyl-2,3-dihydrobenzofuran-3-yl]ethyl)benzamide;
3-(4-Pyridyl)-N-(2-[5-carbamimidoyl-2,3-dihydrobenzofuran-3-yl]ethyl)acrylamide;
N-(2-[5-Carbamimidoyl-2,3-dihydrobenzofuran-3-yl]ethyl)-4-tert-butylcyclohexanecarboxamide;
N-(2-[5-Carbamimidoyl-2,3-dihydrobenzofuran-3-yl]ethyl)-5-methylindole-2-carboxamide;
N-(2-[5-Carbamimidoyl-2,3-dihydrobenzofuran-3-yl]ethyl) quinoline-6-carboxamide;
N-(2-[5-Carbamimidoyl-2,3-dihydrobenzofuran-3-yl]ethyl) benzothiophene-2-carboxamide;
2-Pyrrolyl-N-(2-[5-carbamimidoyl-2,3-dihydrobenzofuran-3-yl]ethyl)benzamide;
4-Methyl-2-phenyl-N-(2-[5-carbamimidoyl-2,3-dihydrobenzofuran-3-yl]ethyl)-1,2,3-triazole-5-carboxamide;
N-(2-[5-Carbamimidoyl-2,3-dihydrobenzofuran-3-yl]ethyl)-phthalide-3-acetamide;
N-[2-(5-Carbamimidoyl-2,3-dihydro-Benzofuran-3-yl)-ethyl]-4-(phenyl)-benzamide;
N-[2-(5-Carbamimidoyl-2,3-dihydro-Benzofuran-3-yl)-ethyl]-4-(pyridin-3-yl)-benzamide;
4-(1-Aminomethyl-cyclopentyl)-N-[2-(5-carbamimidoyl-2,3-dihydro-benzofuran-3-yl)-ethyl]-benzamide;
N-[2-(5-carbamimidoyl-2,3-dihydro-Benzofuran-3-yl)-ethyl]-4-(pyridine-N-oxid-3-yl)-benzamide;
N-[2-(5-carbamimidoyl-2,3-dihydro-Benzofuran-3-yl)-ethyl]-4-(pyridin-4-yl)-benzamide;
N-[2-(5-carbamimidoyl-2,3-dihydro-Benzofuran-3-yl)-ethyl]-4-(6-oxo-1,6-dihydro-pyridin-3-yl)-benzamide;
N-[2-(5-carbamimidoyl-2,3-dihydro-Benzofuran-3-yl)-ethyl]-4-[(3-(aminomethyl)-phenyl]-benzamide;
N-[2-(5-carbamimidoyl-2,3-dihydro-Benzofuran-3-yl)-ethyl]-4-(pyridazin-3-yl)-benzamide;
N-[2-(5-carbamimidoyl-2,3-dihydro-Benzofuran-3-yl)-ethyl]-4-(pyridazin-4-yl)-benzamide;
N-[2-(5-carbamimidoyl-2,3-dihydro-Benzofuran-3-yl)-ethyl]-4-(pyrimidin-5-yl)-benzamide;
N-[Biphenyl-4-yl-methyl]-2-(5-carbamimidoyl-2,3-dihydro-benzofuranyl)acetamide;
N-[Biphenyl-4-yl]-2-(5-carbamimidoyl-2,3-dihydro-benzofuranyl)acetamide;
3-(3-Biphenyl-4-ylmethyl-ureido-methyl)-2,3-dihydrobenzofuran-5-carboxamidine;
3-[2-(4-Benzyl-piperidin-1-yl)-2-oxo-ethyl]-2,3-dihydrobenzofuran-5-carboxamidine;
3-{2-[4-(1,1-Dimethylpropyl)benzenesulfonylamino]ethyl}-5-carbamimidoyl-2,3-dihydrobenzofuran; and
3-[2-(7-Chlorobenzo[1,2,5]oxadiazole-5-sulfonylamino) ethyl]-5-carbamididoyl-2,3-dihydrobenzofuran.

23. A compound according to claim 1 which is selected from the group consisting of 5-(Pyridin-2-yl)-thiophene-2-carboxylic acid (2-[5-carbamimidoyl-2,3-dihydrobenzofuran-3-yl]ethyl)amide;
4-tert-Butyl-N-(2-[5-carbamimidoyl-2,3-dihydrobenzofuran-3-yl]ethyl)benzamide;

4-(2-Amino-1,1-dimethylethyl)-N-(2-[5-carbamimidoyl-2,3-dihydrobenzofuran-3-yl]ethyl)benzamide;

N-[2-(5-carbamimidoyl-2,3-dihydro-benzofuran-3-yl)-ethyl]-4-(3-amino-propyl)-benzamide;

N-[2-(5-Carbamimidoyl-2,3-dihydro-Benzofuran-3-yl)-ethyl]-4-(phenyl)-benzamide;

N-[2-(5-Carbamimidoyl-2,3-dihydro-Benzofuran-3-yl)-ethyl]-4-(pyridin-3-yl)-benzamide;

(1-Aminomethyl-cyclopentyl)-N-[2-(5-carbamimidoyl-2,3-dihydro-Benzofuran-3-yl)-ethyl]-benzamide;

N-[2-(5-carbamimidoyl-2,3-dihydro-Benzofuran-3-yl)-ethyl]-4-(pyridine-N-oxid-3-yl)-benzamide;

N-[2-(5-carbamimidoyl-2,3-dihydro-Benzofuran-3-yl)-ethyl]-4-(pyridin-4-yl)-benzamide;

N-[2-(5-carbamimidoyl-2,3-dihydro-Benzofuran-3-yl)-ethyl]-4-(6-oxo-1,6-dihydro-pyridin-3-yl)-benzamide;

N-[2-(5-carbamimidoyl-2,3-dihydro-Benzofuran-3-yl)-ethyl]-4-[(3-(aminomethyl)-phenyl]-benzamide;

N-[2-(5-carbamimidoyl-2,3-dihydro-Benzofuran-3-yl)-ethyl]-4-(pyridazin-3-yl)-benzamide;

N-[2-(5-carbamimidoyl-2,3-dihydro-Benzofuran-3-yl)-ethyl]-4-(pyridazin-4-yl)-benzamide; and N-[2-(5-carbamimidoyl-2,3-dihydro-Benzofuran-3-yl)-ethyl]-4-(pyrimidin-5-yl)-benzamide.

24. A pharmaceutical composition comprising a pharmaceutically acceptable amount of the compound according to claim 1 and a pharmaceutically acceptable carrier.

25. A method for treating a patient suffering from a physiological condition capable of being modulated by inhibiting activity of Factor Xa comprising administering a pharmaceutically effective amount of the compound according to claim 1.

26. The method according to claim 25 wherein the physiological condition is venous vasculature, arterial vasculature, abnormal thrombus formation, acute myocardial infarction, unstable angina, thromboembolism, acute vessel closure associated with thrombolytic therapy, percutaneous transluminal coronary angioplasty, transient ischemic attacks, stroke, intermittent claudication or bypass grafting of the coronary or peripheral arteries, vessel luminal narrowing, restenosis post coronary or venous angioplasty, maintenance of vascular access patency in long-term hemodialysis patients, pathologic thrombus formation occuring in the veins of the lower extremities following abdominal, knee and hip surgery, a risk of pulmonary thromboembolism, or disseminated systemic intravascular coagulopathy occurring in vascular systems during septic shock, certain viral infections or cancer.

27. The method according to claim 25 wherein the physiological condition is abnormal thrombus formation, acute myocardial infarction, unstable angina, thromboembolism, acute vessel closure associated with thrombolytic therapy, transient ischemic attacks, intermittent claudication or bypass grafting of the coronary or peripheral arteries, restenosis post coronary or venous angioplasty, pathologic thrombus formation occurring in the veins of the lower extremities following abdominal, knee and hip surgery or a risk of pulmonary thromboembolism.

28. The method according to claim 25 wherein the physiological condition is stroke, vessel luminal narrowing, maintenance of vascular access patency in long-term hemodialysis patients, or disseminated systemic intravascular coagulopathy occurring in vascular systems during septic shock, certain viral infections or cancer.

29. The method for treating a patient suffering from a physiological condition capable of being modulated by inhibiting the formation of thrombin comprising administering a pharmaceutically effective amount of the compound according to claim 1.

30. The method for treating a patient suffering from a physiological condition capable of being modulated by directly inhibiting activity of both Factor Xa and Factor IIa comprising administering a pharmaceutically effective amount of the compound according to claim 1.

* * * * *